(12) United States Patent
Alford et al.

(10) Patent No.: US 11,206,985 B2
(45) Date of Patent: Dec. 28, 2021

(54) NON-INVASIVE OPTICAL DETECTION SYSTEMS AND METHODS IN HIGHLY SCATTERING MEDIUM

(71) Applicant: HI LLC, Los Angeles, CA (US)

(72) Inventors: Jamu Alford, Simi Valley, CA (US); Adam Marblestone, Arlington, MA (US)

(73) Assignee: HI LLC, Los Angeles, CA (US)

( * ) Notice: Subject to any disclaimer, the term of this patent is extended or adjusted under 35 U.S.C. 154(b) by 478 days.

(21) Appl. No.: 16/299,067

(22) Filed: Mar. 11, 2019

(65) Prior Publication Data

US 2019/0313912 A1 Oct. 17, 2019

Related U.S. Application Data

(60) Provisional application No. 62/657,634, filed on Apr. 13, 2018.

(51) Int. Cl.
*A61B 5/00* (2006.01)
*G01N 21/49* (2006.01)

(52) U.S. Cl.
CPC .......... *A61B 5/0059* (2013.01); *A61B 5/0013* (2013.01); *A61B 5/0042* (2013.01);
(Continued)

(58) Field of Classification Search
CPC ... A61B 5/0059; A61B 5/0042; A61B 5/6803; A61B 5/0013; A61B 2576/026;
(Continued)

(56) References Cited

U.S. PATENT DOCUMENTS

| 5,213,105 A | 5/1993 | Gratton et al. |
| 5,856,667 A | 1/1999 | Spirig et al. |

(Continued)

FOREIGN PATENT DOCUMENTS

| AU | 2009305257 | 5/2014 |
| CN | 102176859 | 1/2014 |

(Continued)

OTHER PUBLICATIONS

Gross 2016 arXiv 1606 02902v1 5pages Jun. 9, 2016 (Year: 2016).*

(Continued)

*Primary Examiner* — Keith M Raymond
*Assistant Examiner* — Patrick M Mehl
(74) *Attorney, Agent, or Firm* — Michael J. Bolan; Vista IP Law Group, LLP

(57) ABSTRACT

A non-invasive optical detection system and method are provided. Sample light is delivered into a target volume of interest, whereby the sample light is scattered by the target volume of interest, resulting in a sample light pattern that exits the anatomical structure. Reference light is combined with the sample light pattern to generate at least one interference light pattern, each of which may have a time varying interference component that integrates to a first value in the absence of the physiological event, and that integrates to a second greater value in the presence of the physiological event. Intensities of spatial components of each interference light pattern are detected during a measurement period. A function of the detected spatial component intensities of the interference light pattern(s) is analyzed, and a presence of the physiological event in the target volume of interest is determined based on the analysis.

19 Claims, 30 Drawing Sheets

(52) U.S. Cl.
CPC ........... *A61B 5/6803* (2013.01); *G01N 21/49* (2013.01); *A61B 2562/0238* (2013.01); *A61B 2576/026* (2013.01)

(58) Field of Classification Search
CPC .......... A61B 2562/0238; A61B 5/4064; G01N 21/49; G01N 21/45; G16H 30/40
See application file for complete search history.

(56) References Cited

U.S. PATENT DOCUMENTS

| | | | |
|---|---|---|---|
| 6,041,248 A | 3/2000 | Wang | |
| 6,205,353 B1 | 3/2001 | Alfano et al. | |
| 6,334,699 B1 | 1/2002 | Gladnick | |
| 6,738,653 B1 | 5/2004 | Sfez et al. | |
| 6,777,659 B1 | 8/2004 | Schwarte | |
| 6,825,455 B1 | 11/2004 | Schwarte | |
| 6,957,096 B2 | 10/2005 | Sfez et al. | |
| 7,053,357 B2 | 5/2006 | Schwarte | |
| 7,060,957 B2 | 6/2006 | Lange et al. | |
| 7,119,906 B2 | 10/2006 | Pepper et al. | |
| 7,144,370 B2 | 12/2006 | Fomitchov | |
| 7,365,859 B2 * | 4/2008 | Yun | G01N 21/4795 356/479 |
| 7,498,621 B2 | 3/2009 | Seitz | |
| 7,508,505 B2 | 3/2009 | Lustenberger et al. | |
| 7,515,948 B1 | 4/2009 | Balberg et al. | |
| 7,521,663 B2 | 4/2009 | Wäny | |
| 7,541,602 B2 | 6/2009 | Metzger et al. | |
| 7,560,701 B2 | 7/2009 | Oggier et al. | |
| 7,586,077 B2 | 9/2009 | Lehmann et al. | |
| 7,595,476 B2 | 9/2009 | Beer et al. | |
| 7,620,445 B2 | 11/2009 | Tsujita | |
| 7,622,704 B2 | 11/2009 | Wäny | |
| 7,647,830 B2 | 1/2010 | Sfez et al. | |
| 7,671,671 B2 | 3/2010 | Buettgen et al. | |
| 7,701,028 B2 | 4/2010 | Kaufmann et al. | |
| 7,733,742 B2 | 6/2010 | Gross et al. | |
| 7,747,301 B2 | 6/2010 | Cheng et al. | |
| 7,884,310 B2 | 2/2011 | Buettgen | |
| 7,889,257 B2 | 2/2011 | Oggier et al. | |
| 7,897,928 B2 | 3/2011 | Kaufmann et al. | |
| 7,898,649 B2 | 3/2011 | Masumura | |
| 7,917,312 B2 | 3/2011 | Wang et al. | |
| 7,923,673 B2 | 4/2011 | Büttgen et al. | |
| 8,017,858 B2 | 9/2011 | Mann | |
| 8,044,999 B2 | 10/2011 | Mullen et al. | |
| 8,103,329 B2 | 1/2012 | Fomitchov et al. | |
| 8,106,472 B2 | 1/2012 | Kaufmann et al. | |
| 8,108,022 B2 | 1/2012 | Balberg et al. | |
| 8,115,158 B2 | 2/2012 | Buettgen | |
| 8,126,524 B2 | 2/2012 | Balberg et al. | |
| 8,143,605 B2 | 3/2012 | Metzger et al. | |
| 8,223,215 B2 | 7/2012 | Oggier et al. | |
| 8,280,494 B2 | 10/2012 | Masumura | |
| 8,289,502 B2 | 10/2012 | Koshida | |
| 8,299,504 B2 | 10/2012 | Seitz | |
| 8,315,483 B2 | 11/2012 | Shuster | |
| 8,326,567 B2 | 12/2012 | Masumura | |
| 8,336,391 B2 | 12/2012 | Rokni et al. | |
| 8,385,691 B2 | 2/2013 | Shuster | |
| 8,400,149 B2 | 3/2013 | Stoughton et al. | |
| 8,405,823 B2 | 3/2013 | Pfaff | |
| 8,423,116 B2 | 4/2013 | Balberg et al. | |
| 8,450,674 B2 | 5/2013 | Yang et al. | |
| 8,454,512 B2 | 6/2013 | Wang et al. | |
| 8,525,998 B2 | 9/2013 | Yaqoob et al. | |
| 8,562,658 B2 | 10/2013 | Shoham et al. | |
| 8,644,900 B2 | 2/2014 | Balberg et al. | |
| 8,717,574 B2 | 5/2014 | Yang et al. | |
| 8,754,939 B2 | 6/2014 | Oggier et al. | |
| 8,803,967 B2 | 8/2014 | Oggier et al. | |
| 8,817,255 B2 | 8/2014 | Masumura | |
| 8,830,573 B2 | 9/2014 | Cui et al. | |
| 8,867,798 B2 | 10/2014 | Shuster | |
| 8,917,442 B2 | 12/2014 | Baym et al. | |
| 8,922,759 B2 | 12/2014 | Gassert et al. | |
| 8,954,130 B2 * | 2/2015 | Masumura | G01N 29/2418 600/407 |
| 8,964,028 B2 | 2/2015 | Oggier | |
| 8,970,850 B2 * | 3/2015 | Yan | G01B 11/2441 356/511 |
| 8,976,433 B2 | 3/2015 | Masumura | |
| 8,997,572 B2 | 4/2015 | Wang et al. | |
| 9,000,349 B1 | 4/2015 | Lehmann et al. | |
| 9,027,412 B2 | 5/2015 | Rokni et al. | |
| 9,046,338 B2 | 6/2015 | Boccara et al. | |
| 9,057,695 B2 | 6/2015 | Masumura | |
| 9,076,709 B2 | 7/2015 | Felber et al. | |
| 9,086,365 B2 | 7/2015 | Wang et al. | |
| 9,117,712 B1 | 8/2015 | Oggier et al. | |
| 9,131,170 B2 | 9/2015 | Mandelis et al. | |
| 9,131,880 B2 | 9/2015 | Balberg | |
| 9,140,795 B2 | 9/2015 | Lehmann et al. | |
| 9,164,033 B2 | 10/2015 | Edwards et al. | |
| 9,167,970 B2 * | 10/2015 | Gratton | A61B 5/0042 |
| 9,192,294 B2 * | 11/2015 | Sharma | A61B 3/102 |
| 9,209,327 B2 | 12/2015 | Neukom et al. | |
| 9,226,666 B2 | 1/2016 | Wang et al. | |
| 9,232,896 B2 | 1/2016 | Baym et al. | |
| 9,234,841 B2 | 1/2016 | Wang et al. | |
| 9,237,850 B2 | 1/2016 | Metzger et al. | |
| 9,282,931 B2 | 3/2016 | Tearney et al. | |
| 9,304,490 B2 | 4/2016 | Masumura | |
| 9,313,423 B2 | 4/2016 | Wang et al. | |
| 9,329,035 B2 | 5/2016 | Oggier | |
| 9,335,154 B2 | 5/2016 | Wax et al. | |
| 9,335,605 B2 | 5/2016 | Wang et al. | |
| 9,341,715 B2 | 5/2016 | Buettgen et al. | |
| 9,351,705 B2 | 5/2016 | Wang et al. | |
| 9,435,891 B2 | 9/2016 | Oggier | |
| 9,442,196 B2 | 9/2016 | Buettgen et al. | |
| 9,466,938 B2 | 10/2016 | Dupret et al. | |
| 9,486,128 B1 | 11/2016 | Hannaford et al. | |
| 9,488,573 B2 | 11/2016 | Edwards et al. | |
| 9,528,966 B2 | 12/2016 | Wang et al. | |
| 9,555,444 B2 | 1/2017 | Goodman et al. | |
| 9,619,486 B2 | 4/2017 | Shuster | |
| 9,655,527 B2 | 5/2017 | Wang et al. | |
| 9,668,672 B2 | 6/2017 | Zalevsky et al. | |
| 9,698,196 B2 | 7/2017 | Buettgen et al. | |
| 9,713,448 B2 | 7/2017 | Caplan et al. | |
| 9,720,505 B2 | 8/2017 | Gribetz et al. | |
| 9,730,649 B1 | 8/2017 | Jepsen | |
| 9,839,365 B1 | 12/2017 | Homyk et al. | |
| 2005/0085725 A1 | 4/2005 | Nagar et al. | |
| 2005/0256403 A1 | 11/2005 | Fomitchov | |
| 2006/0023621 A1 | 2/2006 | Hwang et al. | |
| 2006/0122475 A1 | 6/2006 | Balberg et al. | |
| 2006/0184042 A1 | 8/2006 | Wang et al. | |
| 2006/0184049 A1 | 8/2006 | Tsujita | |
| 2006/0224053 A1 | 10/2006 | Black et al. | |
| 2006/0247506 A1 | 11/2006 | Balberg et al. | |
| 2006/0253007 A1 | 11/2006 | Cheng et al. | |
| 2006/0264717 A1 | 11/2006 | Pesach et al. | |
| 2007/0093702 A1 | 4/2007 | Yu et al. | |
| 2008/0094633 A1 * | 4/2008 | Dimarzio | G01N 29/346 356/450 |
| 2008/0219584 A1 | 9/2008 | Mullen et al. | |
| 2008/0296514 A1 | 12/2008 | Metzger et al. | |
| 2008/0312533 A1 | 12/2008 | Balberg et al. | |
| 2009/0066949 A1 | 3/2009 | Masumura | |
| 2009/0069674 A1 | 3/2009 | Masumura et al. | |
| 2009/0069676 A1 | 3/2009 | Nishihara | |
| 2009/0069685 A1 | 3/2009 | Nishihara et al. | |
| 2009/0069687 A1 | 3/2009 | Igarashi | |
| 2009/0124902 A1 | 5/2009 | Herrmann | |
| 2009/0171210 A1 | 7/2009 | Wang | |
| 2009/0253989 A1 | 10/2009 | Caplan et al. | |
| 2009/0264722 A1 | 10/2009 | Metzger et al. | |
| 2010/0000330 A1 | 1/2010 | Rokni et al. | |
| 2010/0069750 A1 | 3/2010 | Masumura | |
| 2010/0070233 A1 | 3/2010 | Masumura | |
| 2010/0073674 A1 | 3/2010 | Koshida | |

(56) References Cited

U.S. PATENT DOCUMENTS

| | | |
|---|---|---|
| 2010/0152559 A1 | 6/2010 | Cheng et al. |
| 2010/0152591 A1 | 6/2010 | Yu et al. |
| 2010/0285518 A1 | 11/2010 | Viator et al. |
| 2011/0071402 A1 | 3/2011 | Masumura |
| 2011/0101241 A1 | 5/2011 | Cottier et al. |
| 2011/0172513 A1 | 7/2011 | Nakajima et al. |
| 2011/0228097 A1 | 9/2011 | Motta |
| 2011/0237956 A1 | 9/2011 | Edwards et al. |
| 2011/0249912 A1 | 10/2011 | Shuster |
| 2012/0022381 A1 | 1/2012 | Tearney et al. |
| 2012/0070817 A1 | 3/2012 | Wang et al. |
| 2012/0127557 A1 | 5/2012 | Masumura |
| 2012/0275262 A1 | 11/2012 | Song et al. |
| 2014/0218748 A1 | 8/2014 | Wax et al. |
| 2015/0238092 A1 | 8/2015 | Masumura |
| 2015/0245771 A1 | 9/2015 | Wang et al. |
| 2016/0187533 A1 | 6/2016 | Maucec et al. |
| 2016/0235305 A1 | 8/2016 | Wang et al. |
| 2016/0249812 A1 | 9/2016 | Wang et al. |
| 2016/0299218 A1 | 10/2016 | Lehmann |
| 2016/0305914 A1 | 10/2016 | Wang et al. |
| 2017/0038000 A1 | 2/2017 | Fuchsle et al. |
| 2017/0038300 A1 | 2/2017 | Dake et al. |
| 2017/0038459 A1 | 2/2017 | Kubacki et al. |
| 2017/0065182 A1 | 3/2017 | Wang et al. |
| 2017/0090018 A1 | 3/2017 | Buettgen et al. |
| 2017/0105636 A1 | 4/2017 | Wang et al. |
| 2017/0122915 A1 | 5/2017 | Vogt et al. |

FOREIGN PATENT DOCUMENTS

| | | |
|---|---|---|
| CN | 104107051 | 10/2014 |
| CN | 104382558 | 3/2015 |
| EP | 1458087 | 10/2005 |
| EP | 1771844 | 4/2007 |
| EP | 2016891 | 1/2009 |
| EP | 2036487 | 3/2009 |
| EP | 2036488 | 3/2009 |
| EP | 2036490 | 3/2009 |
| EP | 2163189 | 3/2010 |
| EP | 1675501 | 9/2013 |
| EP | 1771882 | 9/2013 |
| EP | 2240798 | 8/2016 |
| EP | 2594959 | 1/2017 |
| EP | 2815251 | 3/2017 |
| JP | 2009501581 | 1/2009 |
| WO | WO2005025399 A2 | 3/2005 |
| WO | WO2005025399 A3 | 5/2005 |
| WO | WO2007035934 | 3/2007 |
| WO | WO2008040771 A2 | 4/2008 |
| WO | WO2008040771 A3 | 8/2008 |
| WO | WO2010043851 | 4/2010 |
| WO | WO2012080837 | 6/2012 |
| WO | WO2012080838 | 6/2012 |
| WO | WO2014106823 | 7/2014 |
| WO | WO2016138637 | 9/2016 |
| WO | WO2016193554 | 12/2016 |

OTHER PUBLICATIONS

Lai et al 2013 Proc SPIE 8581 PPUIS 2013 85812X-1-85812X9 (Year: 2013).*
Ruan et al. 2013 J Opt Soc Am A 30 1409-1416 (Year: 2013).*
Smith et al 2013 PNAS 110 19391-18396 (Year: 2013).*
Razavi 2018 PhD. Thesis Manufacturing Engineering Worcester Polytechnic Institute 214 pages (Year: 2018).*
Atlan, M. et al., "Pulsed acousto-optic imaging in dynamic scattering media with heterodyne parallel speckle detection", Optics Letters, vol. 30, No. 11, Jun. 1, 2005, 1360-1362.
Choma, Michael A. et al., "Instantaneous quadrature low-coherence interferometry with 3 x 3 fiber-optic couplers", Optic Letters, vol. 28, No. 22, Nov. 15, 2003, 2162-2164.
Hale, Thomas C. et al., "Photorefractive optical lock-in vibration spectral measurement", Applied Optics, vol. 36, No. 31, Nov. 1, 1997, 8248-8258.
Khoury, Jehad et al., "Photorefractive optical lock-in detector", Optics Letters, vol. 16, No. 18, Sep. 15, 1991, 1442-1444.
Li, Youzhi et al., "Pulsed ultrasound-modulated optical tomography using spectral-hole burning as a narrowband spectral filter", Applied Physics Letter, 93, 011111 (2008).
Liu, Yan et al., "Bit-efficient, sub-millisecond wavefront measurement using a lock-in camera for time-reversal based optical focusing inside scattering media", Opt. Lett. Apr. 1, 2016; 41(7): 1321-1324.
Liu, Yan et al., "Lock-in camera based heterodyne holography for ultrasound-modulated optical tomography inside dynamic scattering media", Appl. Phys. Lett. 108, 231106 (2016).
Mao, Shu et al., "Optical Lock-In Detection of FRET Using Synthetic and Genetically Encoded Optical Switches", Biophysical Journal, vol. 94, Jun. 2008, 4515-4524.
Marriott, Gerard et al., "Optical lock-in detection imaging microscopy for contrast-enhanced imaging in living cells", PNAS, Nov. 18, 2008, vol. 105, No. 46, 17789-17794.
Ruan, Haowen et al., "Pulsed ultrasound modulated optical tomography with harmonic lock-in holography detection", J. Opt. Soc. Am. A, vol. 30, No. 7, Jul. 2013, 1409-1416.
Strauss, Charlie E.M. et al., "Synthetic-array heterodyne detection: a single-element detector acts as an array", Oct. 15, 1994, vol. 19, No. 20, Optics Letters, 1609-1611.
Tucker-Schwartz, Jason M. et al., "Photothermal optical lock-in optical coherence tomography for in vivo imaging", Jun. 1, 2015, vol. 6, No. 6, DOI:10.1364/BOE.6.002268, Biomedical Optics Express, 2268-2282.
Yaqoob, Zahid et al., "Harmonically-related diffraction gratings-based interferometer for quadrature phase measurements", Sep. 4, 2006, vol. 14, No. 18, Optics Express, 8127-8137.
Gratton, Gabriele et al., "Dynamic brain imaging: Event-related optical signal (EROS) measures of the time course and localization of cognitive-related activity", Psychonomic Bulletin & Review, 1998, 5 (4), 535-563.
Matthews, Thomas E. et al., "Deep tissue imaging using spectroscopic analysis of multiply scattered light", Optica, vol. 1, No. 2, Aug. 2014, 105-111.
Giacomelli, Michael G. et al., "Imaging beyond the ballistic limit in coherence imaging using multiply scattered light", Optics Express, Feb. 28, 2011, vol. 19, No. 5, 4268-4279.
Puszka, Agathe et al., Time-resolved diffuse optical tomography using fast-gated single-photon avalanche diodes, Aug. 1, 2013, vol. 4, No. 8, DOI:10.1364/BOE.4.001351, Biomedical Optics Express, 1351-1365.
Broussard GJ, Liang R, Tian L., "Monitoring activity in neural circuits with genetically encoded indicators", Frontiers in molecular neuroscience, 2014;7.
Franceschini MA, Fantini S, Toronov V, Filiaci ME, Gratton E., "Cerebral hemodynamics measured by near-infrared spectroscopy at rest and during motor activation". In Proceedings of the Optical Society of America in Vivo Optical Imaging Workshop 2000 (pp. 73-80), Optical Society of America.
Franceschini, MA and Boas, DA, "Noninvasive Measurement of Neuronal Activity with Near-Infrared Optical Imaging," Neuroimage, vol. 21, No. 1, pp. 372-386 (Jan. 2004).
Goense J, Merkle H, Logothetis NK, "High-resolution of fMRI reveals laminar differences in neurovascular coupling between positive and negative BOLD responses". Neuron, Nov. 8, 2012; 76(3):629-39.
Gratton G, Fabiani M., "Fast optical imaging of human brain function", Frontiers in human neuroscience, Jun. 2010;4.
Horinaka H, Osawa M. Hashimoto K, Wada K, Cho Y., "Extraction of quasistraightforward- propagating photons from diffused light transmitting through a scattering medium by polarization modulation". Optics Letters, Jul. 1, 1995; 20(13):1501-3.
Horstmeyer R., Ruan H, Yang C, "Guidestar-Assisted Wavefront-Shaping Methods for Focusing Light into Biological Tissue," Nature Photonics, vol. 9, No. 9, pp. 563-571 (Sep. 1, 2015).
Laforest T, Verdant A, Dupret A, Gigan S., Ramaz F, Tessier G, "Co-Integration of a Smart CMOS Image Sensor and a Spatial Light

(56) References Cited

OTHER PUBLICATIONS

Modulator for Real-Time Optical Phase Modulation," Proc. of SPIE-IS&T, vol. 2014, 9022:90220N-1 (Mar. 1, 2014).

Leveque S, Boccara AC, Lebec M, Saint-Jalmes H, "Ultrasonic tagging of photon paths in scattering media: parallel speckle modulation processing". Optics Letters, Feb. 1, 1999; 24(3):181-3.

Liu Y, Ma C, Shen Y, Wang LV, "Bit-Efficient, Sub-Millisecond Wavefront Measurement Using a Lock-In Camera for Time-Reversal Based Optical Focusing Inside Scattering Media," Optics Letters, vol. 41, No. 7, pp. 1321-1324, Apr. 1, 2016.

Liu Y, Shen Y, Ma C, Shi J, Wang LV, "Lock-in Camera Based Heterodyne Holography for Ultrasound-Modulated Optical Tomography Inside Dynamic Scattering Media," Applied Physics Letters, vol. 108, No. 23, 231106, Jun. 6, 2016.

Mahan GD, Engler WE, Tiemann JJ, Uzgiris E, "Ultrasonic Tagging of Light: Theory," Proceedings of the National Academy of Sciences, vol. 95, No. 24, pp. 14015-14019, Nov. 24, 1998.

Patwardhan SV, Culver JP. Quantitative diffuse optical tomography for small animals using an ultrafast gated image intensifier. Journal of biomedical optics. Jan. 1, 2008; 13(1):011009.

Powell S., Srridge SR, Leung TS, "Gradient-Based Quantitative Image Reconstruction in Ultrasound-Modulated Optical Tomography: First Harmonic Measurement Type in a Linearized Diffusion Formulation," IEEE Transactions on Medical Imaging, vol. 35, No. 2, pp. 456-467 (Feb. 2016).

Qureshi MM, Brake J., Jeon HJ, Ruan H, Liu Y, Safi AM, Eom TJ, Yang C., Chung E, "In Vivo Study of Optical Speckle Decorrelation Time Across Depths in the Mouse Brain," Biomedical Optics Express, vol. 8, No. 11, pp. 4855-4864 (Nov. 1, 2017).

Sakadzic S, Wang LV, "High-Resolution Ultrasound-Modulated Optical Tomography in Biological Tissues," Optics Letters, vol. 29, No. 23, pp. 2770-2772, Dec. 1, 2004).

Schmitt, JM, Gandjbackhche, AH, Bonner RF, "Use of polarized light to discriminate short-part photons in a multiply scattering medium". Applied Optics, Oct. 20, 1992; 31(30):6535-46.

Steinbrink J, Villringer A, Kempf F, Haux D. Boden S, Obrig H., "Illuminating the BOLD Signal: Combined fMRI-fNIRS Studies," Magnetic Resonance Imaging, vol. 24, No. 4, pp. 495-505, May 31, 2006).

Van der Laan JD, Wright JB, Scrymgeour DA, Kemme SA, Dereniak EL, "Evolution of circular and linear polarization in scattering environments", Optics Express, Dec. 14, 2015; 23(25):31874-88.

Wang YM, Judkewitz B, DiMarzio GA, Yang C., "Deep-Tissue Focal Fluorescence Imaging with Digitally Time-Reversed Ultrasound-Encoded Light," Nature Communications, vol. 3, Article 928 (Jun. 16, 2012).

Wang, RK, Jacques SL, Ma Z, Hurst S, Hanson SR, Gruber A, Three dimensional optical angiography. Optics Express, Apr. 2, 2007; 15(7):4083-97.

Xu X, Liu H., Wang LV, "Time-Reversed Ultrasonically Encoded Optical Focusing into Scattering Media," Nature Photonics, vol. 5, No. 3, pp. 154-157 (Mar. 1, 2011).

Hill D.K. and Keynes, R.D., "Opacity Changes in Stimulated Nerve," J. Physiol., vol. 108, pp. 278-281 (1949).

Foust A.J. and Rector D.M., "Optically Teasing Apart Neural Swelling and Depolarization," Neuroscience, vol. 145, pp. 887-899 (2007).

* cited by examiner

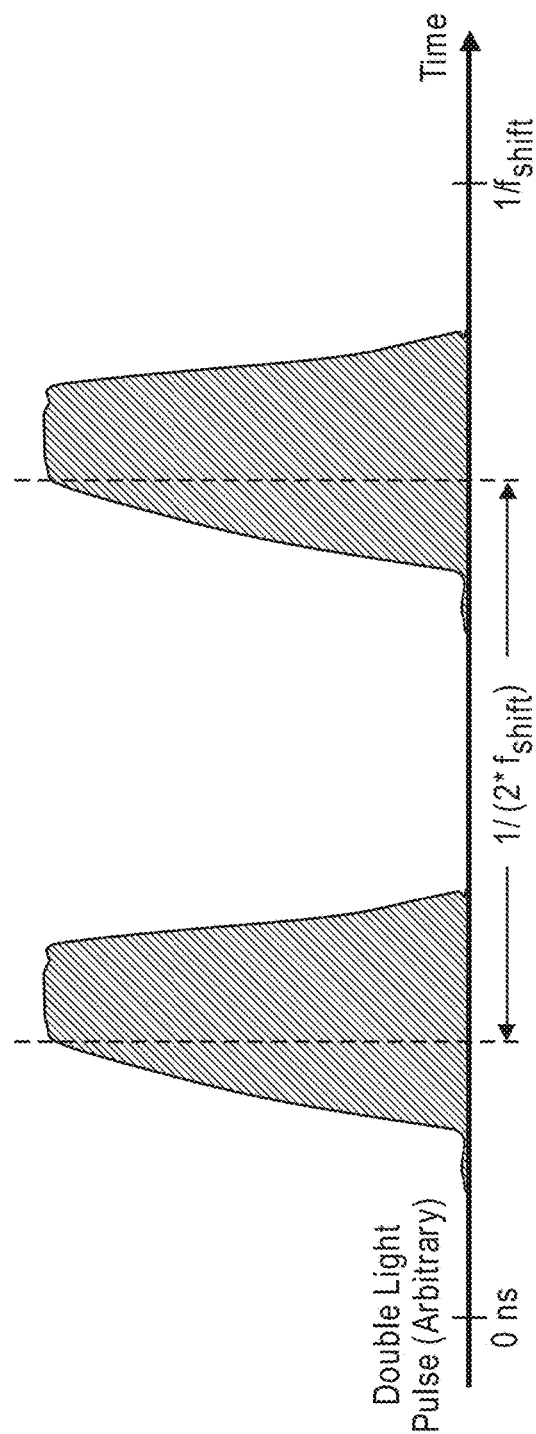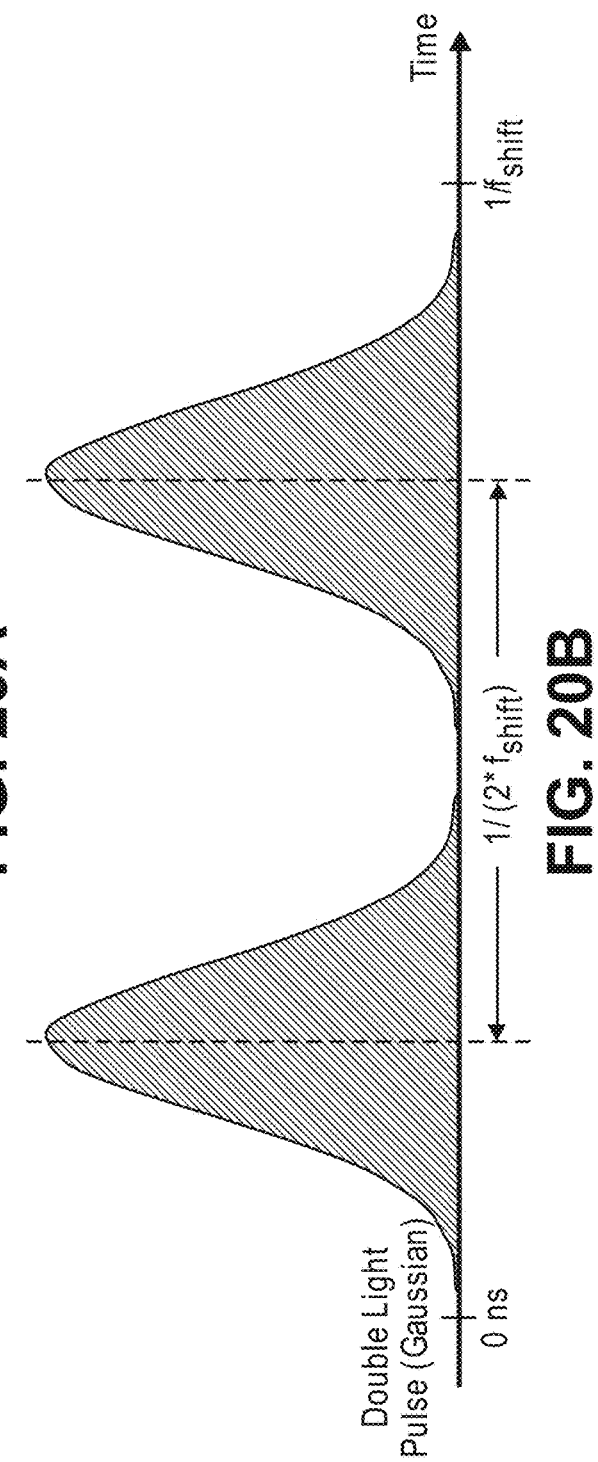

NON-INVASIVE OPTICAL DETECTION SYSTEMS AND METHODS IN HIGHLY SCATTERING MEDIUM

RELATED APPLICATION DATA

This application claims the benefit of U.S. Provisional Patent Application 62/657,634, filed Apr. 13, 2018, which is expressly incorporated herein by reference.

FIELD OF THE INVENTION

The present invention relates to methods and systems for non-invasive measurements in the human body, and in particular, methods and systems related to detecting physiologically dependent optical parameters in the human body.

BACKGROUND OF THE INVENTION

Measuring neural activity in the brain is useful for medical diagnostics, neuromodulation therapies, neuroengineering, or brain-computer interfacing. For example, it may be desirable to measure neural activity in the brain of a patient to determine if a particular region of the brain has been impacted by reduced blood irrigation, a hemorrhage, any other type of damage. For instance, in cases where the patient has suffered a traumatic brain injury, such as stroke, it may be desirable to determine whether the patient should undergo a therapeutic procedure. Measuring neural activity in the brain also may be used to determine the efficacy of such a therapeutic procedure.

Conventional methods for measuring neural activity in the brain include diffusive optical imaging techniques, which employ moderate amounts of near-infrared or visible light radiation, thus being comparatively safe and gentle for a biological subject in comparison to X-Ray Computed Tomography (CT) scans, positron emission tomography (PET), or other methods that use higher-energy and potentially harmful radiation. Moreover, in contrast to methods, such as functional magnetic resonance imaging (fMRI), these optically-based imaging methods do not require large magnets or magnetic shielding, and thus, can be scaled to wearable or portable form factors, which is especially important in applications, such as brain-computer interfacing.

There is an increasing interest in measuring fast-optical signals, which refers to changes in optical scattering that occur when light propagating through active neural tissue (e.g., active brain tissue) is perturbed through a variety of mechanisms, including, but not limited to, cell swelling, cell volume change, changes in membrane potential, changes in membrane geometry, ion redistribution, birefringence changes, etc. (see Hill D. K. and Keynes, R. D., "Opacity Changes in Stimulated Nerve," J. Physiol., Vol. 108, pp. 278-281 (1949); Foust A. J. and Rector D. M., "Optically Teasing Apart Neural Swelling and Depolarization," Neuroscience, Vol. 145, pp. 887-899 (2007)). Because fast-optical signals are associated with neuronal activity, rather than hemodynamic responses, fast-optical signals may be used to detect brain activity with relatively high temporal resolution.

However, because optical imaging techniques rely on light, which scatters many times inside brain, skull, dura, pia, and skin tissues, the light paths occurring in these techniques comprise random or "diffusive" walks, and therefore, only limited spatial resolution can be obtained by a conventional optical detector, often on the order of centimeters, with penetration depths being limited to a few millimeters. The reason for this limited spatial resolution is that the paths of photons striking the detector in such schemes are highly variable and difficult, and even impossible, to predict without detailed microscopic knowledge of the scattering characteristics of the brain volume of interest, which is typically unavailable in practice (i.e., in the setting of non-invasive measurements through skull for brain imaging and brain interfacing). In summary, light scattering has presented challenges for optical detection techniques in achieving high spatial resolution deep inside tissue. Moreover, the diffusive nature of light propagation also creates challenges for measurements of fast changes in optical scattering inside tissue, since essentially all paths between source and detector are highly scattered to begin with.

Diffusive optical imaging techniques have been used to increase spatial resolution by locating a multitude of optical sources and detectors along the surface of the head that, despite the random propagation of light from the optical sources, can identify bundles through which photons are likely to travel during the random motion (See Gratton G., Fabiani M, "Fast-optical Imaging of Human Brain Function," Vol. 4, Article 52, pp. 1-9 (June 2010)). As described in Gratton, two basic technologies for diffusive optical imaging are currently available: a continuous-wave (or CW) technique that uses a constant or slowly oscillating (less than 10 kHz) source of light to detect intensity, and frequency domain near-infrared spectroscopy (phase delay technique) that uses rapidly varying sources of light (e.g., sinusoidally modulated at least 100 MHz) to detect not only the light intensity, but also the average time required by photons to travel between the source and a detector.

The basic assumption for detecting naturally occurring fast-optical signals using diffusive optical imaging techniques is that fast-optical signals change the path length distribution of light propagating through a sample. More relevant to the phase delay technique used with frequency domain diffuse optical tomography to measure fast optical signals, the mechanisms of fast-optical signals alter the amount or directionality distribution of local scattering, thereby scattering light towards deeper or shallower depths, resulting in more or less time spent in the tissue or other changes in the fraction of photons traveling on deep versus shallower paths through tissue, or more generally longer or shorter paths through tissue. Thus, fast-optical signals give rise to or are correlated with a change in average optical path length between source and for diffusive light propagating through the sample.

Gratton concludes that the phase delay technique relative to the CW technique is particularly interesting for detecting fast-optical signals associated with changing light scattering inside the brain since, compared to light intensity measurements, phase delay measurements have a greater sensitivity for deeper locations due to the fact that photons traveling a very long path have a greater influence on the mean value of phase delay; phase delay measurements have a greater spatial resolution due to the large effect on the phase value in response to even small changes in the relative number of photons traveling long or short paths (5-10 mm for phase delay measurement compared to 10-20 mm for intensity measurements); and phase delay measurements are largely insensitive to variations in the total amount of light injected into the tissue or measured by the detector, since such variations will equally influence photons traveling long and shorter paths, and therefore have no net effect on the phase delay parameter, and thus are largely insensitive to movements.

However, fast-optical signals are very small (on the order of 1/1000 for intensity measurements and picoseconds or fractions thereof for phase delay measurement), and thus, there is a challenge separating fast-optical signals from background noise. Gratton has proposed reducing the background noise by using signal averaging over a large number of trials. The disadvantage of this is, of course, the requirement that multiple measurements would need to be taken to detect a fast-optical signal in a single volume of interest in tissue, limiting applicability for "real time" applications, e.g., brain-computer interfacing.

There, thus, remains a need to provide an optical detection system for diffuse optical tomography with an improved temporal sensitivity to detect fast-optical signals.

SUMMARY OF THE INVENTION

In accordance with a first aspect of the present inventions, a non-invasive optical detection system comprises an interferometer configured for delivering sample light into a target volume of interest within an anatomical structure or biological tissue sample, whereby the sample light is scattered by the target volume of interest, resulting in a sample light pattern that exits the anatomical structure. The interferometer is further configured for combining reference light with the sample light pattern to generate at least one interference light pattern (e.g., a speckle light pattern), each having spatial components (e.g., speckle grains). In one embodiment, the interferometer comprises a light source configured for generating source light, and a beam splitter configured for splitting the source light into the sample light and the reference light.

The non-invasive optical detection system further comprises at least one array of detectors respectively configured for detecting intensities of the spatial components of the interference light pattern(s) during a measurement period. In one embodiment, a single interference light pattern is generated, in which case, a single array of detectors is configured for detecting intensities of the spatial components of the interference light pattern(s). In another embodiment, two interference light patterns are generated, in which case, two arrays of detectors are configured for respectively detecting intensities of the spatial components of the two interference light patterns. The sample light may comprise at least one pulse (e.g., a single pulse or a plurality of pulses) delivered into the target volume of interest during the measurement period. In another embodiment, the interferometer may be further configured for shifting the sample light relative to the reference light by a frequency offset, such that the sample light pattern and the reference light are combined using a heterodyning technique. In this case, the measurement period may be equal to an inverse of the frequency offset between the sample light and the reference light.

In another embodiment, the interferometer is configured for combining the reference light with the sample light pattern, such that each of the interference light pattern(s) has a time varying interference component that integrates to a first value over the measurement period in the absence of the physiological event in the target volume of interest, and that integrates to a second value greater than the first value over the measured period in the presence of the physiological event.

The first value may be approximately zero, and may be equal to or less than one percent of the absolute integral of the time varying interference component. For example, if the interferometer is configured for shifting the sample light relative to the reference light by a frequency offset, the sample light may comprise a rectangular pulse, in which case, the product of the frequency offset between the sample light and the reference light and a duration of the rectangular pulse may be equal to one. As another example, the sample light may comprise two identical pulses (e.g., two Gaussian pulses or even two arbitrarily-shaped pulses) separated from each other by the inverse of two times the frequency offset between the sample light and the reference light. In an optional embodiment, the optical detection system comprises a controller is configured for using feedback control to periodically modify one or more of a waveform shape of the sample light and the frequency offset between the sample light and the reference light to minimize the first value.

The non-invasive optical detection system further comprises a processor configured for analyzing an intensity population distribution of a function of the detected spatial component intensities of the interference light pattern(s). In the case of a single interference light pattern, the function may be an identify function, and in the case of two interference light patterns (which may have a phase difference of 180 degrees), the function may be a subtraction function. The processor is further configured for determining a spread of the analyzed intensity population distribution (e.g., by computing a standard deviation of the intensity population distribution), and identifying a presence of a physiological event in the target volume of interest based on the determined intensity population distribution spread. In one embodiment, the processor is configured for quantifying the spread of the intensity population distribution, and identifying the presence of the physiological event in the target volume of interest only if the quantified intensity population distribution spread is greater than a reference threshold. In this case, the processor may be configured for determining a magnitude of the physiological event based on the quantified intensity population distribution spread. In one embodiment, the target volume of interest may comprise brain tissue, in which case, the physiological event may be a fast-optical signal, and the processor may be configured for determining neural activity within the target volume of interest based on the identified fast-optical signal.

In accordance with a second aspect of the present inventions, a non-invasive optical detection method comprises delivering sample light into a target volume of interest of an anatomical structure, whereby the sample light is scattered by the target volume of interest, resulting in a sample light pattern that exits the anatomical structure. The method further comprises combining reference light with the sample light pattern to generate at least one interference light pattern (e.g., a speckle light pattern), each having spatial components (e.g., speckle grains). The method further comprises detecting intensities of the spatial components of each of the at least one interference light pattern during a measurement period. The sample light may comprise at least one pulse (e.g., a single pulse or a plurality of pulses) delivered into the target volume of interest during the measurement period. One method may further comprise shifting the sample light relative to the reference light by a frequency offset, such that the sample light pattern and the reference light are combined using a heterodyning technique. In this case, the measurement period may be equal to an inverse of the frequency offset between the sample light and the reference light.

In another non-invasive optical detection method, the method comprises combining the reference light with the sample light pattern, such that each of the interference light pattern(s) has a time varying interference component that integrates to a first value over the measurement period in the absence of the physiological event in the target volume of interest, and that integrates to a second value greater than the first value over the measured period in the presence of the physiological event.

The first value may be approximately zero, and may be equal to or less than one percent of the absolute integral of the time varying interference component. For example, if the sample light is shifted relative to the reference light by a frequency offset, the sample light may comprise a rectangular pulse, in which case, the product of the frequency offset between the sample light and the reference light and a duration of the rectangular pulse may be equal to one. As another example, the sample light may comprise two identical pulses (e.g., two Gaussian pulses or even two arbitrarily-shaped pulses) separated from each other by the inverse of two times the frequency offset between the sample light and the reference light. An optional method further comprises using feedback control to periodically modify one or more of a waveform shape of the sample light and the frequency offset between the sample light and the reference light to minimize the first value.

The method further comprises analyzing an intensity population distribution of a function of the detected spatial component intensities of the at least one interference light pattern. In the case of a single interference light pattern, the function may be an identify function, and in the case of two interference light patterns (which may have a phase difference of 180 degrees), the function may be a subtraction function.

The method further comprises determining a spread of the analyzed intensity population distribution (e.g., computing a standard deviation of the intensity population distribution), and identifying a presence of a physiological event in the target volume of interest based on the determined intensity population distribution spread. One method further comprises quantifying the spread of the intensity population distribution, wherein the presence of the physiological event in the target volume of interest is identified only if the quantified intensity population distribution spread is greater than a reference threshold. The method may further comprise determining a magnitude of the physiological event based on the quantified intensity population distribution spread. In one method, the target volume of interest comprises brain tissue, in which case, the physiological event may be a fast-optical signal. The method may further comprise determining neural activity within the target volume of interest based on the identified fast-optical signal.

In accordance with a third aspect of the present inventions, a non-invasive optical detection system comprises an interferometer configured for delivering sample light into a target volume of interest within an anatomical structure, whereby the sample light is scattered by the target volume of interest, resulting in a sample light pattern that exits the anatomical structure. The interferometer is further configured for combining reference light with the sample light pattern to generate at least one interference light pattern (e.g., a speckle light pattern), each having spatial components (e.g., speckle grains). In one embodiment, the interferometer may be further configured for shifting the sample light relative to the reference light by a frequency offset, such that the sample light pattern and the reference light are combined using a heterodyning technique. In this case, the measurement period may be equal to an inverse of the frequency offset between the sample light and the reference light. In another embodiment, the interferometer comprises a light source configured for generating source light, and a beam splitter configured for splitting the source light into the sample light and the reference light.

Significantly, each of the interference light pattern(s) has a time varying interference component that integrates to a first value over a measurement period in the absence of the physiological event in the target volume of interest, and that integrates to a second value greater than the first value over the measured period in the presence of the physiological event.

The first value may be approximately zero, and may be equal to or less than one percent of the absolute integral of the time varying interference component. For example, if the interferometer is configured for shifting the sample light relative to the reference light by a frequency offset, the sample light may comprise a rectangular pulse, in which case, the product of the frequency offset between the sample light and the reference light and a duration of the rectangular pulse may be equal to one. As another example, the sample light may comprise two identical pulses (e.g., two Gaussian pulses or even two arbitrarily-shaped pulses) separated from each other by the inverse of two times the frequency offset between the sample light and the reference light. In an optional embodiment, the optical detection system comprises a controller configured for using feedback control to periodically modify one or more of a waveform shape of the sample light and the frequency offset between the sample light and the reference light to minimize the first value.

The non-invasive optical detection system further comprises at least one array of detectors respectively configured for detecting intensities of spatial components (e.g., speckle grains) of the interference light pattern(s) during the measurement period. In one embodiment, a single interference light pattern is generated, in which case, a single array of detectors is configured for detecting intensities of the spatial components of the interference light pattern(s). In another embodiment, two interference light patterns are generated, in which case, two arrays of detectors are configured for respectively detecting intensities of the spatial components of the two interference light patterns. The sample light may comprise at least one pulse (e.g., a single pulse or a plurality of pulses) delivered into the target volume of interest during the measurement period.

The non-invasive optical detection system further comprises a processor configured for analyzing a function of the detected spatial component intensities of the interference light pattern(s). In the case of a single interference light pattern, the function may be an identify function, and in the case of two interference light patterns (which may have a phase difference of 180 degrees), the function may be a subtraction function. The processor is further configured for identifying a presence of a physiological event in the target volume of interest based on the analysis. In one embodiment, the target volume of interest may comprise brain tissue, in which case, the physiological event may be a fast-optical signal, and the processor may be configured for determining neural activity within the target volume of interest based on the identified fast-optical signal.

In accordance with a fourth aspect of the present inventions, a non-invasive optical detection method comprises delivering sample light into a target volume of interest within an anatomical structure, whereby the sample light is scattered by the target volume of interest, resulting in a sample light pattern that exits the anatomical structure. The method further comprises combining reference light with the sample light pattern to generate at least one interference light pattern (e.g., a speckle light pattern), each having spatial components (e.g., speckle grains). One method may further comprise shifting the sample light relative to the reference light by a frequency offset, such that the sample light pattern and the reference light are combined using a heterodyning technique. In this case, the measurement period may be equal to an inverse of the frequency offset between the sample light and the reference light.

Significantly, the reference light and sample light pattern are combined, such that each of the interference light pattern(s) has a time varying interference component that integrates to a first value over the measurement period in the absence of the physiological event in the target volume of interest, and that integrates to a second value greater than the first value over the measured period in the presence of the physiological event.

The first value may be approximately zero, and may be equal to or less than one percent of the absolute integral of the time varying interference component. For example, the sample light may comprise a rectangular pulse, in which case, the product of the frequency offset between the sample light and the reference light and a duration of the rectangular pulse may be equal to one. As another example, the sample light may comprise two identical pulses (e.g., two Gaussian pulses or even two arbitrarily-shaped pulses) separated from each other by the inverse of two times the frequency offset between the sample light and the reference light. An optional method further comprises using feedback control to periodically modify one or more of a waveform shape of the sample light and the frequency offset between the sample light and the reference light to minimize the first value.

The method further comprises detecting intensities of spatial components (e.g., speckle grains) of each of the at least one interference light pattern during a measurement period. The sample light may comprise at least one pulse (e.g., a single pulse or a plurality of pulses) delivered into the target volume of interest during the measurement period.

The method further comprises analyzing a function of the detected spatial component intensities of the at least one interference light pattern. In the case of a single interference light pattern, the function may be an identify function, and in the case of two interference light patterns (which may have a phase difference of 180 degrees), the function may be a subtraction function. The method further comprises identifying a presence of a physiological event in the target volume of interest based on the analyzed function. In one method, the target volume of interest comprises brain tissue, in which case, the physiological event may be a fast-optical signal. The method may further comprise determining neural activity within the target volume of interest based on the identified fast-optical signal.

Other and further aspects and features of the invention will be evident from the following detailed description, which are intended to illustrate, not limit, the invention.

BRIEF DESCRIPTION OF THE DRAWINGS

The drawings illustrate the design and utility of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 2a is a scatter plot of an exemplary speckle light pattern simulated by combining a sample light pattern and reference light;

FIG. 2b is a speckle intensity histogram of the exemplary speckle light pattern of FIG. 2a;

FIG. 20a is a timing diagram illustrating a relationship between double arbitrarily-shaped light pulses and a frequency offset between the sample light and the reference light that can be used in the non-invasive diffusive optical detection system of FIG. 8 to generate a temporal beat component that integrates to zero;

FIG. 20b is a timing diagram illustrating a relationship between double Gaussian-shaped light pulses and a frequency offset between the sample light and the reference light that can be used in the non-invasive diffusive optical detection system of FIG. 8 to generate a temporal beat component that integrates to zero;

DETAILED DESCRIPTION OF THE EMBODIMENTS

Figure 8:
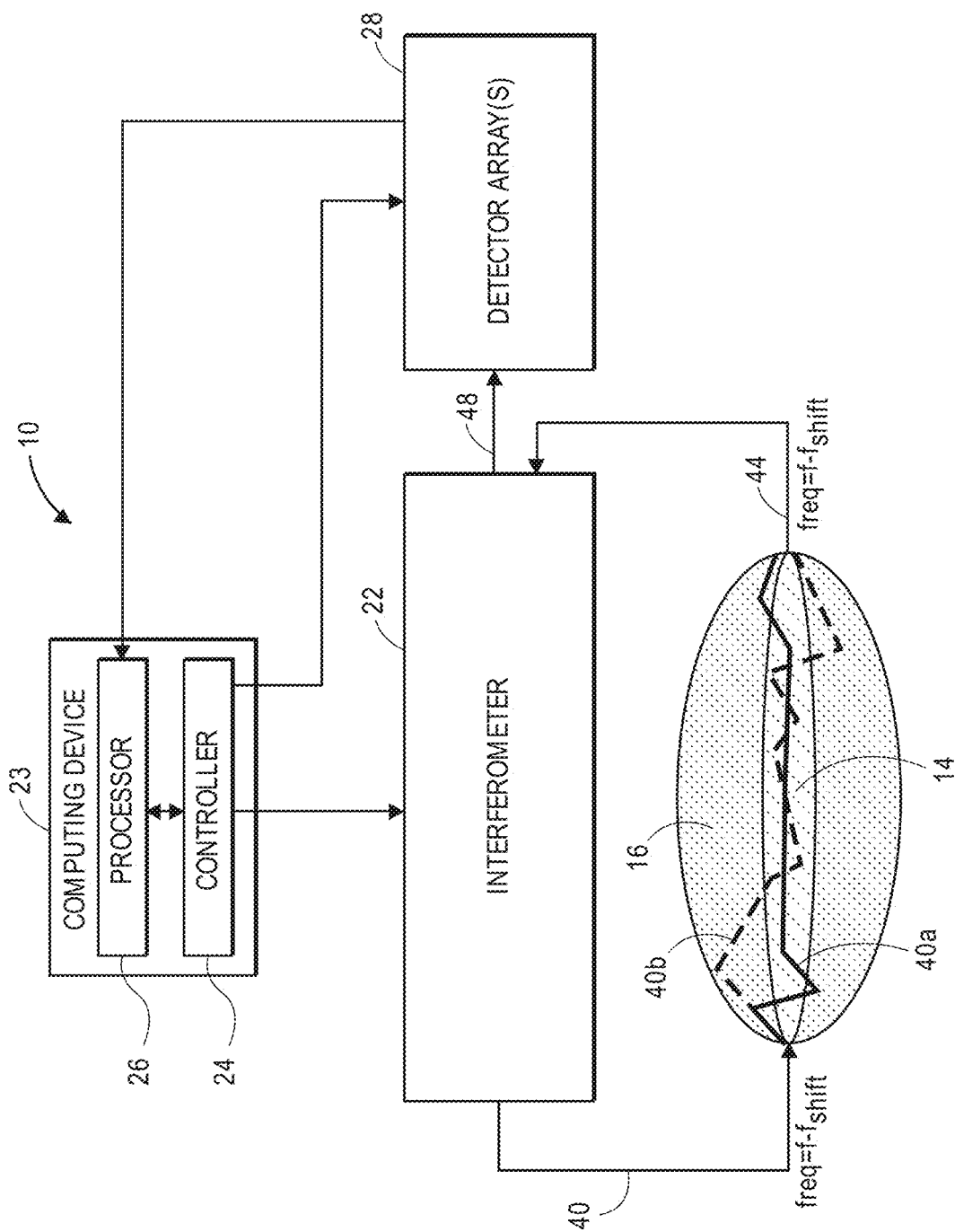
FIG. 8 is a block diagram of a diffusive non-invasive optical detection system constructed in accordance with one embodiment of the present inventions.
Figure 24:
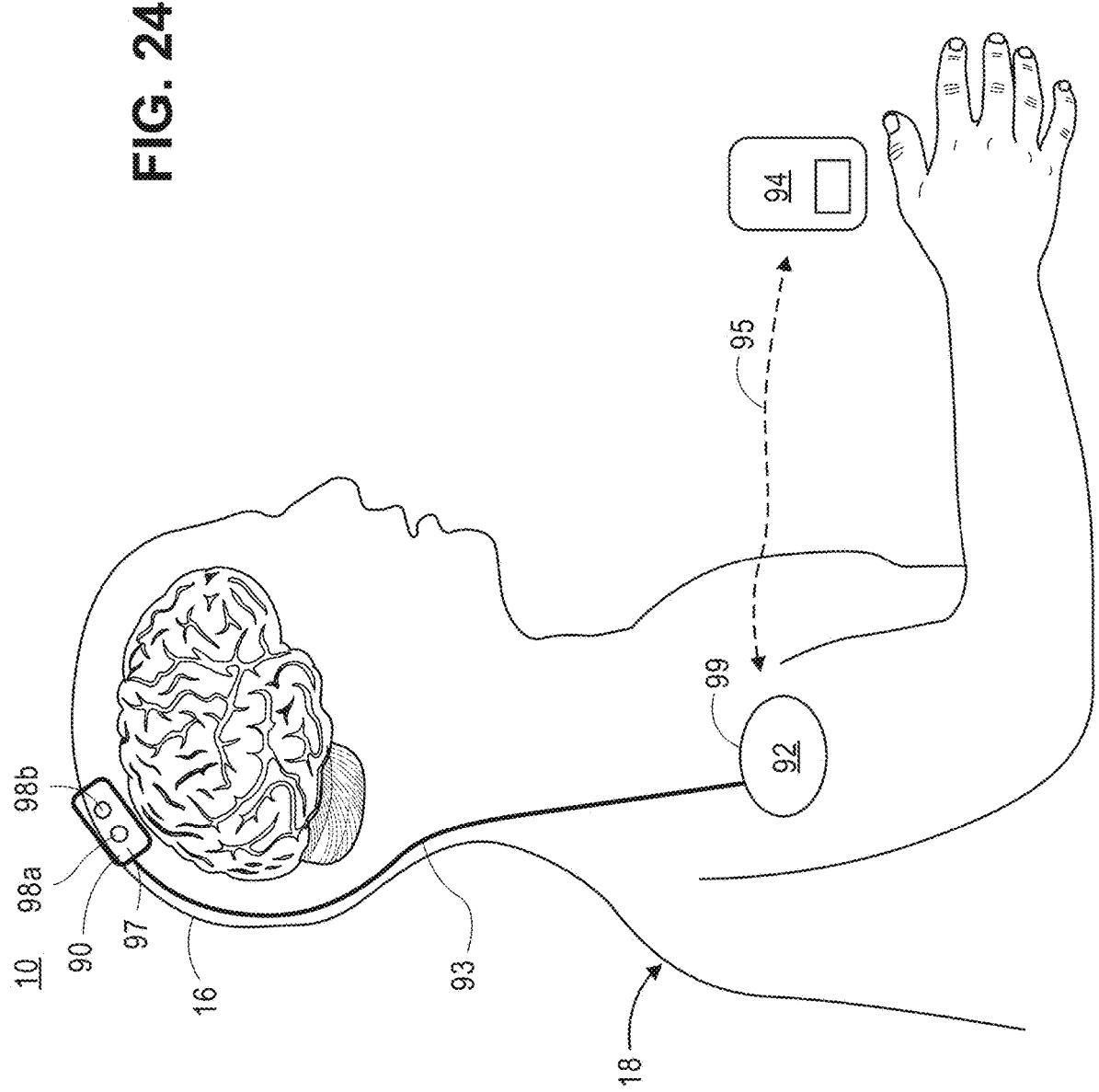
FIG. 24 is a plan view of wearable and unwearable units in which the non-invasive diffusive optical detection system of FIG. 8 may be embodied.

The diffusive optical detection system 10 described herein, and as shown in FIGS. 8 and 24, is designed to non-invasively detect a physiological event in a target volume of interest within an anatomical structure. In the illustrated embodiments, the anatomical structure is the intact head of a user, including the scalp, skull, and brain, with the target volume of interest comprising brain tissue. For exemplary purposes, the non-invasive diffusive optical detection system 10 is described herein as being used to measure and/or detect brain activity within brain tissue. However, such systems can be used to measure and/or detect other anatomical parts of a human body, animal body and/or biological tissue.

In a practical implementation, the non-invasive diffusive optical detection system 10 will acquire data from multiple volumes of interest spatially separated from each other within biological tissue. A "volume of interest" may be defined as a contiguous sub-volume of space (e.g., a banana-shaped volume of biological tissue) within the anatomical structure. For purposes of brevity, the diffusive optical detection system 10 is primarily described herein as acquiring one data measurement (i.e., data representative of the existence of a physiological event within the target volume of interest), e.g., by using a single paired source-detector arrangement, although it should be understood that the diffusive optical detection system 10 may be capable of acquiring more than one data measurement from the target volume of interest of the anatomical structure, e.g., by using a multiple paired source-detector arrangement or by moving the single paired source-detector arrangement between the acquisition of data measurements, or by having multiple detectors for a single source, as will be described herein with reference to the illustrated embodiments and as depicted in the accompanying figures.

In the illustrated embodiments, the non-invasive diffusive optical detection system 10 detects and/or measures neurological events that result in fast-optical signals (i.e., perturbations in the optical properties of neural tissue caused by mechanisms related to the depolarization of neural tissue, including, but not limited to, cell swelling, cell volume change, changes in membrane potential, changes in membrane geometry, ion redistribution, birefringence changes, etc.), although in alternative embodiments, the non-invasive diffusive optical detection system 10 may be tuned to detect and/or measure other physiological events that cause a change in an optical property of the target volume of interest, e.g., Doppler shift due to moving blood flow, changes in blood volume, metabolism variations such a blood oxygen changes. Information and acquired neural data related to the detected physiological event may be used internally within the diffusive optical detection system 10 to adjust the detection or measurement parameters of the system, such as increasing or decreasing the strength of the light source and/or data compression and/or analysis, such a Fast Fourier Transform (FFT) and/or statistical analysis; or may be transmitted to external programmable devices for use therein, e.g., medical devices, entertainment devices, neuromodulation stimulation devices, lie detection devices, alarm systems, educational games, brain interface devices, etc.

The non-invasive diffusive optical detection system 10, in effect, is a "balanced" optical holography system that is highly sensitive to minute perturbations in the optical properties of the target volume of interest (including, but not limited to, absorption, scattering, path-length, particle displacement, and frequency changes (like Doppler or Raman-Nath). The diffusive optical detection system 10 accomplishes this by combining sample light propagating through the anatomical structure with reference light using a heterodyning technique to create at least one interference light pattern having a time-varying component (a "temporal beat component") that, due to the lack of a phase change in the path length of the scattered sample light (as a result of the absence of fast-optical signals in the target volume of interest), integrates to a first value (preferably a zero value), but that, due to a phase change in the path length of the scattered sample light (as a result of the presence of fast-optical signals in the target volume of interest), integrates to second non-zero value greater than the first value in an absolute sense.

Figure 1:
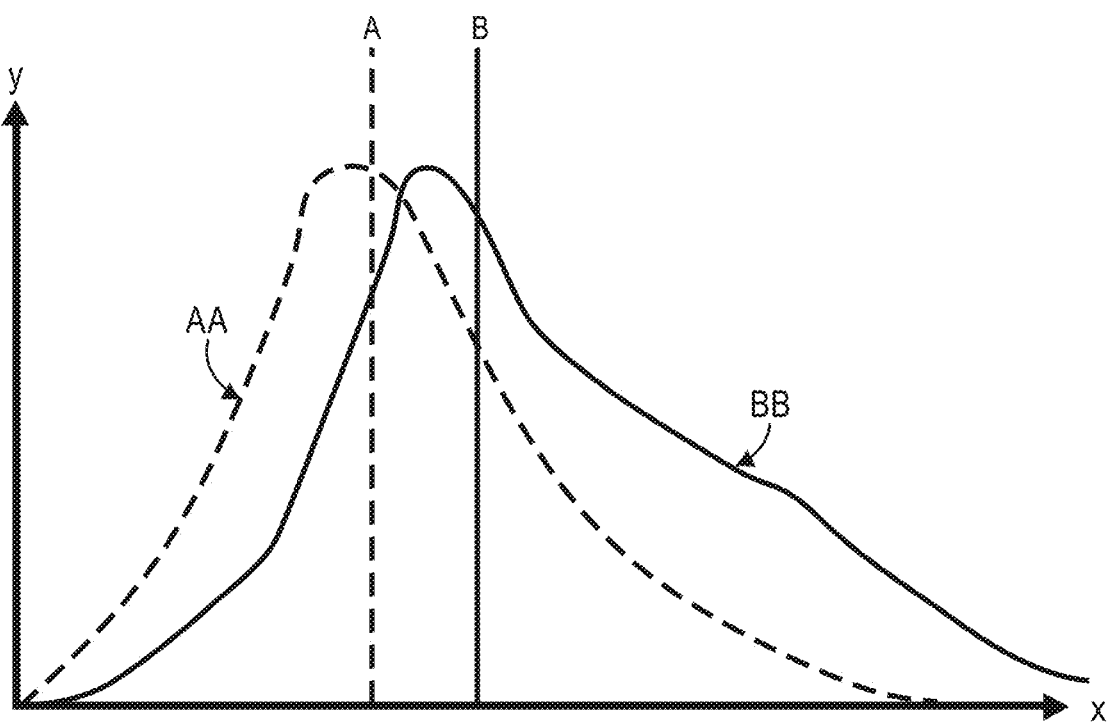
FIG. 1 is a diagram illustrating the effect of fast-optical signals on the phases of exemplary optical waveforms.

Referring first to FIG. 1, it can be seen that the changes in optical path length due to the presence of fast-optical signals in biological tissue presents itself as a wavefront shift (delay or advancement) that can be detected as a change in optical phase at a signal detector. In particular, a first AA dash line showing exemplary temporal point-spread function of diffusive light through biological tissue in the absence of a fast-optical signal, and a second BB solid line showing exemplary temporal point-spread function of diffusive light through the biological tissue in the presence of a fast-optical signal (both AA and BB are plotted as a fraction of photons in the y-direction and as a function of time in the x-direction (typically on the order of picoseconds or nanoseconds)). As exemplified by the shift of the second BB solid line showing exemplary temporal point-spread function further in time than the first AA dash line showing exemplary temporal point-spread function, the average path length B of the diffusive light propagating through the biological tissue in the presence of the fast-optical signal has been increased relative to the average path length A of the diffusive light propagating through the biological tissue in the absence of the fast-optical signal. The diffusive optical detection systems described herein are designed and configured to detect the slightest increase in the average path length, for example B, of the diffusive light due to the presence of a fast-optical signal in the target volume of interest within the biological tissue.

Significantly, the inventors have discovered that a diffusive optical detection system can be "balanced" to minimize the variability in the static background signal close to the theoretical minimum shot noise, which is a fundamental variability in the measured light field resulting from the quantum nature of light. In the resulting measurements, such that the spread of the intensity population distribution of a function of the spatial components the interference light pattern or interference light patterns generated by the interference of a sample light pattern and reference light, varies greatly in accordance with a perturbation-induced change in the integration value of a time varying interference component of each of the interference light pattern(s). As a result, such "balanced" diffusive optical system is highly sensitive to changes in the optical phase of the wavefront, and specifically, ones on certain timescales. Such function of the spatial components of the interference light pattern(s) may be, e.g., an identity function in the case of a single interference light pattern generated by the combination of the sample light pattern and reference light, or a subtraction function in the cases of two interference light patterns simultaneously generated by the combination of the sample light pattern and reference light. Accordingly, the diffusive optical detection systems described herein are capable of detecting and/or measuring the presence of fast-optical signals within a target volume of interest within biological tissue by measuring or detecting the intensity population distribution of the function of spatial components of the interference light pattern(s) across an array or array(s) of detectors, and determining a characteristic (and in this case, the spread) of the intensity population distribution amongst the detectors.

In general, it has been determined that the spread (or width) of the intensity population distribution of an interference light pattern significantly increases in accordance with magnitude of a fast-optical signal in neural tissue through which the sample light propagates. As will be demonstrated in further detail below, due to the "balanced" nature of the diffusive optical detection systems during a quiescent period (i.e., no fast-optical signals), such diffusive optical system can be "tipped" or become unbalanced in response to minute perturbations in the optical properties of the neural tissue, the spread of the intensity population distribution of the interference light pattern is maximized in the presence of fast-optical signals, such that the spread greatly increases even if the signal-to-noise ratio of the fast-optical signal is relatively low (in essence, a very large signal is generated in response to a very small signal, and in this case, a minute shift in the path length of the sample light). The spread of the intensity population distribution can be quantified (e.g., by computing a standard deviation) and used to objectively identify the presence of a fast-optical signal in the target volume of interest if it is greater than a reference threshold, and perhaps even determine the magnitude of the fast-optical signal based on the quantified intensity population distribution.

Figure 2:
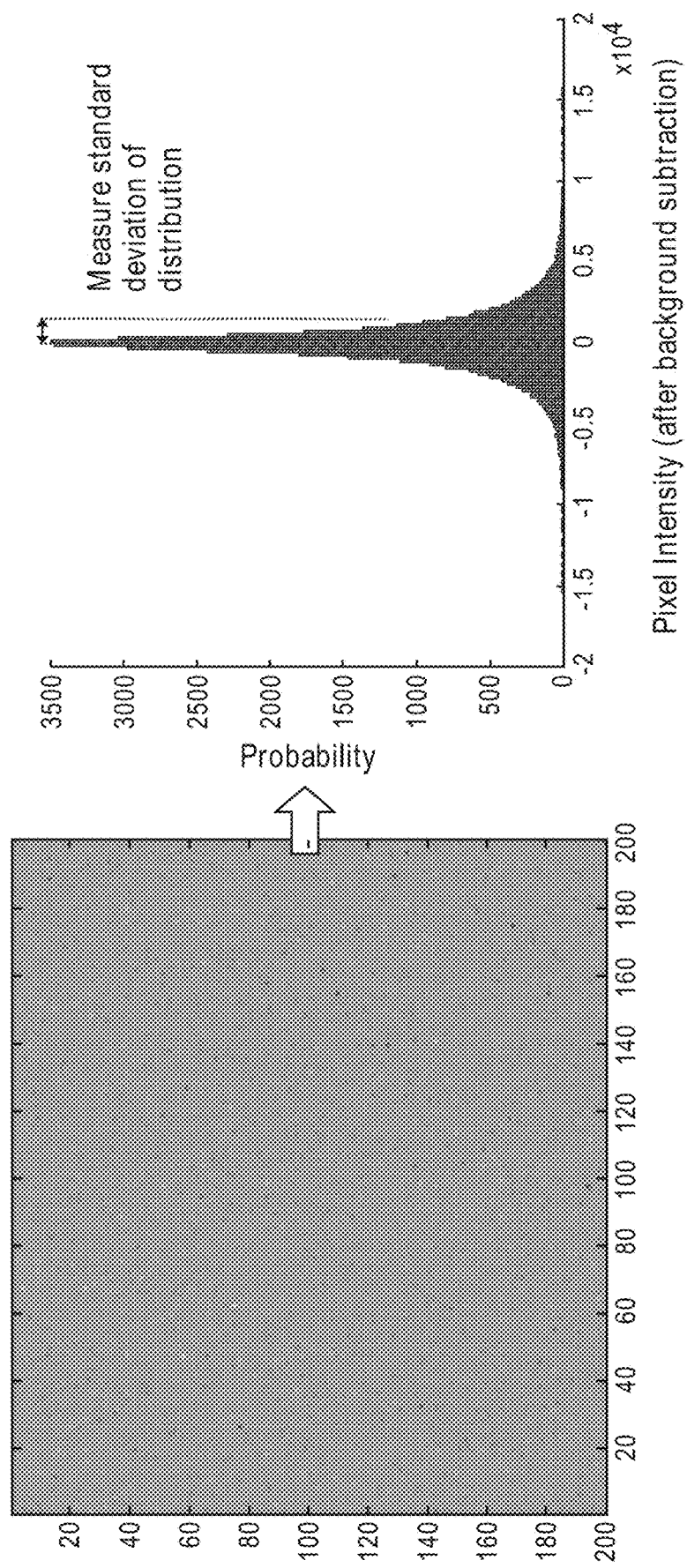

For example, an exemplary speckle pattern, shown in FIG. 2a, may be detected by a conventional digital camera comprising a 200×200 array of detectors (or pixels), such that an intensity population distribution represented by a speckle intensity histogram, shown in FIG. 2b, can be obtained. In this example, the intensity population distribution was simulated using MATLAB, assuming the following four parameters: (1) shot noise modeled by a Poisson distribution with a mean equal to the integral of each pixel; (2) a frequency shift between the sample light and the reference light of 2 MHz; (3) the sample light and the reference light having rectangular pulse waveforms and amplitudes that result in 20,000 photons per pixel for each measurement after integration; and (4) that integration performed with rectangular sampling at a step size of 1 nanosecond for 500 nanoseconds. As described below, these four parameters are also assumed in the MATLB simulations represented in FIGS. 3-7.

FIG. 2a represents a scatter plot of speckle intensity values detected by the detector array, with the x-axis representing the detectors in one axis of the array, and the y-axis representing the detectors in the other axis of the array. FIG. 2b represents a speckle intensity histogram plot (after subtraction of the static background signal), with the x-axis of the speckle intensity representing the number of photons per pixel from $-2\times10^4$ to $+2\times10^4$ (normalized to the median value of 0), and the y-axis representing the number (or count) of pixels that detect each particular number or range of photons. In the exemplary embodiment, the spread of the intensity population distribution may be characterized as a standard deviation (although other measures, such as variance, can be used to characterize the spread of the intensity population distribution), with a low standard deviation indicative of a relatively narrow intensity population distribution, and a high standard deviation indicative of a relatively wide intensity population distribution. In the exemplary case, the median value of the speckle intensity histogram is 3500 pixels, and the standard deviation is $0.15 \times 10^4$ photons per pixel.

Significantly, the time-varying component of the speckle light pattern generated by the diffusive optical detection system described herein integrates to zero in the absence of a physiological event in the neural tissue that would otherwise cause path length changes in sample light that are varying on a timescale selected by a frequency offset $f_{shift}$ (described in further detail below with reference to FIG. 11a), such that the standard deviation of the intensity population distribution of the speckle light pattern is minimized under this condition. Thus, the notion that the speckle light pattern is changing during measurement is key. In essence, the diffusive optical detection system integrates out signal components that are static (i.e., the static background signal) and highlights the time-varying signal components at a timescale that can be selected much quicker than hemodynamic signals, and in fact, may be arbitrarily selected to any timescale using the frequency offset $f_{shift}$. Thus, such diffusive optical detection system can be characterized as being balanced, and is thus highly sensitive to minute time-varying phase changes in the path length of sample light, and thus, highly sensitive to fast-optical signals with low signal-to-noise ratios. That is, in the presence of fast-optical signals within the target volume of interest, such diffusive optical detection system quickly becomes unbalanced, generating a speckle light pattern with an intensity population distribution having a standard deviation that rapidly widens under this condition. Thus, such a diffusive optical detection system has a relatively high temporal resolution in that it is highly sensitive to fast-optical signals, even those having a relatively low signal-to-noise ratio. As a result, the number of measurements needed for such diffusive optical detection system to detect a fast-optical signal is minimized, and perhaps even reduced to one measurement to detect a fast-optical signal.

Figure 3:
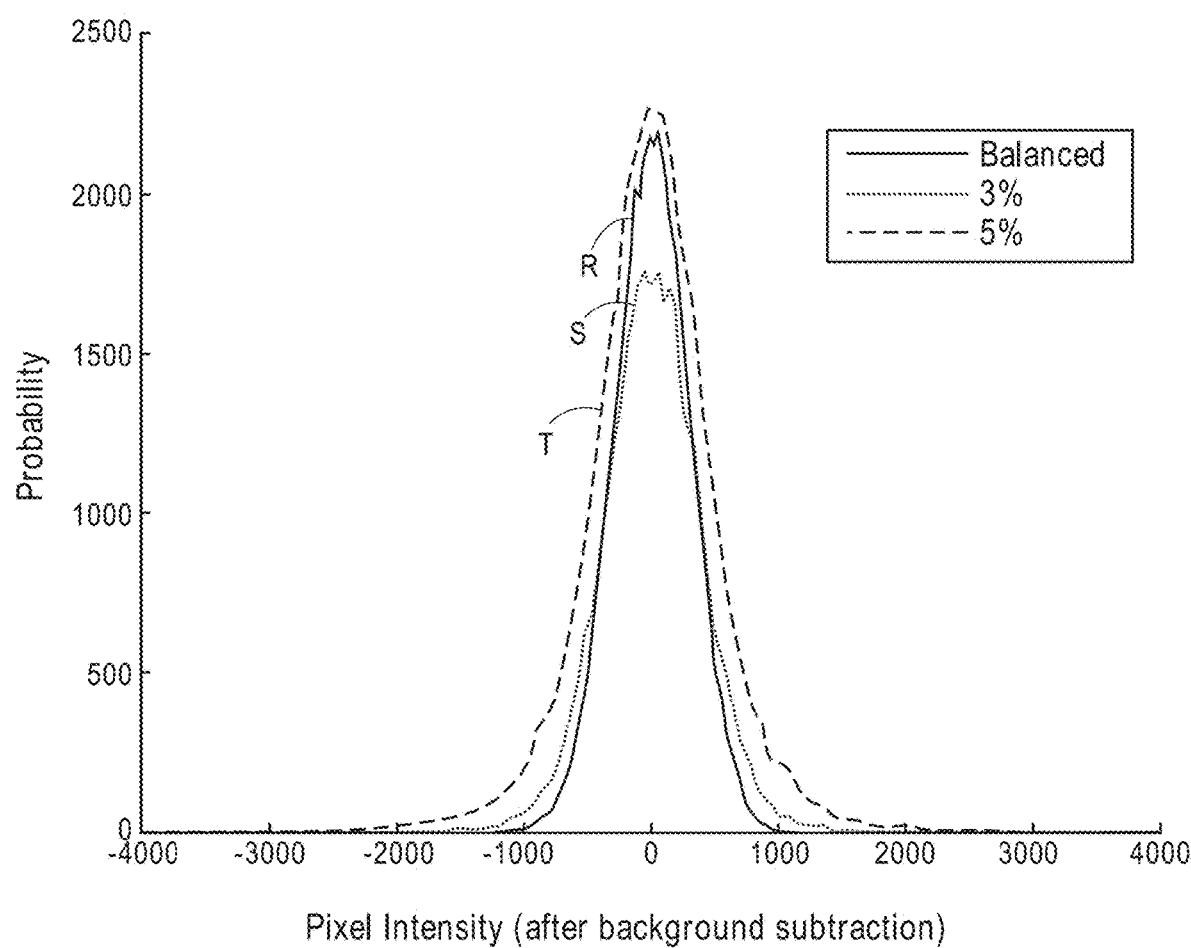
FIG. 3 is a diagram of three exemplary intensity population distributions generated from the exemplary speckle light pattern of FIG. 2a, wherein the intensity population distributions are associated with three phase shift percentages in the optical path length of the sample light in tissue.

Referring to FIG. 3, three exemplary intensity population distributions (normalized) were simulated with MATLAB assuming the same four parameters set forth above, and further assuming a single conventional charge-coupled device (CCD) camera. The first exemplary intensity population distribution, as shown by solid line R, assumes a balanced case where there is no mean phase shift in the path length of the sample light; the second exemplary intensity population distribution, as shown by dash-line S, assumes an unbalanced case where there is a three percent phase shift in the path length (equivalent to a 10.8 degree change in phase angle) of the sample light occurring during the oscillation cycle; and the third exemplary intensity population distribution, as shown by the dash-line T, assumes an unbalanced case where there is a five percent phase shift in the path length (equivalent to a eighteen-degree change in phase angle) of the sample light. As shown in FIG. 3, the exemplary intensity population distributions, S and T, simulated in the unbalanced cases get progressively wider than the exemplary intensity population distribution simulated in the balanced case R. Thus, it can be demonstrated that the intensity population distribution of interference light patterns generated by the diffusive optical system described herein can be quantified and used to, not only determine the present of a fast-optical signal within a target volume of interest, but determine the intensity level of the fast-optical signal within the volume of interest.

Figure 4:
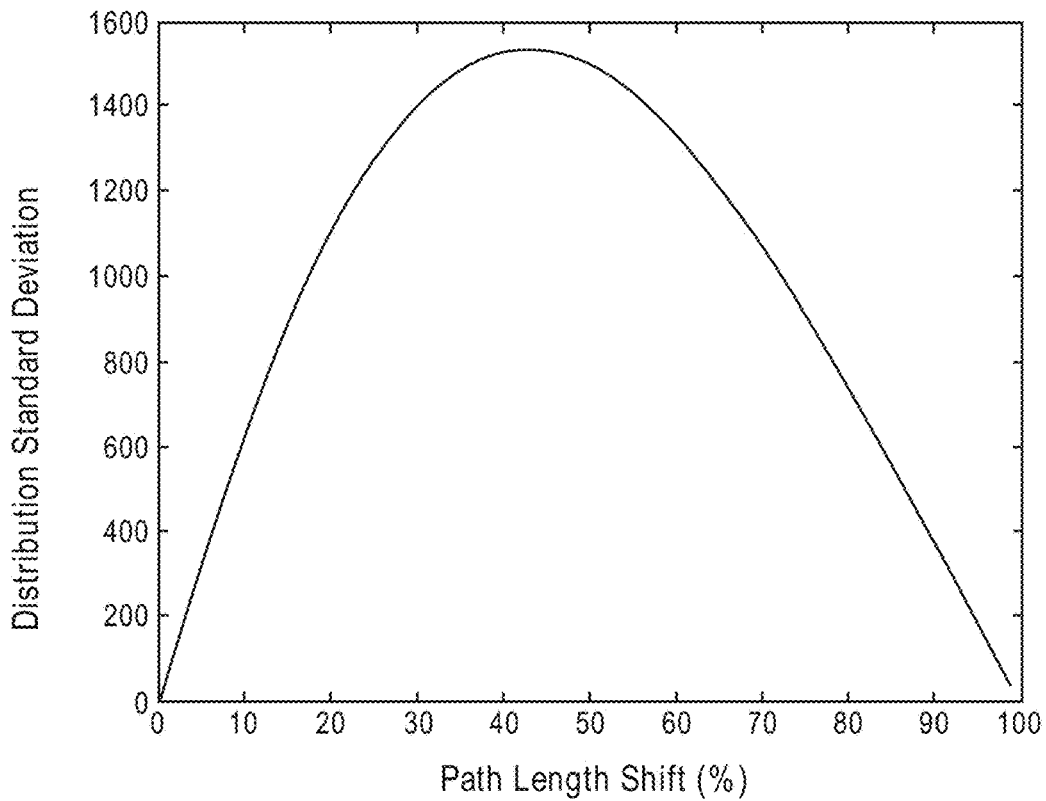
FIG. 4 is a diagram of the standard deviation of an exemplary intensity population distribution plotted as a function of phase change percentage (0-100 percent) in the optical path length of the sample light in tissue, wherein no shot noise is assumed.

Referring now to FIG. 4, an intensity population distribution was simulated with MATLAB over a range of mean fractional phase shifts in the path length of the sample from zero percent (balanced case) to one hundred percent in one percent steps, assuming the same four parameters set forth above. It should be appreciated that the phase shift percentages illustrated in FIG. 4, and described throughout this specification, refers to the fractional phase change of a full sinusoidal cycle of the time-varying interference component (i.e., a temporal beat component) caused by the change in the path length of the sample light. Thus, the fractional phase shift depends on the length of the sinusoidal cycle of the temporal beat component and on how quickly the path length shift of the sample light arises.

For instance, assuming a path length delay of 0 picoseconds at time zero, a path length delay of 10 picoseconds after 100 milliseconds, a linear path length shift between 0 picoseconds and 100 milliseconds, and that the time-varying interference component beats at 1 MHz (i.e., the temporal beat component has a period of 1 microsecond), then the path length delay at 100 milliseconds will be ((10 picoseconds delay*speed of light)/100 milliseconds rise time)*(1 microsecond cycle time)=30 nanometers. If it is further assumed that the wavelength of the sample light is 700 nanometers, then the fractional path length delay will be equal to 30 nanometers/700 nanometers=4.2%. If it is instead assumed that the time-varying interference component beats at 10 MHz (i.e., the temporal beat component has a period of 0.1 microseconds), then the path length delay at 100 microseconds will be ((10 picoseconds delay*speed of light)/100 milliseconds rise time)*(0.1 microsecond cycle time)=3 nanometers. In this case, the fractional path length delay will be equal to 3 nanometers/700 nanometers=0.42%. If it is assumed that the time-varying interference component beats at 20 KHz (i.e., the temporal beat component has a period of 50 microseconds), then the path length delay at 100 microseconds will be ((10 picoseconds delay*speed of light)/100 milliseconds rise time)*(50 microseconds cycle time)=1500 nanometers. In this case, the fractional path length delay will be equal to 1500 nanometers/700 nanometers=210%.

However, this "wrap around" effect is undesirable as it presents a difficulty in ascertaining the fractional path length shift beyond a half-cycle of the interference beat component. Thus, it is preferred the beat frequency of the time-varying interference component be selected (by selecting the frequency offset $f_{shift}$ discussed in further detail below, FIGS. 11a-11b and 12), such that, given the physiological event to which the diffusive optical detection system is tuned, the range of anticipated fractional path length shifts be maximized without exceeding 50%. In essence, the beat frequency of the time-varying interference component has a "sweet spot" relative to the physiological event to be detected by the diffusive optical detection system. In the above example, which roughly estimates path length delays in sample light caused by fast-optical signals, the "sweet spot" for the time-varying interference component may be 100 KHz.

Referring still to FIG. 4, when no shot noise is assumed in this simulation, the standard deviation of the intensity population distribution increases from zero when there is no mean phase shift in the path length of the sample light to a maximum of around 1550 when there is a fifty percent phase shift in the path length (equivalent to a one hundred eighty-degree change in phase angle) of the sample light, and then decreases back to zero when there is a one hundred percent phase shift in the path length (equivalent to a three hundred sixty-degree change in phase angle) of the sample light. Thus, it can be seen that, under optimal conditions, the standard deviation of the intensity population distribution significantly varies over the full range of phase angles in the path length of the sample light.

However, even with introduction of shot noise in the simulation, it can be demonstrated that the intensity population distribution of an interference light pattern significantly varies in accordance with a change in the phase angles due to the time-varying average path length of the sample light. For example, with reference to FIG. 5, an intensity population distribution was simulated with MATLAB over a range of mean phase shift percentages in the path length of the sample light from zero percent (balanced case) to nine percent in one percent steps (as shown along x-axis), assuming the same four parameters set forth above. In this simulation, shot noise is assumed, such that the standard deviation of the intensity population distribution quickly increases from around 141 (shot noise equal to square root of the product of the sample light and the reference light) when there is no mean phase shift in the path length of the sample light, to 600 when there is a nine percent phase shift in the path length (equivalent to around a thirty-two-degree change in phase angle) of the sample light.

Figure 5:
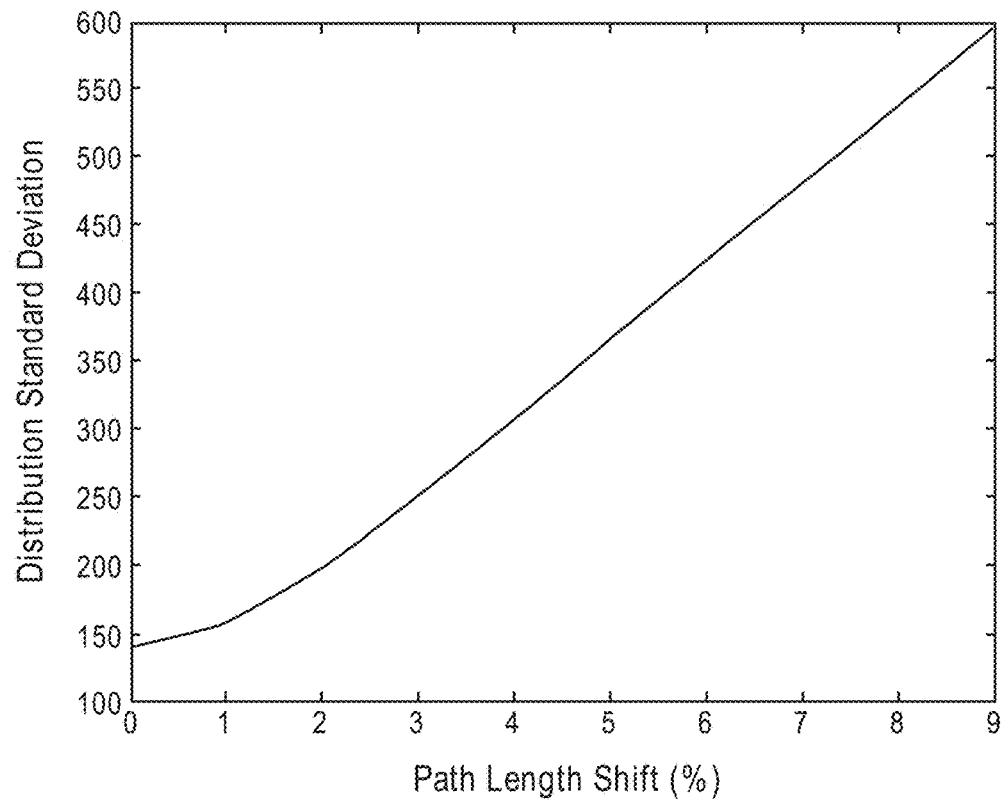
FIG. 5 is a diagram of the standard deviation of an exemplary intensity population distribution plotted as a function of phase change percentage (0-9 percent) in the optical path length of the sample light in tissue, wherein shot noise is assumed.
Figure 6:
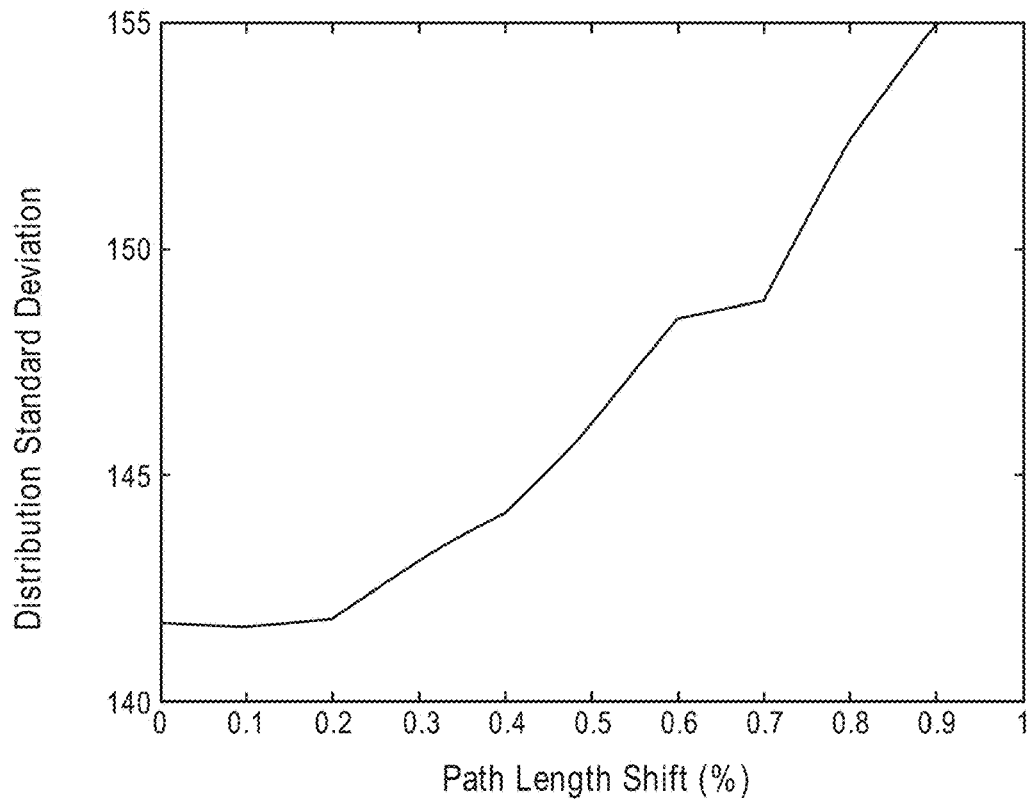
FIG. 6 is a diagram of the standard deviation of an exemplary intensity population distribution plotted as a function of phase change percentage (0-0.9 percent) in the optical path length of the sample light in tissue, wherein shot noise is assumed.

Referring to FIG. 6, the intensity population distribution simulated in FIG. 5 is shown zoomed in from zero percent (balanced) to 0.9 percent. As shown, the standard deviation of the intensity population distribution quickly increases from around 141 (shot noise equal to square root of the product of the sample light and the reference light) when there is no mean phase shift in the path length of the sample light, to 155 when there is a 0.9 percent phase shift in the path length (equivalent to around a three-degree change in phase angle) of the sample light.

Figure 7:
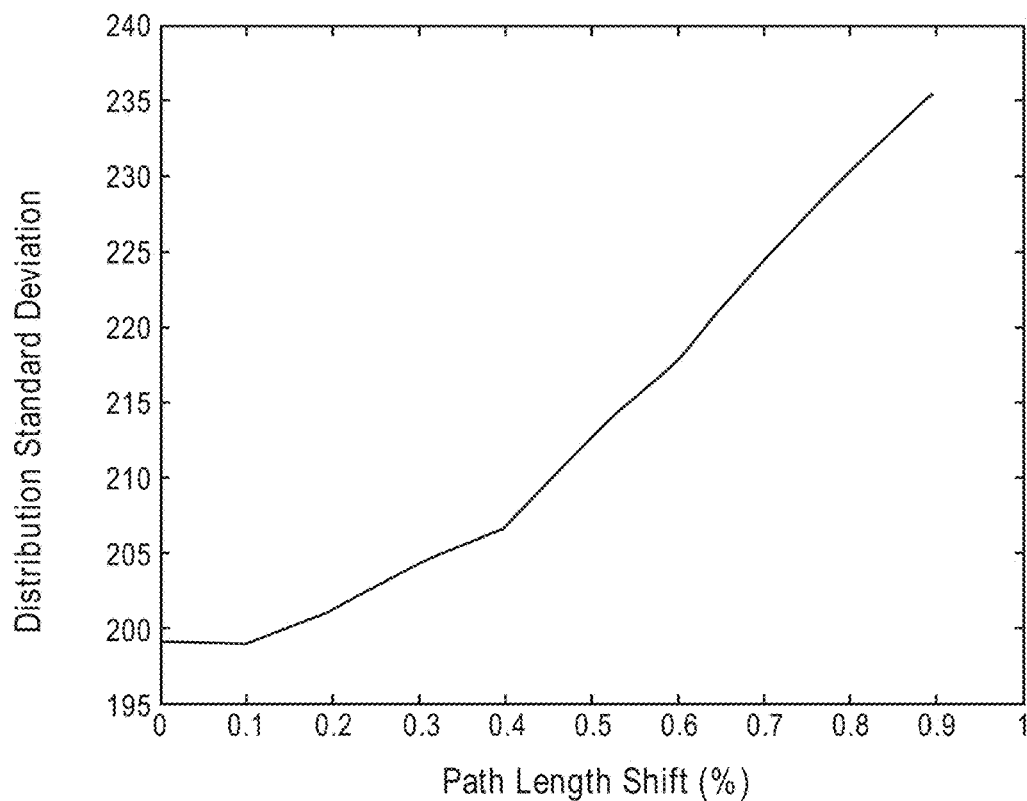
FIG. 7 is a diagram of the standard deviation of an exemplary intensity population distribution plotted as a function of phase change percentage (0-0.9 percent) in the optical path length of the sample light in tissue, assuming shot noise and a larger number of photons used to detect the exemplary speckle light pattern.

Although the standard deviation response appears discretized (rougher) in FIG. 6, the standard deviation response can be made more continuous (smoother) by increasing the number of pixels or the number of photons per pixel. For example, as illustrated in FIG. 7, by doubling the number of photons (40,000 photons per pixel), the standard deviation response has been made more smoothly. However, as also shown, the shot noise increases from 141 to 199 due to the increase in intensity of the sample light and reference light. As a general rule, the standard deviation response will advantageously become more linear as the number of photons and/or the number of pixels increases.

As discussed above, the non-invasive diffusive optical detection system described herein may be "tuned" to detect fast-optical signals (as opposed to, e.g., slower hemodynamic signals) by adjusting a frequency offset $f_{shift}$, and in particular, a frequency shift between the sample light and the reference light, with due regard to the waveform shape of the sample light, such that the resulting temporal beat component of the interference light pattern integrates to zero over a quiescent measurement period, i.e., a measurement period where there are no fast-optical signals in the target volume of interest. Thus, the diffusive optical detection system can be matched to the appropriate time-scale, such that it is selective to fast-optical signals (e.g., on the order of a few milliseconds timescale), but less sensitive to slower timescale changes, such as hemodynamics (e.g., on the order of hundreds of milliseconds to a second timescale). As will be described in further detail below, the diffusive optical detection system may comprise feedback control to ensure that the resulting temporal beat component of the interference light pattern, which may otherwise integrate to a non-zero value in response to dynamic factors other than the presence of fast-optical signals, continues to integrate to zero over the measurement period when the fast-optical signals are absent.

As can be appreciated from the foregoing simulations shown in FIGS. 3-7, it is anticipated that the use of a readily available charged couple device (CCD) camera, or similar commercial type image sensors and detectors such as complementary metal-oxide-semiconductor (CMOS) sensor, photodiode (PD) array, avalanche photodiode (APD) array, single photon avalanche diode (SPAD) detector, time-of-flight (ToF) imaging camera, indium gallium arsenide (InGaAs) sensor, etc., to detect the distribution of intensity values of the interference light pattern will be sufficient for detectability of the presence of fast-optical signals on the scale of roughly greater than 0.1% phase shifts per measurement (or better with higher pixel counts), simply by comparing the distribution spread of the intensity values across all pixels of the camera in a single snapshot during the "balanced" condition (in the absence of a fast-optical signal) to the distribution spread of the intensity values across all pixels of the camera in a single snapshot during the "unbalanced" condition (in the presence of a fast-optical signal). Thus, the camera may be a relatively inexpensive, off-the-shelf camera, which would be advantageous from a system simplicity, speed, and cost perspective. In alternative embodiments, an optical lock-in camera arrangement can be used in place of a conventional CCD camera. One example of such optical arrangement is a camera system comprising a plurality of separate cameras that are optically aligned with each other, such that any given pixel(s) on the cameras have a known one-to-one correspondence with each other. Such optical lock-in camera arrangements are described in U.S. patent application Ser. No. 15/844,370, entitled "Pulsed Ultrasound Modulated Optical Tomography Using Lock-In Camera," which is expressly incorporated herein by reference.

Referring now to FIG. 8, one embodiment of a non-invasive diffusive optical detection system 10 constructed in accordance with the present inventions will now be described. The diffusive optical detection system 10 is configured for non-invasively detecting a fast-optical signal within a target volume of interest 14 (in this case, a volume of brain tissue) of an anatomical structure 16 (in this case, the head of a user). The target volume of interest 14 is defined by the path taken by light between a source-detector pair (described in further detail in FIGS. 25-27). The diffusive optical detection system 10 generally includes an interferometer 22, a computing device or other similar device 23, and at least one detector array 28.

The computing device 23 comprises a controller 24, a processor 26, a memory (not shown), a display (not shown), and an input device (not shown). The computing device 23 can, e.g., be a computer, tablet, mobile device, or any other suitable device for processing information. The computing device 23 can be local to the user or can include components that are non-local to the user. For example, in at least some embodiments, the user may operate a terminal that is connected to a non-local computing device. In other embodiments, the memory can be non-local to the user. The computing device 23 can utilize any suitable processor 26, including one or more hardware processors that may be local to the user or non-local to the user or other components of the computing device 23. The processor 26 is configured to execute instructions provided to the processor 26, as described below.

Any suitable memory can be used for the computing device 23. The memory can be a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal. The term "modulated data signal" can include a signal that has one or more of its characteristics set or changed in such a manner as to encode information, instructions, data, and the like, in the signal. By way of example, communication media includes wired media, such as twisted pair, coaxial cable, fiber optics, wave guides, and other wired media and wireless media, such as acoustic, RF, infrared, and other wireless media.

The display can be any suitable display device, such as a monitor, screen, or the like, and can include a printer. In some embodiments, the display is optional. In some embodiments, the display may be integrated into a single unit with the computing device 23, such as a tablet, smart phone, or smart watch. The input device can be, for example, a keyboard, mouse, touch screen, track ball, joystick, voice recognition system, or any combination thereof, or the like.

Although the controller 24 and processor 26 are described herein as being separate components, it should be appreciated that portions or all functionality of the controller 24 and processor 26 may be performed by a single computing device. Furthermore, although all of the functionality of the controller 24 is described herein as being performed by a single device, and likewise all of the functionality of the processor 26 is described herein as being performed by a single device, such functionality each of the controller 24 and the processor 26 may be distributed amongst several computing devices. Moreover, it should be appreciated that those skill in the art are familiar with the terms "controller" and "processor," and that they may be implemented in software, firmware, hardware, or any suitable combination thereof.

The interferometer 22 is a Mach-Zender type interferometer comprising a sample arm that passes through the user's head 16 and a fixed reference arm that both originate from a light source and terminate in a detector to create at least one interference light pattern 48 (e.g., a single interference light pattern 48 (See FIGS. 18-19) or two phase-modulated interference light patterns 48 (See FIGS. 22-23), as will be described in further detail below. In the illustrated embodiment, each of the interference light pattern(s) 48 takes the form of a speckle light pattern, which can be defined as an intensity pattern produced by the mutual interference of a set of scattered wavefronts. That is, a speckle light pattern results from the interference of many waves, but having different phases and amplitudes, which add together to give a resultant wave whose amplitude, and therefore intensity and phase, varies randomly.

To this end, the interferometer 22 is configured for delivering sample light 40 into the user's head 16, where it scatters diffusively, e.g., through the human skull, into the brain, and back out again, exits as a sample light pattern 44, which is combined with reference light (shown in FIGS. 9a-9d) to create the interference light pattern(s) 48. As it scatters diffusively through the user's head 16, various portions of the sample light 40 will take different paths through the user's head 16. For purposes of brevity, only a first sample light portion 40a traveling along a relatively short path, and a second sample light portion 40b traveling along a relatively longer path, are illustrated, although it should be appreciated that the diffused sample light 40 will travel along many more paths through the head 16. Significantly, the sample light portions 40a, 40b travel through the target volume of interest 14 and exit the head 16 as the sample light pattern 44, which is encoded with any physiological events that change an optical property of the target volume of interest 14. As will be described in further detail below, the interferometer 22, when properly tuned to a specific type of physiological event, and in this case, the presence of a fast-optical signal, is capable of decoding the sample light pattern 44 to detect that physiological event. It should be appreciated that, although not all of the sample light 40 in the sample light pattern 44 passes through the target volume of interest 14, it is only important that at least some of the sample light 40 in the sample light pattern 44 pass through the target volume of interest 14, such that the exiting sample light pattern 44 will be encoded with any physiological events that occur in the target volume of interest 14.

The interferometer 22 shifts the frequency between the sample arm and reference arm by a frequency offset $f_{shift}$, such that the interference light pattern 48 (shown in FIGS. 9a-9d) has a time-varying interference component (i.e., a temporal beat component) having a frequency equal to such frequency offset $f_{shift}$. Thus, the interferometer 22 is configured for combining the sample light pattern 44 exiting the user's head 16 and the reference light 42 using a heterodyning technique by initially shifting the frequency f of the sample light 40 and the reference light 42 relative to each other by the frequency offset $f_{shift}$. For the purposes of this specification, the term "heterodyne or heterodyning technique," when referring to the combination of a sample light pattern 44 and reference light 42, means that the sample light pattern 44 and the reference light 42 have different frequencies when combined to generate at least one interference light pattern having a temporal beat component, which can be detected by the detector array 28 as the signal component during the measurement period, as will be discussed in further detail below.

Figure 9A:
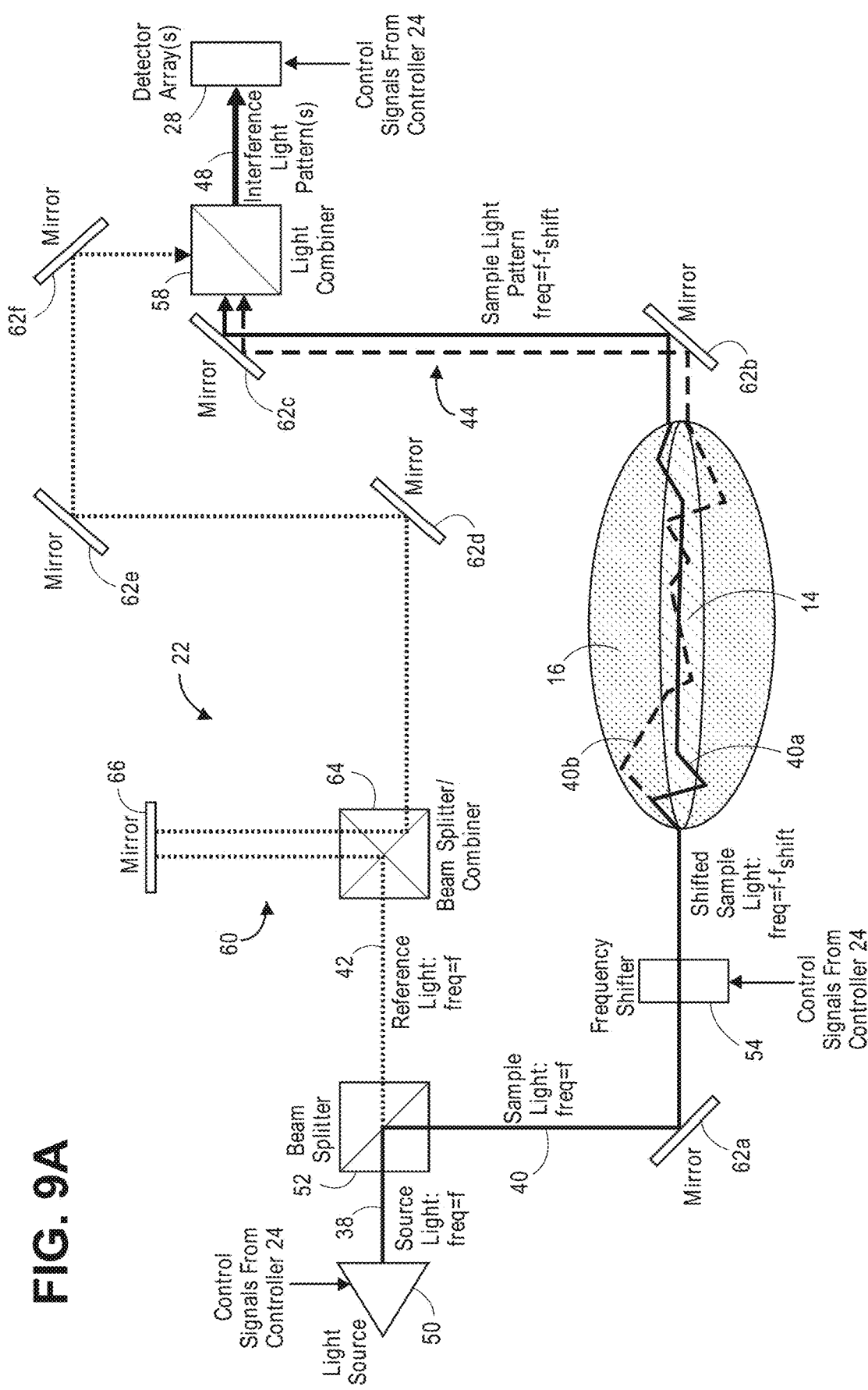
FIG. 9a is a block diagram of one embodiment of an interferometer used in the non-invasive diffusive optical detection system of FIG. 8.
Figure 9B:
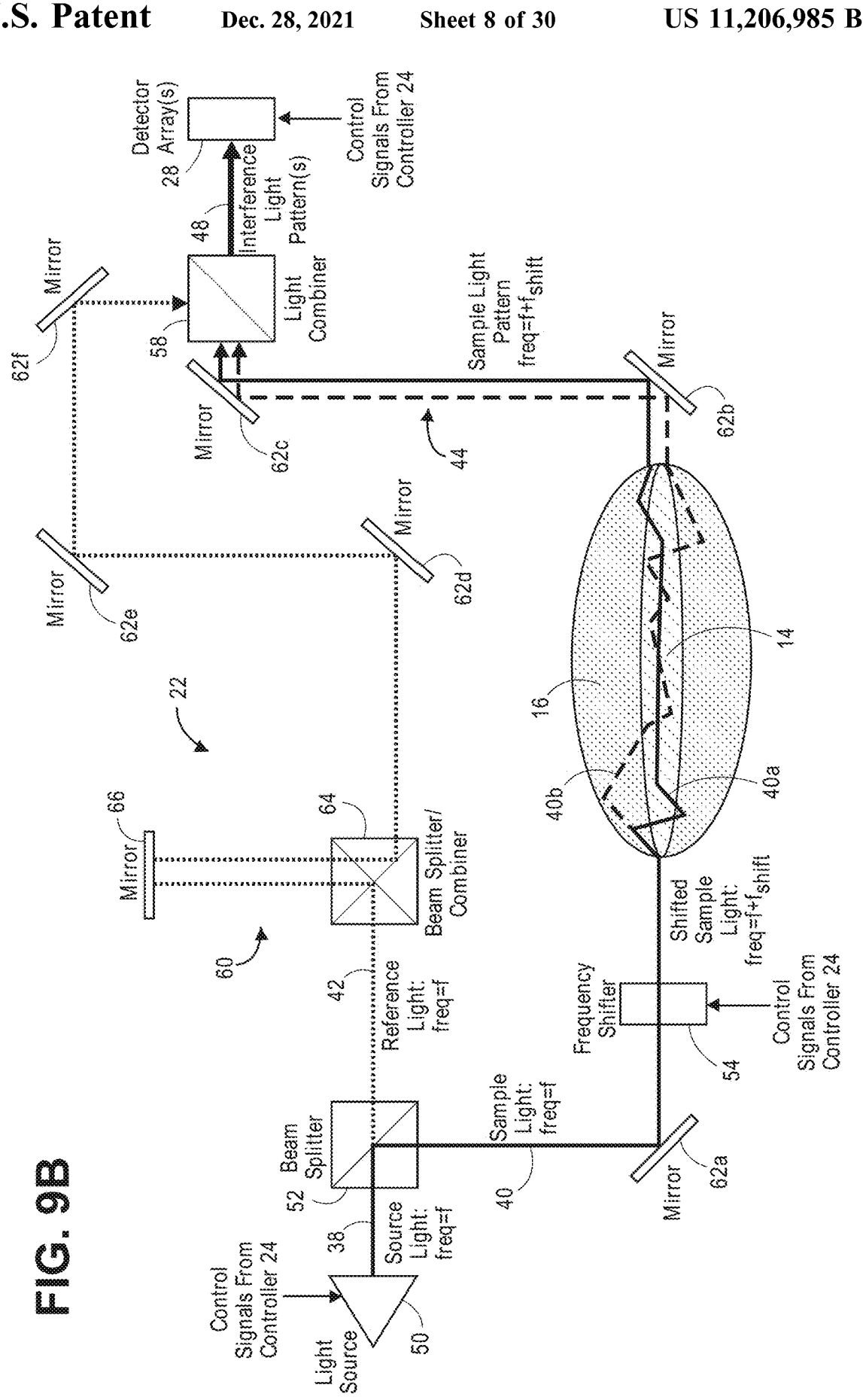
FIG. 9b is a block diagram of another embodiment of an interferometer used in the diffusive optical system of FIG. 8.
Figure 9C:
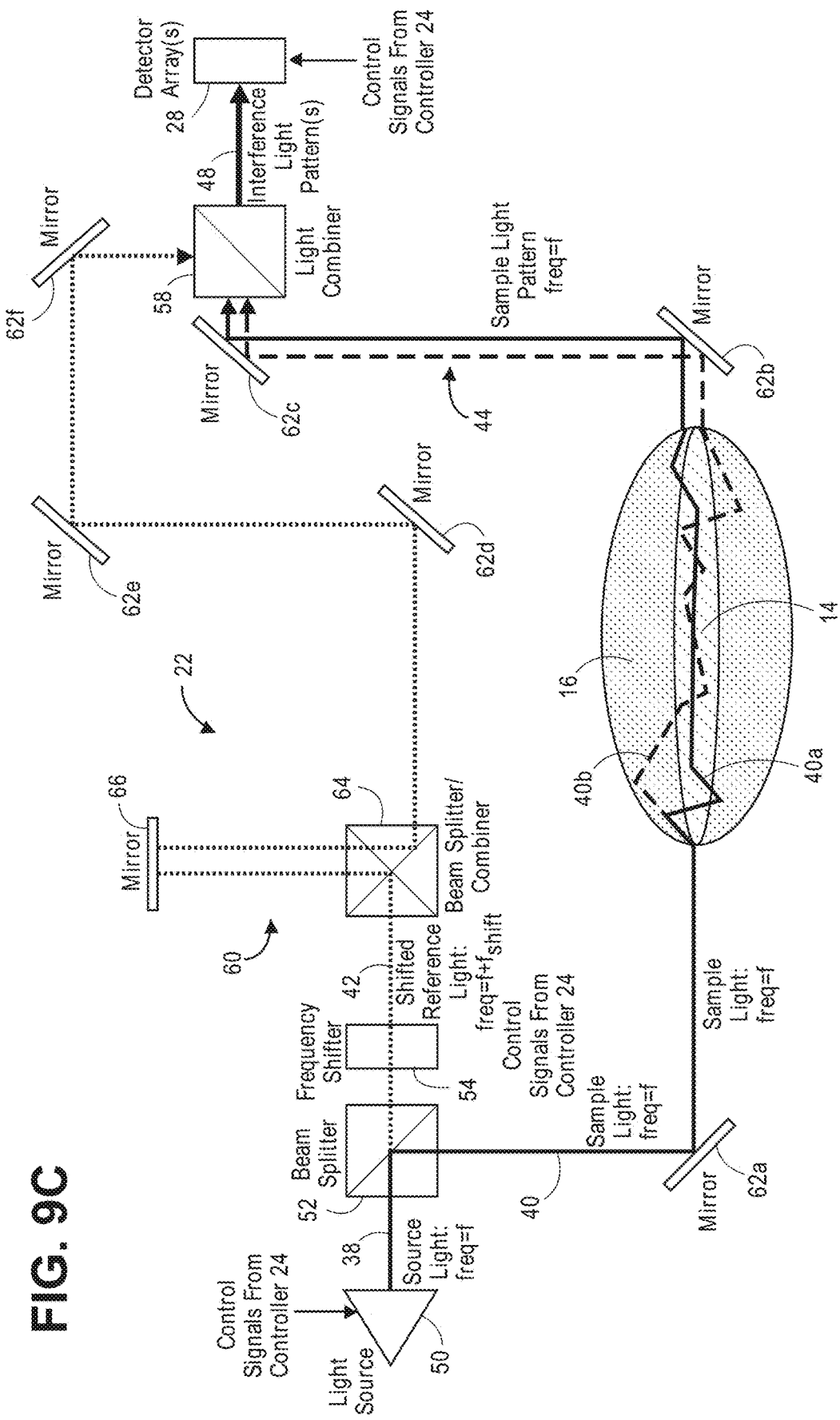
FIG. 9c is a block diagram of still another embodiment of an interferometer used in the non-invasive diffusive optical detection system of FIG. 8.
Figure 9D:
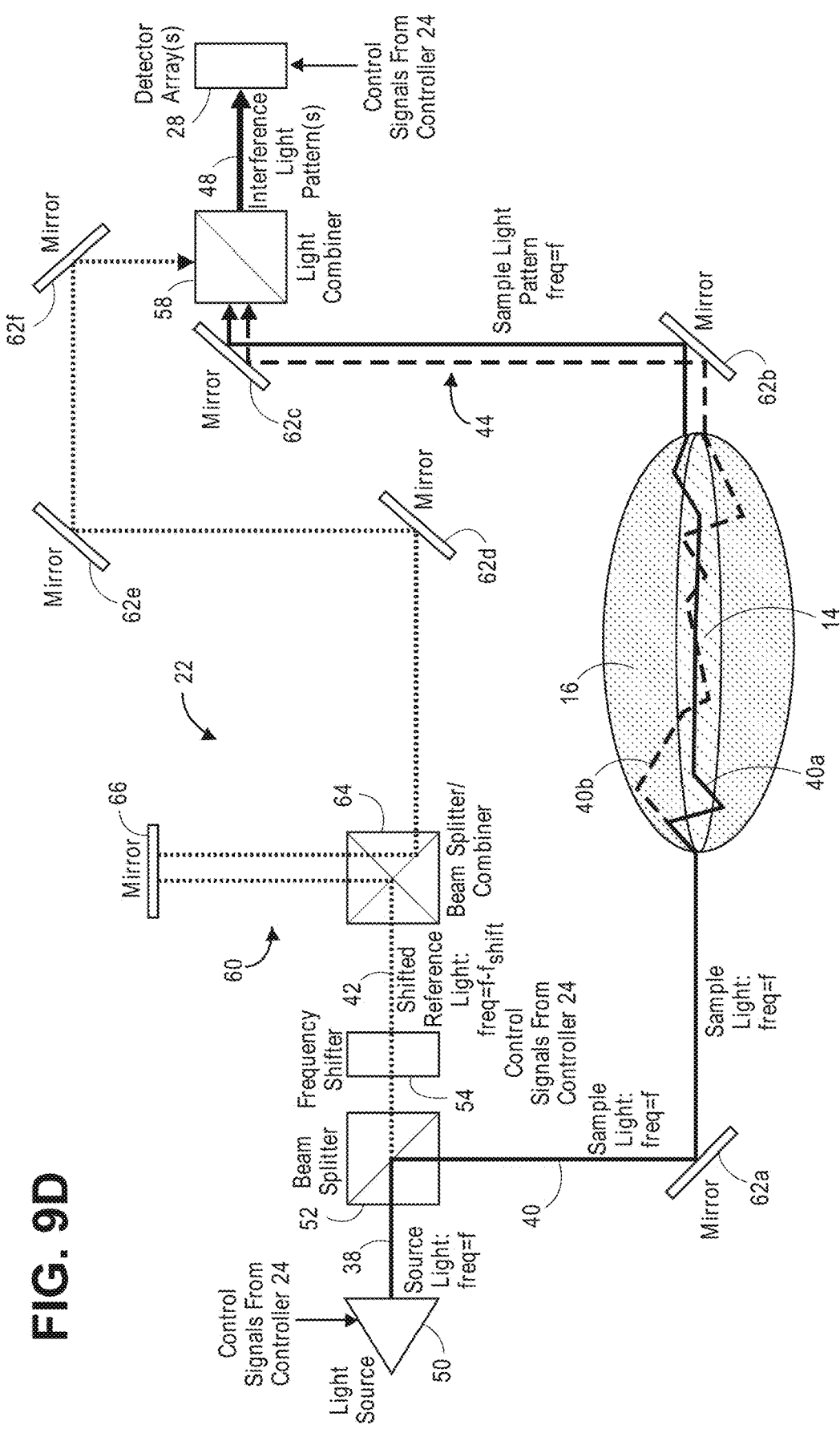
FIG. 9d is a block diagram of yet another embodiment of an interferometer used in the non-invasive diffusive optical detection system of FIG. 8.

To this end, and with reference to FIG. 9a, one embodiment of an interferometer 22 that can be used in the diffusive optical detection system 10 of FIG. 8. The interferometer 22 includes a light source 50, a beam splitter 52, an optical frequency shifter 54, a light splitter/combiner 58, a path length adjustment mechanism 60, and a mirror arrangement 62 (which comprise e.g., mirrors 62a, 62b, 62c, 62d, 62e, and 62f).

The light source 50 is configured for generating coherent light as the source light 38, preferably at a single wavelength (e.g., in the range of 605 nm to 1300 nm), and may take the form of, e.g., a laser diode. In alternative embodiments, multiple light source(s) (not shown) may be used to generate the source light 38 at multiple distinct wavelengths, e.g., one generating source light 38 within the range of 605 nm to 800 nm, and another generating source light 38 within the range of 800 nm to 1300 nm. The coherence length of the source light 38 is preferably at least one meter in order to generate the best speckle contrast in the interference light pattern(s) (in this case, the speckle light pattern(s)) 48. The light source 50 may receive power from a drive circuit (not shown), which may include control inputs for receiving control signals from the controller 24 that cause the light source 50 to emit the source light 38 at a selected time, duration, and intensity. As just one example, a distributed feedback (DFB) laser or similar laser may be used to achieve very narrow linewidths and extremely high amplitude stability. Thus, as will be described in further detail below, the controller 24 may selectively pulse the source light 38, and thus the sample light 40 and reference light 42.

The beam splitter 52 is configured for splitting the source light 38 into the sample light 40 that propagates along a sample arm of the interferometer 22 and reference light 42 that propagates along a reference arm of the interferometer 22. In the illustrated embodiment, the beam splitter 52 (e.g., a partially transparent mirror) splits the source light 38 via amplitude division by reflecting a portion of the source light 38 as the sample light 40, and transmitting the remaining portion of the source light 38 as the reference light 42, although the beam splitter 52 may alternatively reflect a portion of the source light 38 as the reference light 42, and transmit the remaining portion of the source light 38 as the sample light 40. In alternative embodiments, the beam splitter 52 may split the source light 38 via wavefront division by splitting a portion of the wavefront into the sample light 40 and splitting the remaining portion of the wavefront into the reference light 42. In either case, the beam splitter 52 may not necessarily split the source light 38 equally into the sample light 40 and reference light 42, and it may actually be more beneficial for the beam splitter 52 to split the source light 38 unevenly, such that the amplitude of the sample light 40 is less than the amplitude of the reference light 42 (e.g., 10/90 power ratio) in order to comply with tissue safety standards. That is, the amplitude of the sample light 40 will preferably be relatively low to avoid damaging the tissue, whereas the amplitude of the reference light 42, which will be used to boost the sample light pattern 44 in the interference light pattern 48, will be relatively high.

The optical frequency shifter 54 is configured for down frequency shifting the sample light 40 by the frequency offset $f_{shift}$ to $f-f_{shift}$, such that the frequency of the sample light pattern 44 will be $f-f_{shift}$, while the frequency of the reference light will be f, thereby enabling the heterodyne combination of the reference light 42 at frequency f and the sample light pattern 44 at frequency $f-f_{shift}$, as described above. In one alternative embodiment illustrated in FIG. 9b, the optical frequency shifter 54 is configured for up frequency shifting the sample light 40 by the frequency offset $f_{shift}$ to $f+f_{shift}$, such that the frequency of the sample light pattern 44 will be $f+f_{shift}$, the frequency of the reference light 42 will be f, thereby enabling the heterodyne combination of the reference light 42 at frequency f and the sample light pattern 44 at frequency $f+f_{shift}$. In another alternative embodiment illustrated in FIG. 9c, the optical frequency shifter 54 is configured for up frequency shifting the reference light 42 by the frequency offset $f_{shift}$ to $f+f_{shift}$, such that the frequency of the sample light pattern 44 will be f, while the frequency of the reference light 42 will be $f+f_{shift}$, thereby enabling the heterodyne combination of the reference light 42 at frequency $f+f_{shift}$ and the sample light pattern 44 at frequency f. In yet another alternative embodiment illustrated in FIG. 9d, the optical frequency shifter 54 is configured for down frequency shifting the reference light 42 by the frequency offset $f_{shift}$ to $f-f_{shift}$, such that the frequency of the sample light pattern 44 will be f, while the frequency of the reference light 42 will be $f-f_{shift}$, thereby enabling the heterodyne combination of the reference light 42 at frequency $f-f_{shift}$ and the sample light pattern 44 at frequency f. Thus, the interferometer 22 may be configured in any manner that shifts the frequencies of the sample light 40 and the reference light 42 by the frequency offset $f_{shift}$.

In any event, the frequency shifter 54 may include a local oscillator (not shown) that outputs a signal having a fixed or variable frequency. The local oscillator may be variable, in which case, it may have a control input for receiving control signals from the controller 24 that cause the local oscillator to output a signal at a defined frequency. Alternatively, the local oscillator may be fixed, in which case, it will output a signal having a fixed frequency. In either case, the frequency of the signal output by the local oscillator will be equal to the frequency offset $f_{shift}$.

The light splitter/combiner 58 is configured for combining the reference light 42 with the sample light pattern 44 via superposition to generate the interference light pattern(s) 48. The light splitter/combiner 58 can take the form of, e.g., a combiner/splitter mirror.

The path length adjustment mechanism 60 is configured for adjusting the optical path length of the reference arm to nominally match the expected optical path length of the sample arm. The path length adjustment mechanism 60 may include a beam splitter/combiner 64 and an adjustable mirror 66 that can be displaced relative to the beam splitter/combiner 64. The beam/splitter combiner 64 is configured for redirecting the reference light 42 at a ninety-degree angle towards the mirror 66, and redirecting the reference light 42 reflected back from the mirror 66 at a ninety-degree angle towards the light splitter/combiner 58. Thus, adjusting the distance between the mirror 66 and the beam splitter/combiner 64 will adjust the optical path length of the reference arm to match the optical path length of the sample arm.

The mirror assembly 62 is configured for confining the optical light paths in the interferometer 22 into a small form factor, and in the illustrated embodiment, includes a first tilted, completely reflective, mirror 62a configured for redirecting the sample light 40 at a ninety-degree angle towards the biological specimen 16, two tilted, completely reflective, mirrors 62b, 62c configured for redirecting the sample light 44 exiting the head 16 towards one face of the light splitter/combiner 58, and three tilted, completely reflective, mirrors 62d-62f configured for redirecting the reference light 42 towards another face of the light splitter/combiner 58. In an alternative embodiment, rather than using mirrors in the reference arm, a fiber optical waveguide can be used to between the beam splitter/combiner 64 and the light combiner 58, e.g., to more easily satisfy the form factor requirements of a wearable device.

The controller 24 is configured for operating the interferometer 22 to pulse the sample light 40 in synchrony with the frame rate of detector array(s) 28 (in the illustrated embodiment shown in FIG. 8), by sending on/off control signals to the drive circuit coupled to the light source 50 and the detector array(s) 28).

Figure 10:
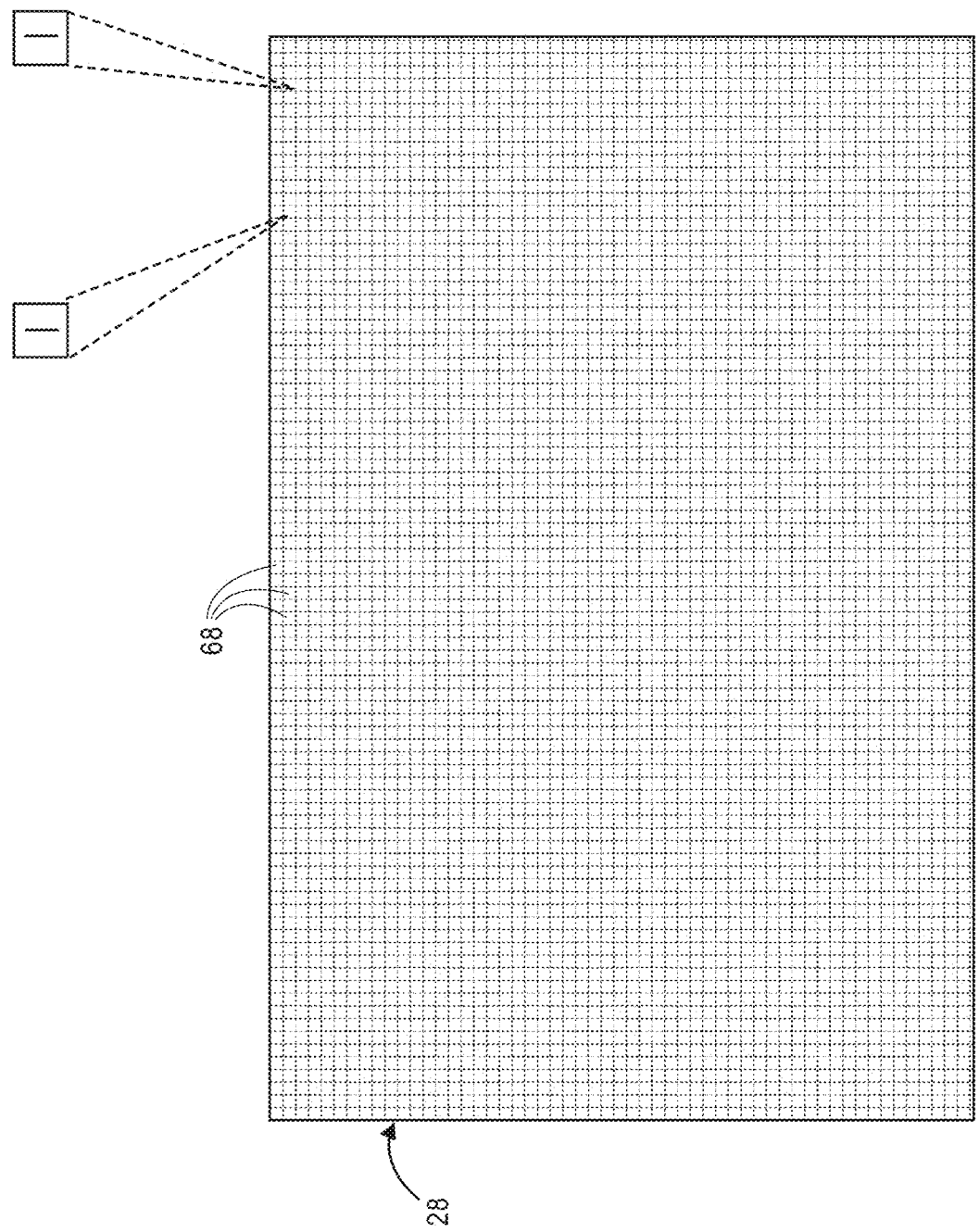
FIG. 10 is a schematic diagram of one embodiment of a detector array used in the non-invasive diffusive optical detection system of FIG. 8.

As shown in FIG. 10, the detector array(s) 28 takes the form of a conventional CCD camera, CMOS sensor, PD array, ADP array, SPAD detector, ToF camera, InGaAs sensor, etc., and includes an array of pixels 68, which are configured for simultaneously detecting the spatial components of the respective interference light pattern(s) 48. In the case where each of the interference light pattern(s) 48 is a speckle light pattern, the spatial components are speckle grains (approximately the size of a wavelength of the light) of the speckle light pattern. Each pixel 68 of a detector array 28 stores an intensity value I of a respective spatial component of a corresponding interference light pattern 48. As will be described in further detail below, the spatial component intensity values detected by the pixels 68 of the detector array(s) 28 will be used to assemble an intensity population distribution across the pixels 68, which can further be used to determine the existence of a fast-optical signal in the target volume of interest 14. Each of the detector array(s) 28 includes control inputs (not shown) for receiving control signals from the controller 24, such that detection of the intensity values can be coordinated with the pulsing of the sample light 40 described in further detail below.

It should be appreciated that each detector array 28 can be formed of, e.g., a single camera or closely spaced multiple cameras or camera regions. The types of cameras that can be used are described above. Although not illustrated, the diffusive optical detection system 10 may include magnification optics and/or apertures to magnify the individual speckle grains, which may have a size on the order of the wavelength of the near-infrared or visible light used to acquire the detected data measurements, and hence on the order of hundreds of nanometers in size, to approximately the sizes of the pixels 68 of the detector array(s) 28. Thus, in the illustrated embodiment, the pixel sizes and pitches of the detector array(s) 28 are matched to the speckle grain sizes and pitches of the respective speckle light pattern(s) 48 via the appropriate magnification, although other embodiments are possible.

Once the detector array(s) 28 acquires the data measurements by storing the spatial component intensity values of the interference light pattern(s) 48, these data can be sent to the processor 26 (which can, e.g., take the form of a computer, field-programmable gate array or application specific integrated circuit), which is configured for quantifying the spread (e.g., computing a standard deviation) of the intensity population distribution of a function of the spatial components of the interference light patterns 48 (e.g., by computing the standard deviation), and identifying a fast-optical signal within the target volume of interest 14 based on the quantified intensity population distribution spread. As briefly discussed above, such function may be, e.g., an identify function in the case of a single interference light pattern 48 or may be a subtraction function in the case of two interference light patterns 48. The processor 26 may be configured for identifying the presence of a fast-optical signal in the target volume of interest 14 if the quantified intensity population distribution spread is greater than a reference threshold. Such reference threshold may be the known spread of the intensity population distribution in the absence of the fast-optical signal in the target volume of interest 14 or may be a higher value.

The processor 26 may also be configured for determining the magnitude of such identified fast-optical signal based on the quantified intensity population distribution spread. For example, the processor 26 may refer to reference magnitude levels or values previously correlated to the different reference intensity population distribution spread levels or values (e.g., in a look-up table), with the reference magnitude levels or values of the fast-optical signal presumably incrementally increasing as the reference intensity population distribution spread levels or values increase. In the case, where the intensity population distribution spread is linear as a function of the magnitude of the fast-optical signal (i.e., phase angle change of the sample light), the magnitude of the identified fast-optical signal can simply be computed as a linear function of the intensity population distribution spread value.

As described above, it is desirable that the temporal beat component of the interference light pattern 48 integrate to a zero value over a measurement period to "balance" the interferometer 22 in the absence of a fast-optical signal in the target volume of interest 14, and to integrate to a non-zero value over a measurement period to "throw" the interferometer 22 "off balance" in the presence of a fast-optical signal in the target volume of interest 14. As a result, the temporal beat component serves as a signal component during the measurement period that results in a relatively narrow intensity population distribution in the absence of a fast-optical signal in the target volume of interest 14, but results in a relatively broad intensity population distribution in the presence of a fast-optical signal in the target volume of interest 14.

Figure 11A:
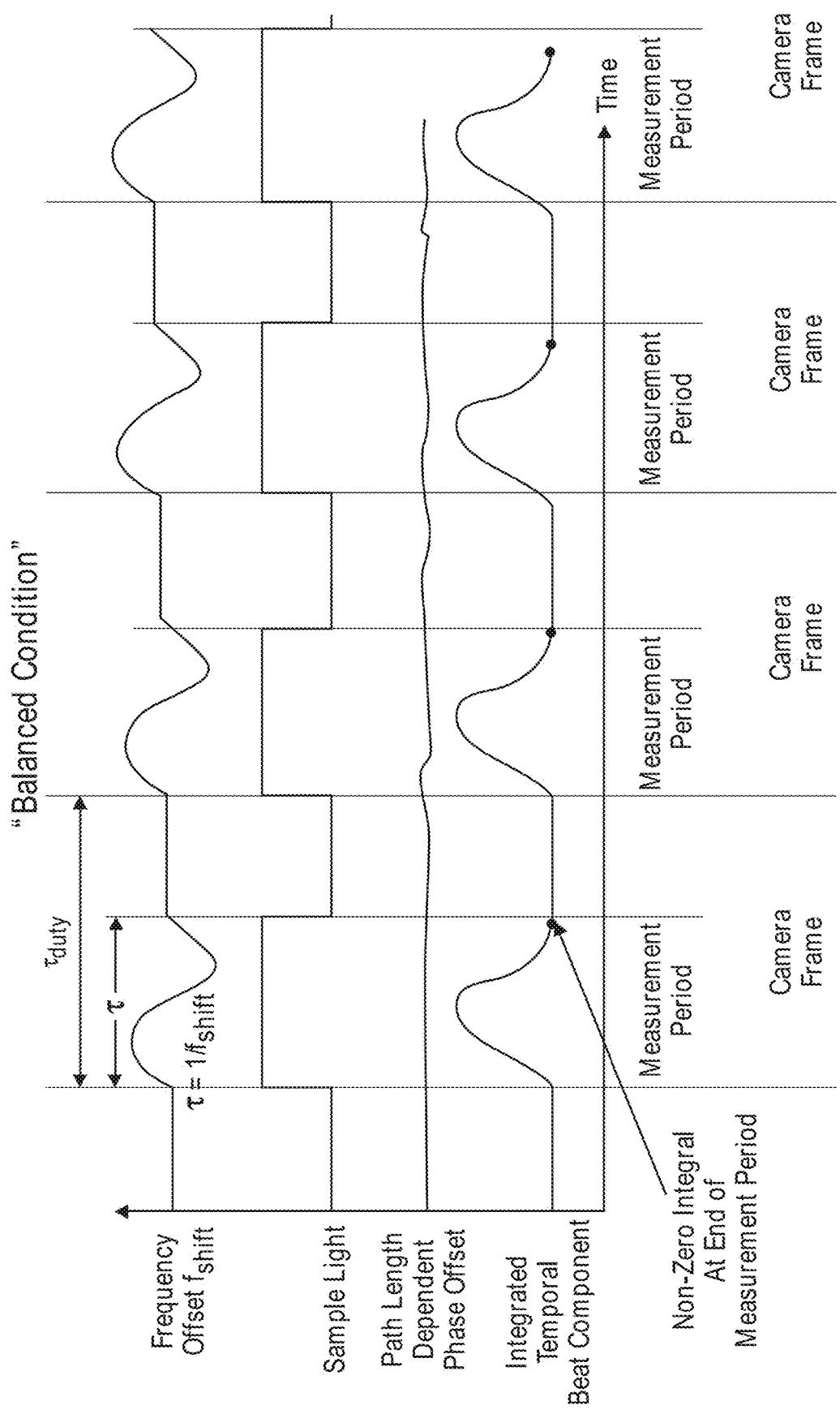
FIG. 11a is a timing diagram of pulsing sequence and frequency offset used by the non-invasive diffusive optical detection system of FIG. 8, and the path length dependent phase offset of the sample light and integrated temporal beat component of the interference light pattern resulting from the absence of a fast-optical signal in the tissue, showing a balanced condition.
Figure 11B:
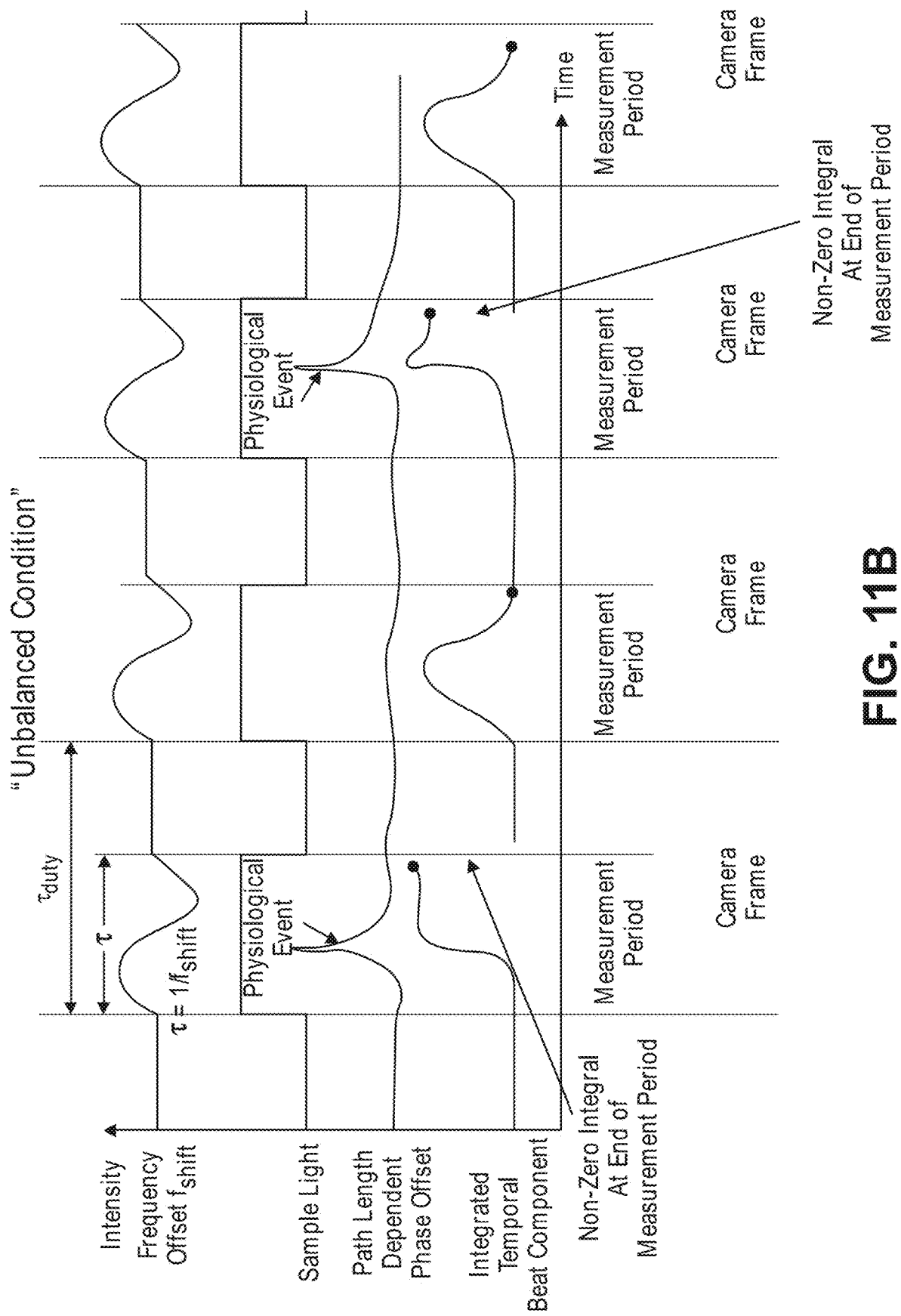
FIG. 11b is a timing diagram of pulsing sequence and frequency offset used by the non-invasive diffusive optical detection system of FIG. 8, and the path length dependent phase offset of the sample light and integrated temporal beat component of the interference light pattern resulting from the presence of a fast-optical signal in the tissue, showing an unbalanced condition.
Figure 12:
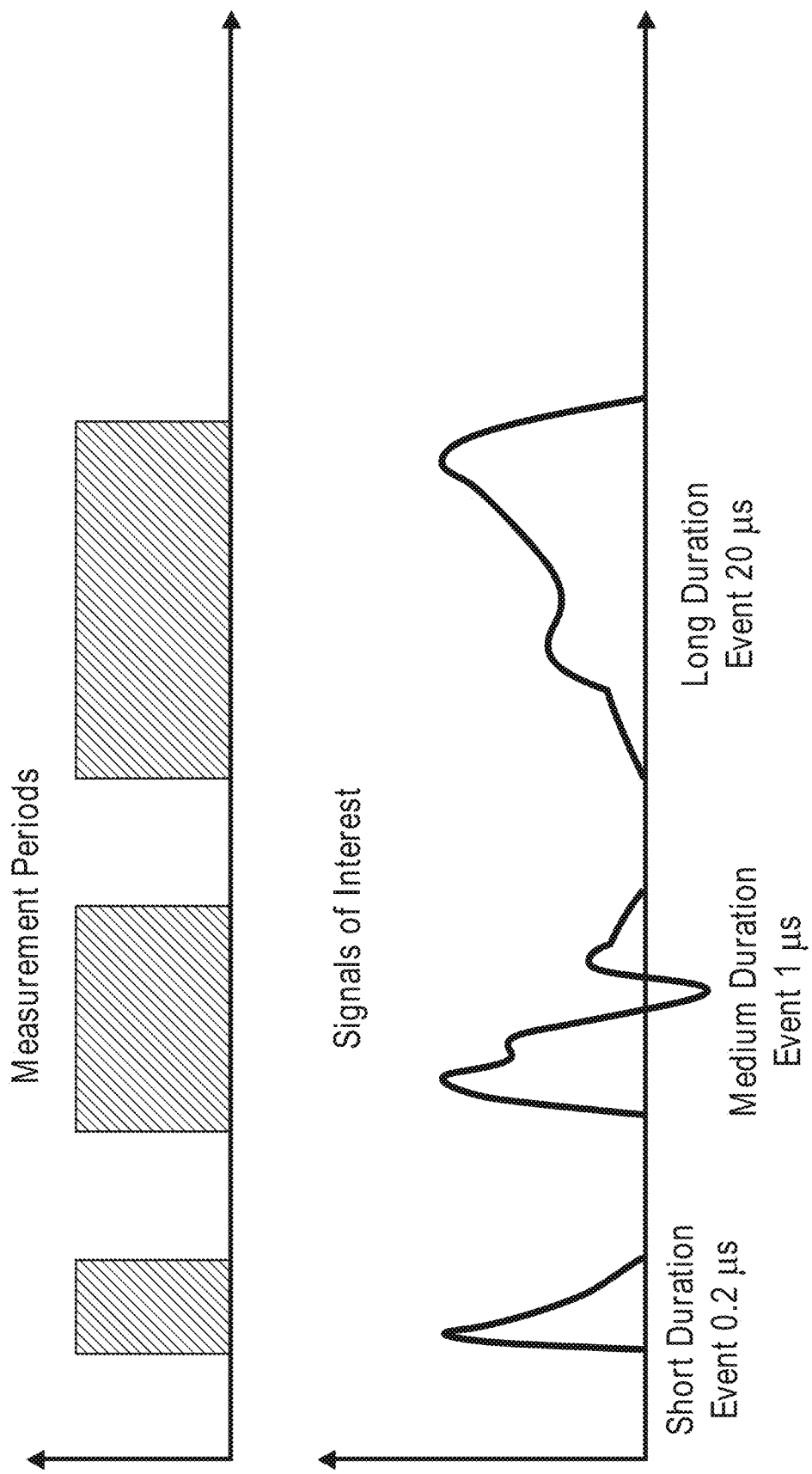
FIG. 12 is a timing diagram illustrating the selection of different measurement periods in the non-invasive diffusive optical detection system of FIG. 8 for different physiological event durations.

Referring to FIGS. 11a and 11b, the relationship between an exemplary frequency offset $f_{shift}$ between the sample light 40 and the reference light 42; an exemplary pulsed waveform of sample light 40; the resulting path length dependent phase offset of the sample light 40 propagating through the target volume of interest 14; and the resulting integrated temporal beat component due to the heterodyne combination of the sample light 40 and reference light 42 will be described in the "balanced" condition (absence of a fast-optical signal, as shown in FIG. 11a) and the "unbalanced" condition (presence of a fast-optical signal, as shown in FIG. 11b).

During one acquisition of a single detected data measurement (i.e., acquisition of data characterizing the target volume of interest 14), one or more pulses of the sample light 40 is delivered into the target volume of interest 14 during each measurement period. Although, in the embodiment illustrated in FIGS. 11a and 11b, only a single rectangular pulse of the sample light 40 is delivered into the target volume of interest 14 during each measurement period, it should be appreciated that other sample light pulse shapes and number of sample light pulses can be used in each measurement period, including, e.g., double Gaussian or even arbitrarily-shaped pulses, as described in further detail below.

As illustrated in FIG. 11a, in the absence of a fast-optical signal, the average path length of the sample light 40 within the target volume of interest 14 will be constant, such that the temporal beat component corresponding to that measurement period integrates to zero at the end of each measurement period. In contrast, as illustrated in FIG. 11b, in the presence of a fast-optical signal during the relevant measurement period, the average path length of the sample light 40 within the target volume of interest 14 will vary, such that the temporal beat component corresponding to that measurement period integrates to a non-zero value over the duration of that measurement period. It should be noted that, although the path length dependent phase offset is illustrated in FIG. 11b as being positive, the path length dependent phase offset may be negative or may be a mixture of positive and negative within a single measurement period or over multiple measurement periods.

In this example, the duration t of the respective measurement period is equal to $1/f_{shift}$ (i.e., one cycle of the temporal beat component) to maximize the data acquisition speed, although in alternative embodiments, the duration t of the measurement period may be equal to $N/f_{shift}$, where N is an integer greater than one (i.e., several cycles of the temporal beat component). In the illustrated embodiment, the duty cycle $\tau_{duty}$ of the temporal beat component is selected to match the frame rate of the detector array 28, such that there is only one measurement period for each frame of the detector array 28, although as will be described in further detail below, the duty cycle $\tau_{duty}$ of the temporal beat component may be selected, such that there are multiple measurement periods for each frame of the detector array 28.

The measurement period is preferably selected to be no longer than the duration of the signal of interest. If N=1, this means that $1/f_{shift}$ (and in the case where there is a single sample light pulse per measurement period), the duration of the pulse should not be longer than the duration of the signal of interest. As examples, and with reference to FIG. 12, if the signal of interest has a short duration event of 0.2 microseconds, the measurement period (and in this case the duration of the sample light pulse) should be no longer than 0.2 microseconds), and thus, the frequency offset $f_{shift}$ should be no less than 5 MHz; if the signal of interest has a medium duration event of 1 microsecond, the measurement period (and in this case the duration of the sample light pulse) should be no longer than 1 microsecond), and thus, the frequency offset $f_{shift}$ should be no less than 1 MHz; and if the signal of interest has a long duration event of 20 microseconds, the measurement period (and in this case the duration of the sample light pulse) should be no longer than 20 microseconds), and thus, the frequency offset $f_{shift}$ should be no less than 0.05 MHz.

The measurement period is preferably also set to be no greater than the "speckle decorrelation time" of the target volume of interest 14. The speckle decorrelation time is due to the scatterers' motion (for example, blood flow) inside living biological tissue, and rapidly decreases with the depth at which the biological tissue is to be measured, and in particular, scales super-linearly with the depth into the anatomical structure 16 at which the target volume of interest 14 is located, falling to microseconds or below as the measurement depth extends to the multi-centimeter range.

Figure 13:
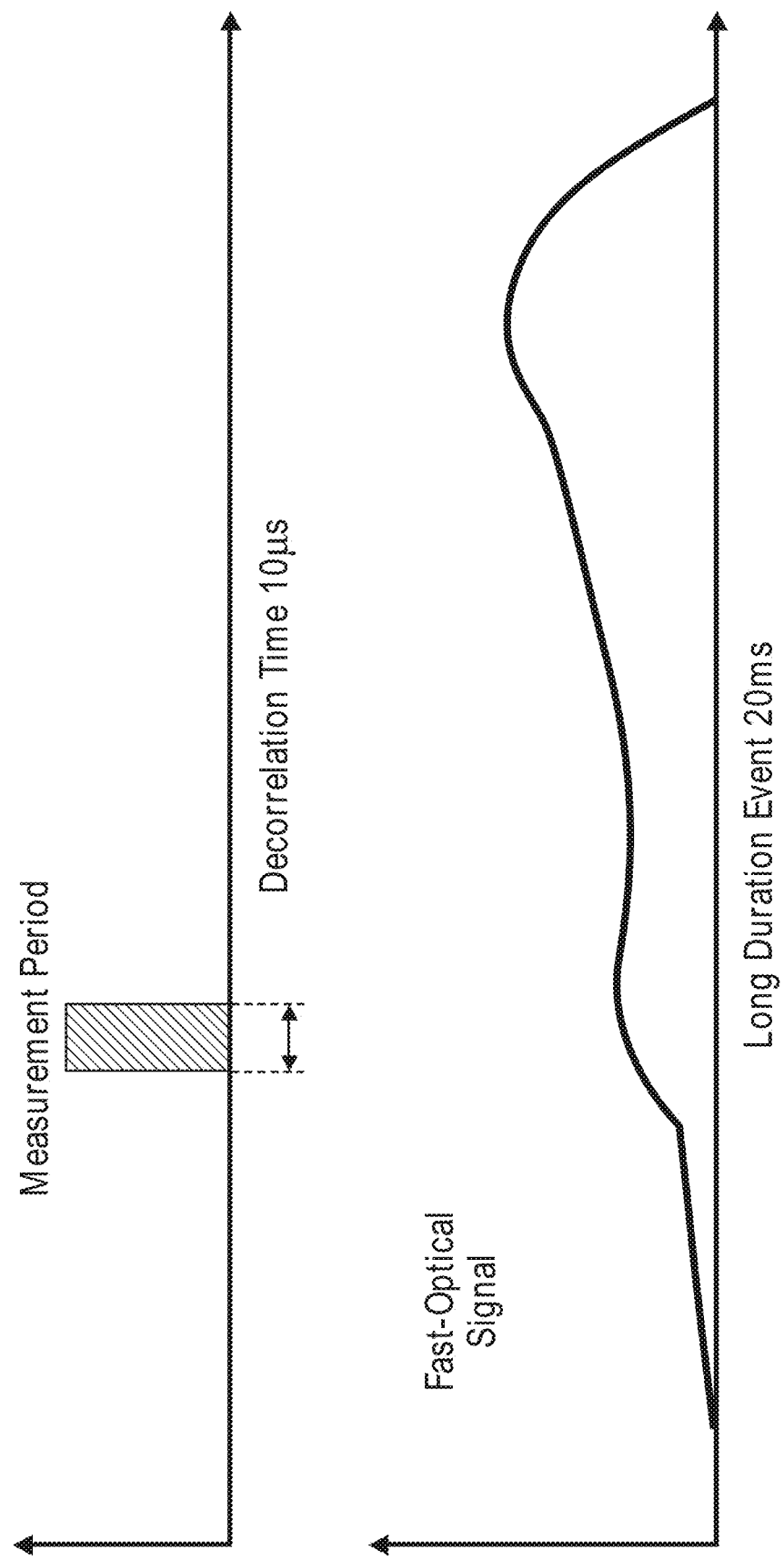
FIG. 13 is a timing diagram illustrating a relatively short measurement period used to detect a relatively long fast-optical signal.

Although the measurement period is illustrated in FIG. 11b as being on the order of the duration of the fast-optical, fast-optical signals may, in reality, be much greater than the speckle correlation time of the target volume of interest 14 (typically ~0.1 ms-1 ms), and thus, the measurement period may be much smaller than the duration of a fast-optical signal, as illustrated in FIG. 13. However, in the case where the duration of the fast-optical signal is much greater than the measurement period, the resulting path length dependent phase offset will be relatively small (likely, only a fraction of a degree), which will keep the response (i.e., the spread of the population density distribution) linear (i.e., sine of the phase angle approximately equals the phase angle).

Figure 14:
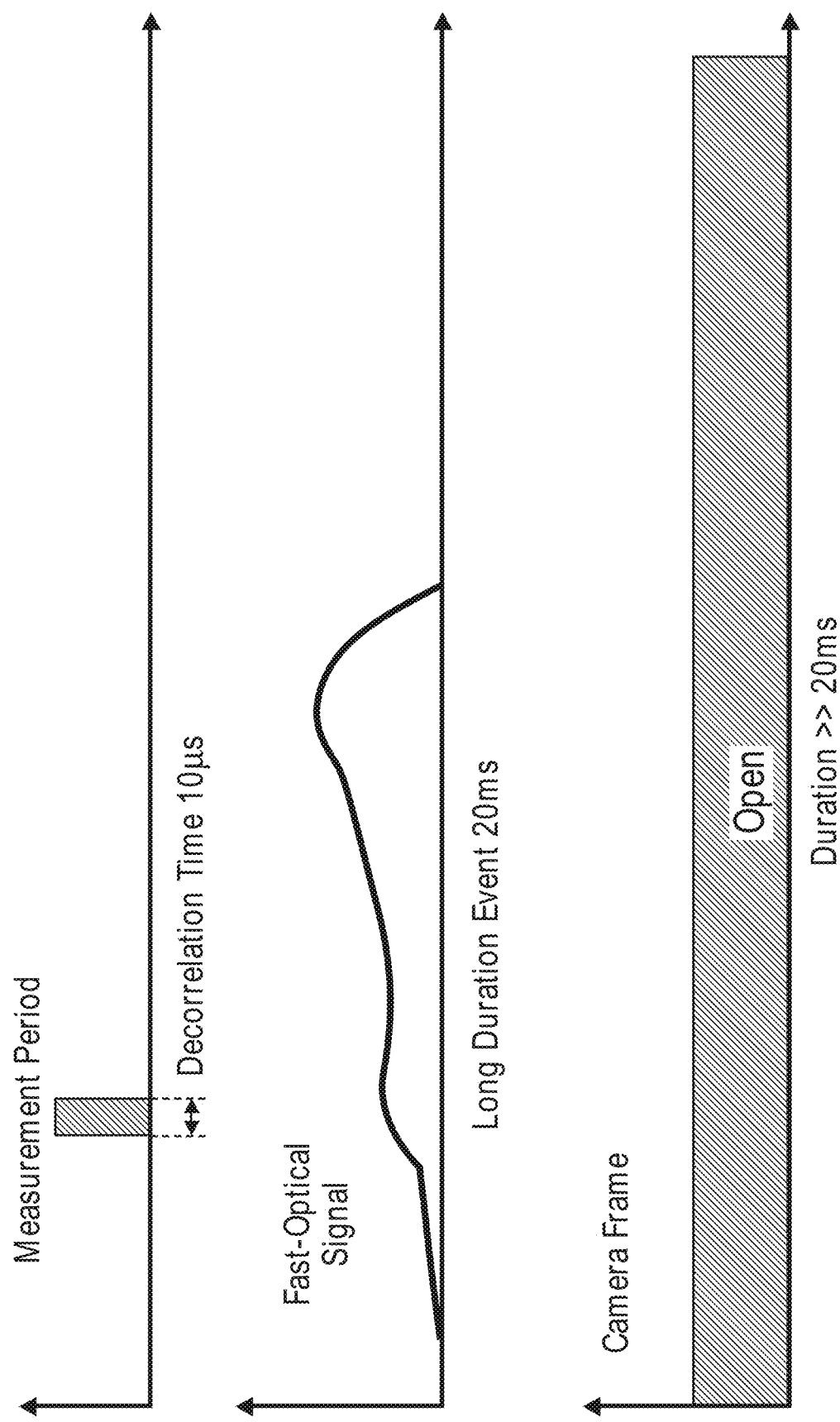
FIG. 14 is a timing diagram illustrating a relatively short measurement period that coincides with a relatively long fast-optical signal during a camera frame.

It should also be noted that although the duration t of the measurement period is illustrated as being on the order of a single active period of a detector array (in this case, a single camera frame (exposure or readout time) as shown in FIGS. 11a and 11b, the duration t of the measurement period may be much less than the duration of a single camera frame. In particular, due to the limited frame rate of the detector array 28, the duration of each camera frame may be much greater than the decorrelation speckle time (~0.01 ms-1 ms), thus dictating that the duration t of the measurement period be much less than the duration of each camera frame. However, even if a fast-optical signal causes changes in the path length of the sample light 40 on timescales much quicker than the frame rate of the detector array 28 (neural action potential time-course contains significant variation on a sub-millisecond timescale, with spike shapes often being measured at 10 KHz or 20 KHz in electrophysiological measurements), as long as the measurement period coincides with the fast-optical signal, the fast-optical signal can still be detected using a detector array 28 with a high-pixel-count (so as to obtain a high signal-to-noise ratio), as illustrated in FIG. 14.

Figure 15:
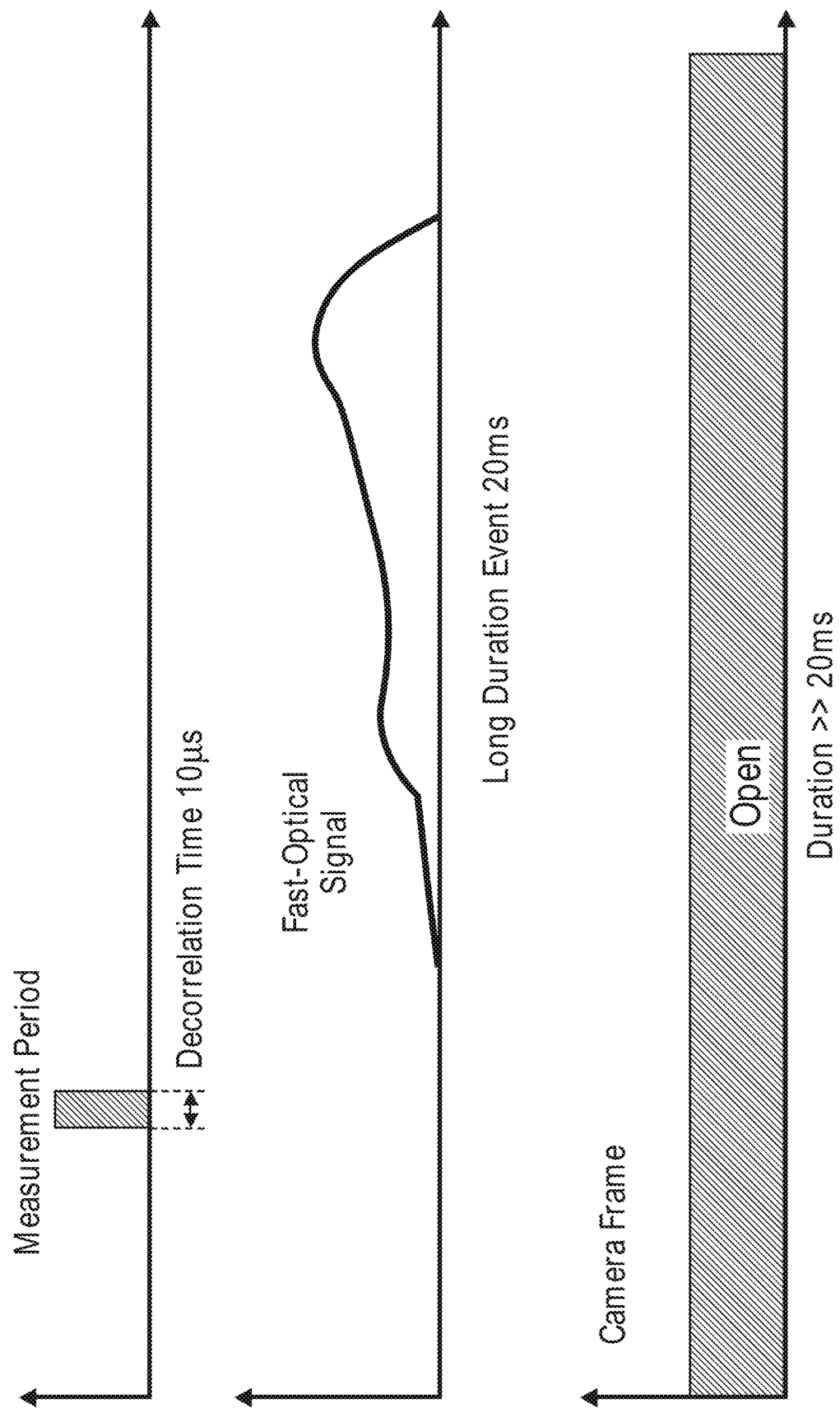
FIG. 15 is a timing diagram illustrating a relatively short measurement period that does not coincide with a relatively long fast-optical signal during a camera frame.
Figure 16:
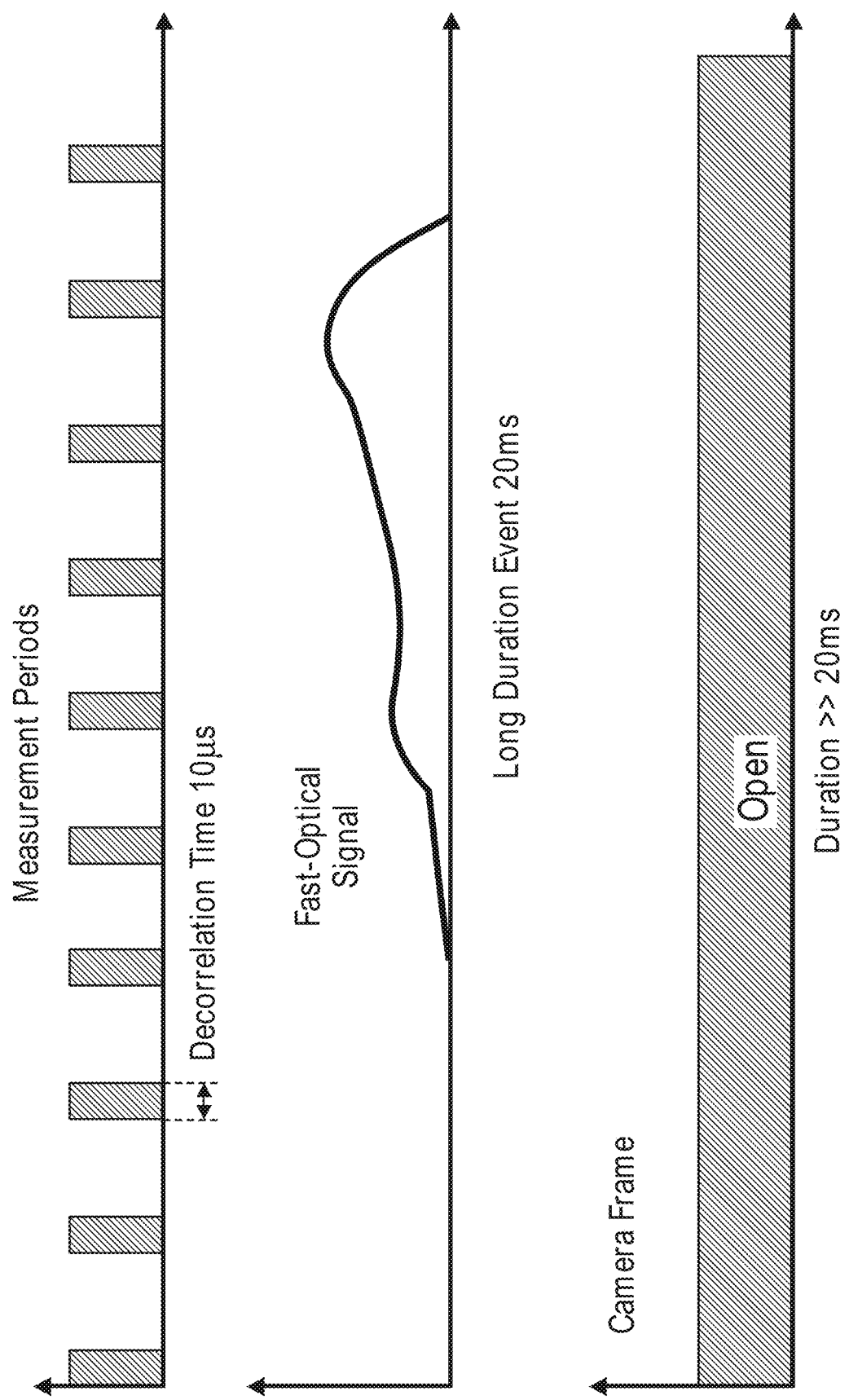
FIG. 16 is a timing diagram illustrating a multitude of relatively short measurement periods, some of which coincide with a relatively long fast-optical signal during a camera frame.
Figure 17:
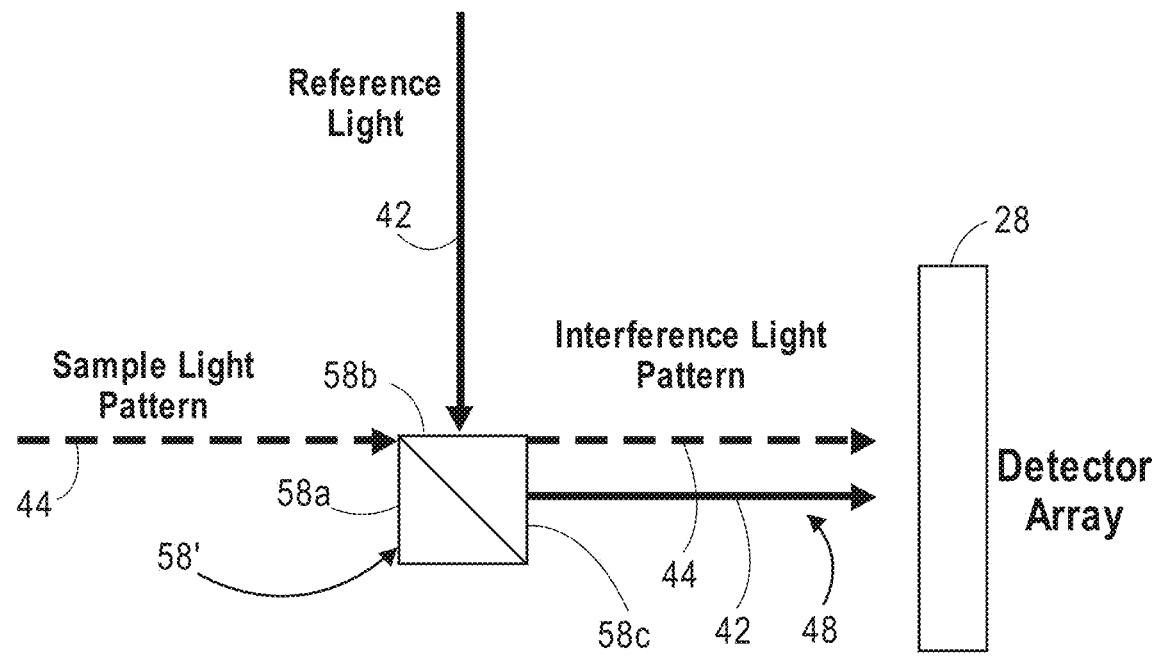
FIG. 17 is a block diagram of one specific embodiment of an interferometer and detector array that can be used in the non-invasive diffusive optical detection system of FIG. 8.

However, because it is possible for the measurement period to not coincide with the fast-optical signal, as illustrated in FIG. 15, the fast-optical signal may not be detected in this case. In an alternative embodiment, multiple measurement periods may be triggered across each frame of the detector array 28 in order to distribute the sensitivity to the fast-optical signal over the entire frame, as illustrated in FIG. 16. Alternatively, subject to regulatory limits on light fluence in tissue, more light energy may be provided in a smaller number of pulses of sample light 40 per camera frame (e.g., one pulse per camera frame) that lasts only a fraction of the duration of the camera frame. It should be appreciated that, although the camera frame is illustrated in FIGS. 14-16 as being longer than the duration of the fast-optical signal, a camera frame may be shorter than the duration of a fast-optical signal, the only limitation being that the duration of the camera frame be at least as long as the measurement period, As discussed above with respect to FIGS. 8 and 9a-9d, the interferometer may generate a single interference light pattern 48 during each measurement period, in which case, only a single detector array 28 (e.g., a single camera) is needed to detect the interference light pattern 48. For example, as illustrated in FIG. 17, a light combiner 58' (which replaces the light splitter/combiner 58 illustrated in FIGS. 9a-9d) is configured for combining the sample light pattern 44 and the reference light 42 to generate a single interference light pattern 48. That is, the light combiner 58' transmits the sample light pattern 44 and reflects the reference light 42, wherein they interfere to generate the interference light pattern 48.

Figure 18:
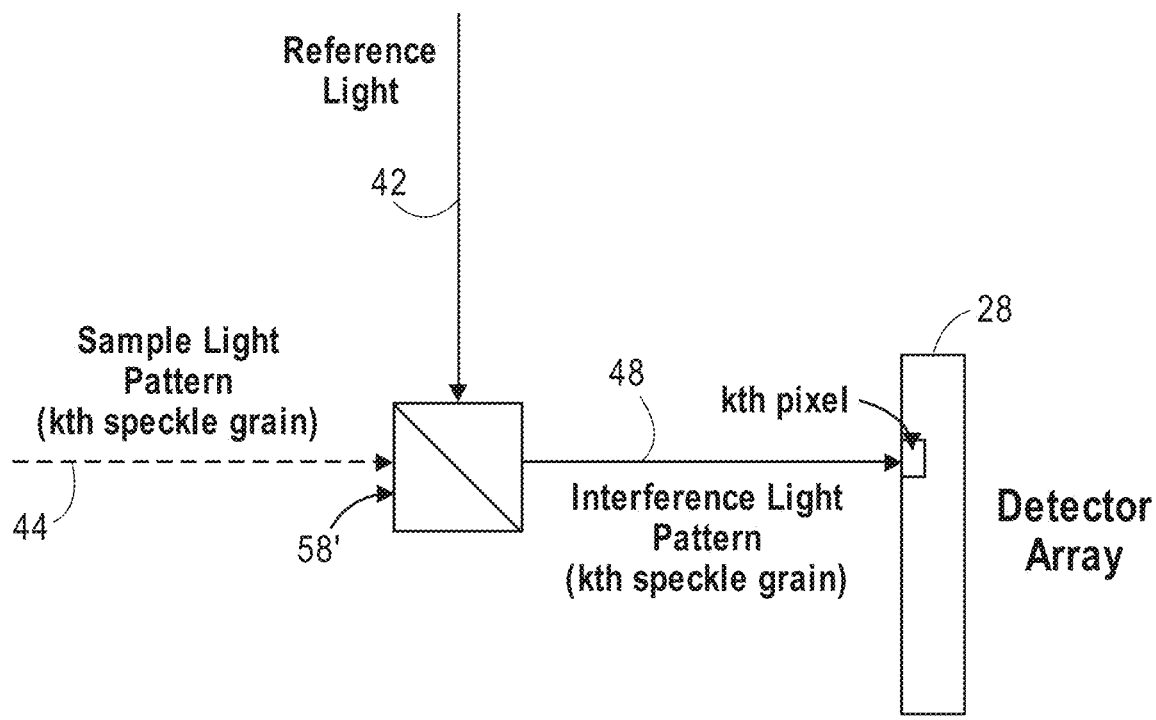
FIG. 18 is a block diagram of the interferometer and detector array of FIG. 8, particularly showing the generation and detection of a kth speckle grain of an interference pattern.

As illustrated in FIG. 18, each kth speckle of the interference light pattern 48 corresponds to a kth pixel of the detector array 28. That is, a spatial component of the sample light pattern 44 (i.e., the kth speckle grain of the speckle light field) interferes with the reference light 42 to generate a kth speckle grain of the interference light pattern 48 that is detected by kth pixel of the detector array 28. It should be appreciated that although FIG. 18 illustrates one speckle grain "k," an equivalent process for measuring the speckle grain k takes place for all speckles grains in parallel in the manner of imaging an entire speckle light field.

As discussed above, the pulsed waveform of the sample light 40 and the frequency offset $f_{shift}$ between the sample light 40 and the reference light 42 can be selected, such that the temporal beat component of the interference light pattern 48 illustrated in FIG. 18 integrates to a zero value in the absence of a fast-optical signal in the target volume of interest 14, resulting in a relatively narrow intensity population distribution across the pixels 68 of the detector array 28, and integrates to a non-zero value in the present of a fast-optical signal in the target volume of interest 14, resulting in a relatively broad intensity population distribution across the pixels 68 of the detector array 28.

In particular, assuming a frequency offset between the sample light 40 and the reference light 42 of $f_{shift}$, the intensity of the interference light pattern 48 detected at a kth pixel of the detector array 28 can be expressed as:

$$\text{Value}_k = \int_{t_0}^{t_1} (P_{sample}(t) + P_{reference}(t) + 2\sqrt{P_{sample}(t) \times P_{reference}(t)} \times (\sin(2\pi(-f_{shift})t + \theta_{unknown,speckle\,k} + 2\pi \times \delta/\lambda)))dt,$$ [1]

where $P_{sample}$ represents the sample light 40 as a function of time t, $P_{reference}$ represents the reference light 42 as a function of time t, $t_0$ is the beginning of the measurement period, $t_1$ is the end of the measurement period, $\theta_{unknown,\,speckle\,k}$, is a random phase at the kth speckle grain of the speckle light pattern at the time of measurement, which originates via multiple scattering of coherent light inside the tissue; and δ is the average path length shift of the sample light 40 (sample arm) due to fast-optical signals in the target volume of interest 14, assuming the reference light 42 (reference arm) has a fixed path length. It should be appreciated that, due to the variable t, the average path length shift δ is a path length shift.

The temporal beat component in equation [1] is represented by:

$$2\sqrt{P_{sample}(t) \times P_{reference}(t)} \times (\sin(2\pi(-f_{shift})t + \theta_{unknown,speckle\,k} + 2\pi \times \delta \times t/\lambda)).$$ [2]

Assuming the absence of a fast-optical signal, the average path length shift of the sample light 40 in the target volume of interest 14 will be constant, and thus, the average path length shift of the sample light δ will be equal to zero. In this case, the temporal beat component [2] will reduce to:

$$2\sqrt{P_{sample}(t) \times P_{reference}(t)} \times (\sin(2\pi(-f_{shift})t + \theta_{unknown,speckle\,k})).$$ [3]

As discussed above, it is desirable that the temporal beat component of the interference light pattern integrate to zero for all for all possible values of the unknown phase $\theta_{unknown}$, and thus for all pixels k in the detector array 28, in the absence of a fast-optical signal. As a general rule, a function of the shape of the pulsed waveforms for the sample light 40 and the frequency offset $f_{shift}$ between the sample light 40 and the reference light 42 can be selected in accordance with the following equation, such that the temporal beat component [3] always integrates to zero in the absence of a fast-optical signal, as follows:

$$\int_{t_0}^{t_1} 2\sqrt{P_{sample}(t) * P_{reference}(t)} \times \sin(2\pi f_{shift} + \theta_{unknown,speckle\,k})dt = 0,$$ [4]

If the sample light 40 has a single rectangular pulse per measurement period, the product term between the sample light 40 and the reference light 42 does not vary with time, and can thus be removed from the integral. Assuming that the duration of the rectangular pulse of the sample light 40 equals the measurement period, equation [4] reduces to:

$$2\sqrt{P_{sample} * P_{background}} \times \int_0^{T_{op}} \sin(2\pi f_{shift} + \theta_{unknown,speckle\,k})dt = 0,$$ [5]

where $T_{op}$ is the duration of a single pulse of the sample light 40.

Over the duration of the pulse $T_{op}$, equation [5] integrates to:

$$2\sqrt{P_{sample}(t) * P_{reference}(t)}/2\pi f_{shift} * (\cos(2\pi f_{shift} * T_{op} + \theta_{unknown,speckle\,k}) - \cos(\theta_{unknown,speckle\,k}))$$ [6]

Figure 19:
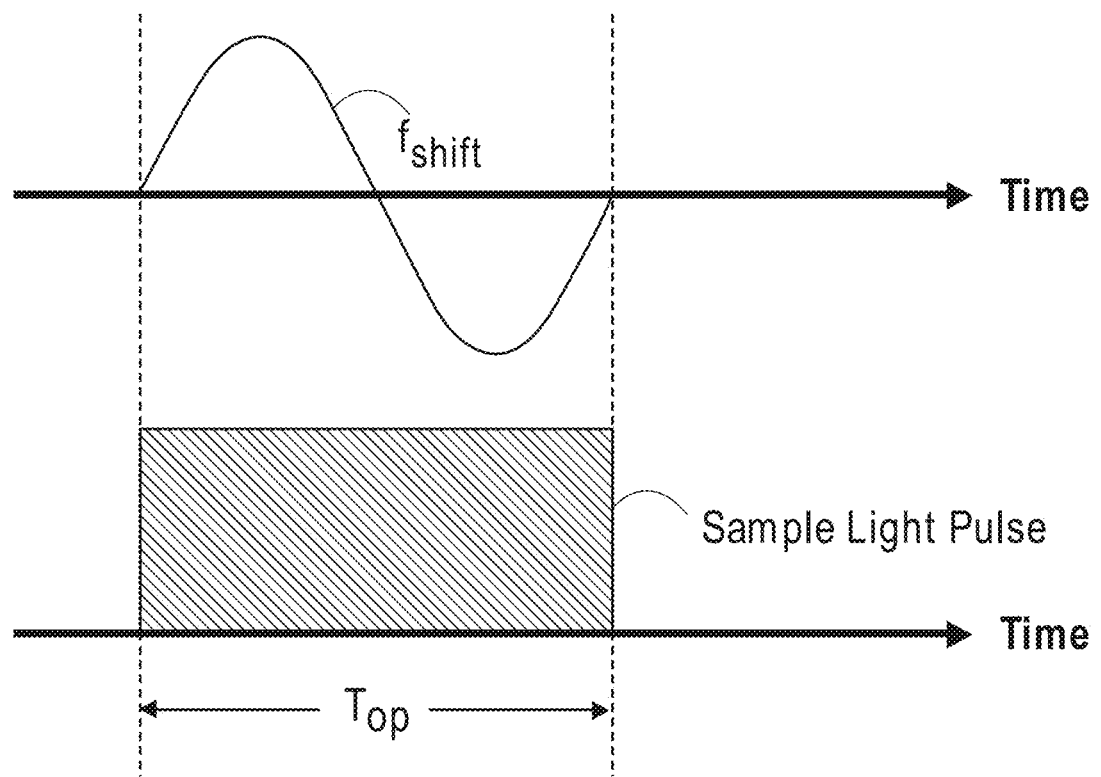
FIG. 19 is a timing diagram illustrating a relationship between the duration of a single sample light pulse and a frequency offset between the sample light and the reference light that can be used in the non-invasive diffusive optical detection system of FIG. 8 to generate a temporal beat component that integrates to zero.

If the frequency offset $f_{shift}$ and the optical pulse duration $T_{op}$ are selected, such that duration of temporal beat component over N cycles is equal to the optical pulse duration $T_{op}$, as illustrated in FIG. 19 (N=1), or in other words, are selected in accordance with the following equation:

$$f_{shift} * T_{op} = 1,$$ [7]

then equation [6] will be satisfied for every value of phase $\theta_{unknown}$, and the temporal beat component of the interference light pattern 48 will integrate to zero for every pixel 64 of the detector array 28.

If the pulses of the sample light 40 are not rectangular, but rather vary over time, it has been discovered that if the sample light 40 has a pulsed waveform shape with double pulses for each measurement period (i.e., each cycle of the frequency offset $f_{shift}$ between the sample light 40 and the reference light 42), for any selection of a pair of identically shaped pulses for the sample light 40, equation [4] will be satisfied for every value of phase $\theta_{unknown}$ (and the temporal beat component of the interference light pattern 48 integrates to zero) if the identically shaped pulses are separated from each other by:

$$d_{separation} = \frac{1}{2} * f_{shift},$$ [8]

where $d_{separation}$ is the separation between any point on the first pulse and the corresponding point on the second pulse.

As one example illustrated in FIG. 20a, two identical arbitrarily-shaped pulses L will satisfy equation [4] when the separation $d_{separation}$ between two corresponding points on the pulses L is equal to $\frac{1}{2} * f_{shift}$. As illustrated in FIG. 20b, it follows that two identical symmetrical pulses, and in this case, Gaussian pulses, will satisfy equation [4] when the separation $d_{separation}$ between two corresponding points on the pulses L is equal to $\frac{1}{2} * f_{shift}$.

It should be appreciated that, although it may be optimal to completely integrate the temporal beat component of the interference light pattern 48 to absolute zero, the presence of inherent shot noise (even though minimized by using the detectors 68 of the detector array(s) 28 together) will make it difficult for the temporal beat component of the interference light pattern 48 to integrate to absolute zero. However, it is still desirable to integrate the temporal beat component of the interference light pattern 48 to approximately a zero value (i.e., equation [4] approximately equals 0). For the purposes of this specification, the temporal beat component of the interference light pattern 48 integrates to approximately zero over the measurement period if such value is equal to or less than 10 percent of the absolute integral of the temporal beat component of the interference light pattern 48. Preferably, the temporal beat component of the interference light pattern 48 is equal to or less than 1 percent of the absolute integral of the temporal beat component of the interference light pattern 48 to minimize the signal noise as much as possible. Shot noise is a separate component of the signal that is not included in this definition.

Assuming the presence of a fast-optical signal, the average path length shift of the sample light 40 in the target volume of interest 14 will vary in a manner reflective of the dynamics of the fast-optical signal and hence functional (e.g., neural) activity in the target volume of interest 14. As a result, the average path length shift of the sample light δ in equation [2] will no longer be equal to zero. Consequently, the intensity of the temporal beat component [2] will be a non-zero value, which will represent the signal S that is largely correlated to the fast-optical signal in the target volume of interest 14. That is, since the intensity of the temporal beat component [2] was set to zero (or approximately zero) in the absence of a fast-optical signal, the signal S will be strongly correlated to the path length term ($2\pi \times \delta/\lambda$) contributed to the temporal beat component [2] by the fast-optical signal. Such signal S will potentially be different for each speckle grain or pixel, but on average will be non-zero and correlated with the average path length change that would be observed in frequency domain DOT or other methods.

Because the speckle phases are random, according to the known principles of wavefront measurement from strongly scattering media, it is known that a single-pixel detector will not scale to high signal to noise ratios. In particular, the aggregate signal over a large single-pixel detector would scale as the square root of detector size, but so would shot noise in the background, and hence the signal to noise ratio performance of a large detector would not increase with detector size. In contrast, with detection at each detector (or pixel), the aggregate signal scales linearly with the number of pixels, while the aggregate background shot noise scales as the square root, and hence signal to noise performance increases as the square root of the number of pixels, giving a strong advantage for using large numbers of pixels.

Significantly, as the signal S described above increases, the spread of the intensity population distribution likewise increases. Assuming an arbitrary function F, which can be denoted the path length term $2\pi \times \delta/\lambda$, but may alternatively be due to other causes that change the temporal beat component $2\sqrt{P_{sample}(t) \times P_{reference}(t)} \times (\sin(2\pi(-f_{shift})t+\theta_{unknown,speckle\ k}))$, the intensity of the interference light pattern 48 detected at a kth pixel of the detector array 28 expressed in equation [1] can alternatively be expressed as:

$$\text{Value}_k = \int_{t_0}^{t_1} (P_{sample}(t)+P_{reference}(t)+2\sqrt{P_{sample}(t) \times P_{reference}(t)} \times (\sin(2\pi(-f_{shift})t+\theta_{unknown,speckle\ k}+F(t))))dt, \quad [9]$$

If F(t) is linear, such that it can be written as M*t+B, then equation [9] can be expanded to:

$$\text{Value}_k = \int_{t_0}^{t_1} (P_{sample}(t)+P_{reference}(t)+2\sqrt{P_{sample}(t) \times P_{reference}(t)} \times (\sin(2\pi(-f_{shift})t+\theta_{unknown,speckle\ k}+M \times t+B)))dt, \quad [10]$$

After integration, and assuming a rectangular pulse waveform for the sample light 40, the number of detected photoelectrons will be proportional to $$(P_{sample}+P_{reference}) \times t_{int}+2\sqrt{P_{sample} \times P_{reference}}\int_0^{t_{int}} (\sin(2\pi(-f_{shift})t+\theta_{unknown,speckle\ k}+M \times t+B)), \quad [11]$$

where $t_{int}$ is the integration time, which is equal here to the duration of pulse of the sample light 40 (i.e., $1/f_{shift}$ in the case where there is one cycle of the temporal beat component over the duration of the pulse of the sample light 40 (N=1)).

For simplicity, the constant phase B can be subsumed into the random phase term $\theta_{unknown,speckle\ k}$, and the term $2\pi f_{shift}$ and the variable phase M can be combined, such that term [11] can be expressed as:

$$(P_{sample}+P_{reference}) \times t_{int}+2\sqrt{P_{sample} \times P_{reference}}\int_0^{t_{int}} (\sin(2\pi(-f_{shift}+M/2\pi)t+\theta_{unknown,speckle\ k})). \quad [12]$$

Assuming $t_{int}=1/f_{shift}$, the integral of the temporal beat component of the term [12] will be:

$$(\cos(2\pi(-f_{shift}+M/2\pi)/f_{shift}+\theta_{unknown,speckle\ k})-\cos(\theta_{unknown,speckle\ k}))/2\pi(f_{shift}+M/2\pi). \quad [13]$$

The term [13] can be reduced to:

$$(\cos(M/2\pi f_{shift}+\theta_{unknown,speckle\ k})-\cos(\theta_{unknown,speckle\ k}))/2\pi(f_{shift}+M/2\pi) \quad [14]$$

If a Monte Carlo simulation is performed on the term [14] over many pixels, a distribution of pixel values will be generated, which will widen as M is increased. Assuming that $P_{reference} \gg P_{sample}$, the shot noise is largely determined by the term:

$$\sqrt{P_{reference}/f_{shift}}, \quad [15]$$

since this is the square root of the time-integrated intensity of $P_{reference}$, which is governed by Poisson statistics. Symbolically, for high signal to noise ratio, when using a camera with k pixels, the following equation, on average, needs to be satisfied:

$$(\cos(M/2\pi f_{shift}+\theta_{unknown,speckle\ k})-\cos(\theta_{unknown,speckle\ k}))/2\pi(f_{shift}+M/2\pi) \gg \sqrt{P_{reference}/f_{shift}}/\sqrt{k}. \quad [16]$$

Notably, Monte Carlo simulations are computer simulations based about a pseudo random number generator that models the random nature of light as it diffuses through a scattering medium, such as the human skull and brain.

Figure 21:
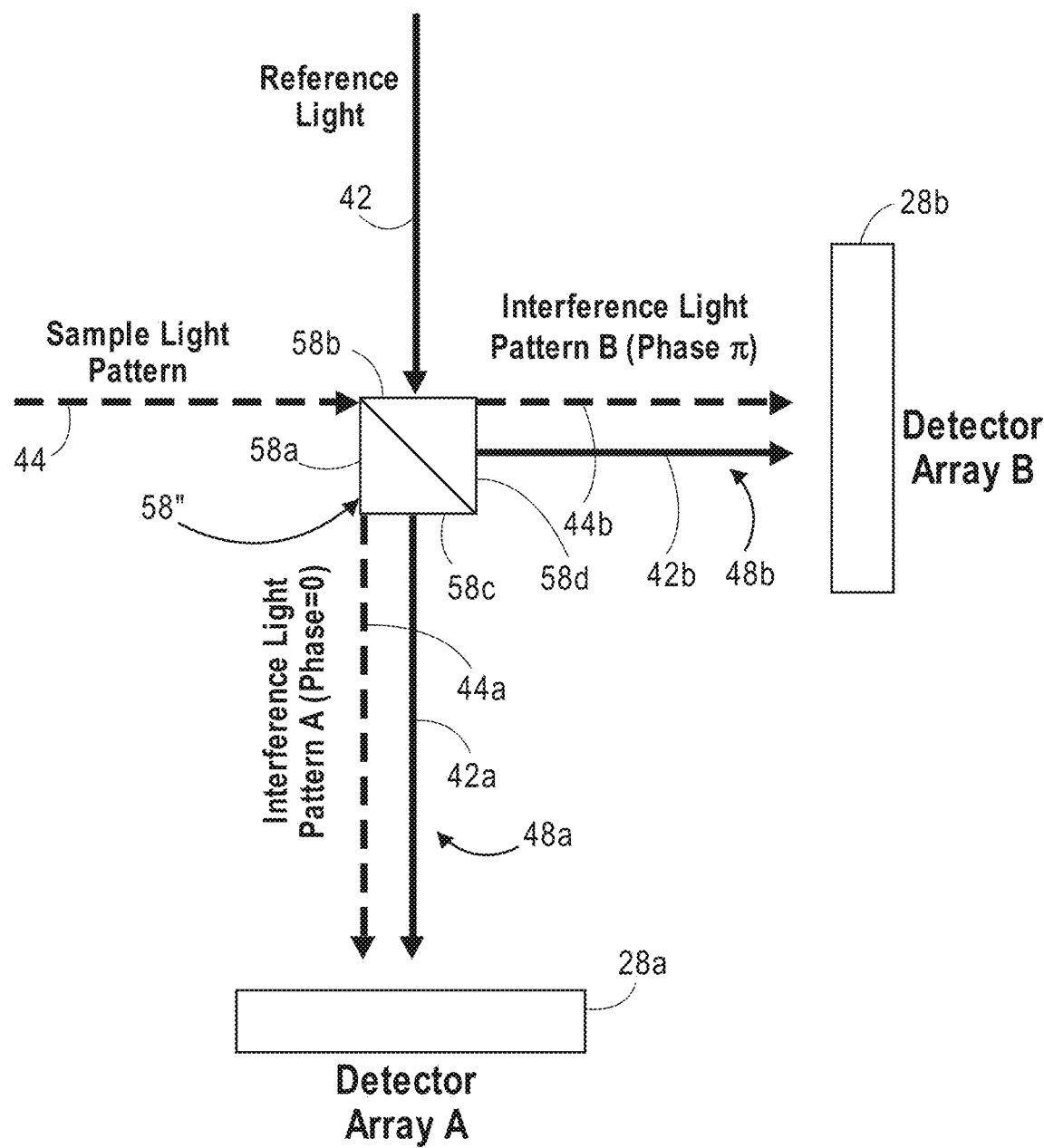
FIG. 21 is a block diagram of another specific embodiment of an interferometer and detector array that can be used in the non-invasive diffusive optical detection system of FIG. 8.

As also discussed above with respect to FIGS. 8 and 9a-9d, the interferometer may generate multiple phase-modulated interference light patterns 48 during each measurement period, in which case, multiple detector arrays 28 (e.g., multiple cameras or dedicated spatial regions of a single camera), and in this case, two detector arrays 28a, 28b are used, as illustrated in FIG. 21. The two detector arrays 28a and 28b are optically registered with each other to concurrently detect the two interference light patterns 48 over two phases. In this manner, two separate measurements of the target volume of interest 14 can be made simultaneously or in short succession by measuring the interference between the sample light pattern 44 and reference light 42 at two separate phases differing from each other by an angular phase of π.

A light splitter/combiner 58″ (which replaces the light splitter/combiner 58 illustrated in FIGS. 9a-9d) is configured for splitting the reference light 42 respectively into reference light 42a, 42b respectively having two different phases of 0 and π), splitting the sample light pattern 44 respectively into sample light pattern portions 44a and 44b, and concurrently combining the sample light pattern portions 44a and 44b with the reference light 42a and 42b to respectively generate two interference light patterns 48a ("Interference Light Pattern A"), 48b ("Interference Light Pattern B").

That is, the sample light pattern 44 enters an input port 58a of the beam splitter/combiner 58″, where it is split into a reflected sample light pattern portion 44a and a transmitted sample light pattern portion 44b, and the reference light 42 enters another input port 58b of the beam splitter/combiner 58″, where it is split into a transmitted reference light 42a and a reflected reference light 42b. In a simultaneous manner, the reflected sample light pattern portion 44a interferes with the transmitted reference light 42a to generate the interference light pattern 48a, and the transmitted sample light pattern portion 44b interferes with the reflected reference light 42b to generate the interference light pattern 48b.

Due to power conservation, a four-port network, such as the beam splitter/combiner 58″, requires the total power entering the input ports 58a, 58b to be equal to the total power exiting the output ports 58c, 58d, and thus, the transmitted reference light 42a will have a nominal phase of 0, and the reflected reference light 42b will have a phase of π. That is, as will be described in further detail below, since the combined power of the DC terms of the interference light patterns 48a, 48b exiting the respective output ports 58a, 58b of the beam splitter/combiner 58″ will be equal to the combined power of combined DC power of the sample light pattern 44 and reference light 42 respectively entering the input ports 58a, 58b of the beam splitter/combiner 58", the interfering AC beat pattern terms of the respective interference light patterns 48a, 48b will need to differ in phase by 180 degrees such that they sum to zero.

The detector array 28a ("Camera A") and detector array 28b ("Camera B") are respectively disposed at two output ports 58c, 58d of the beam splitter/combiner 58" for concurrently detecting the respective two interference light patterns 48a, 48b, and generating two pluralities of values representative of intensities of the spatial components ("speckle grains") of the respective two interference light patterns 48a, 48b. Thus, the sample light pattern 44 and reference light 42 combine to project an interference light pattern 48a onto the detector array 28a, and likewise to project an interference light pattern 48b onto the detector array 28b, but with respect to a different phase of the reference light 42. In the illustrated embodiment, the planes of the detector arrays 28a, 28b are perpendicular to each other, such that they face the respective output ports 58c, 58d of the beam splitter/combiner 58". The detector arrays 28a, 28b may be conventional in nature (e.g., readily available conventional charge-coupled device (CCD) cameras).

Figure 22:
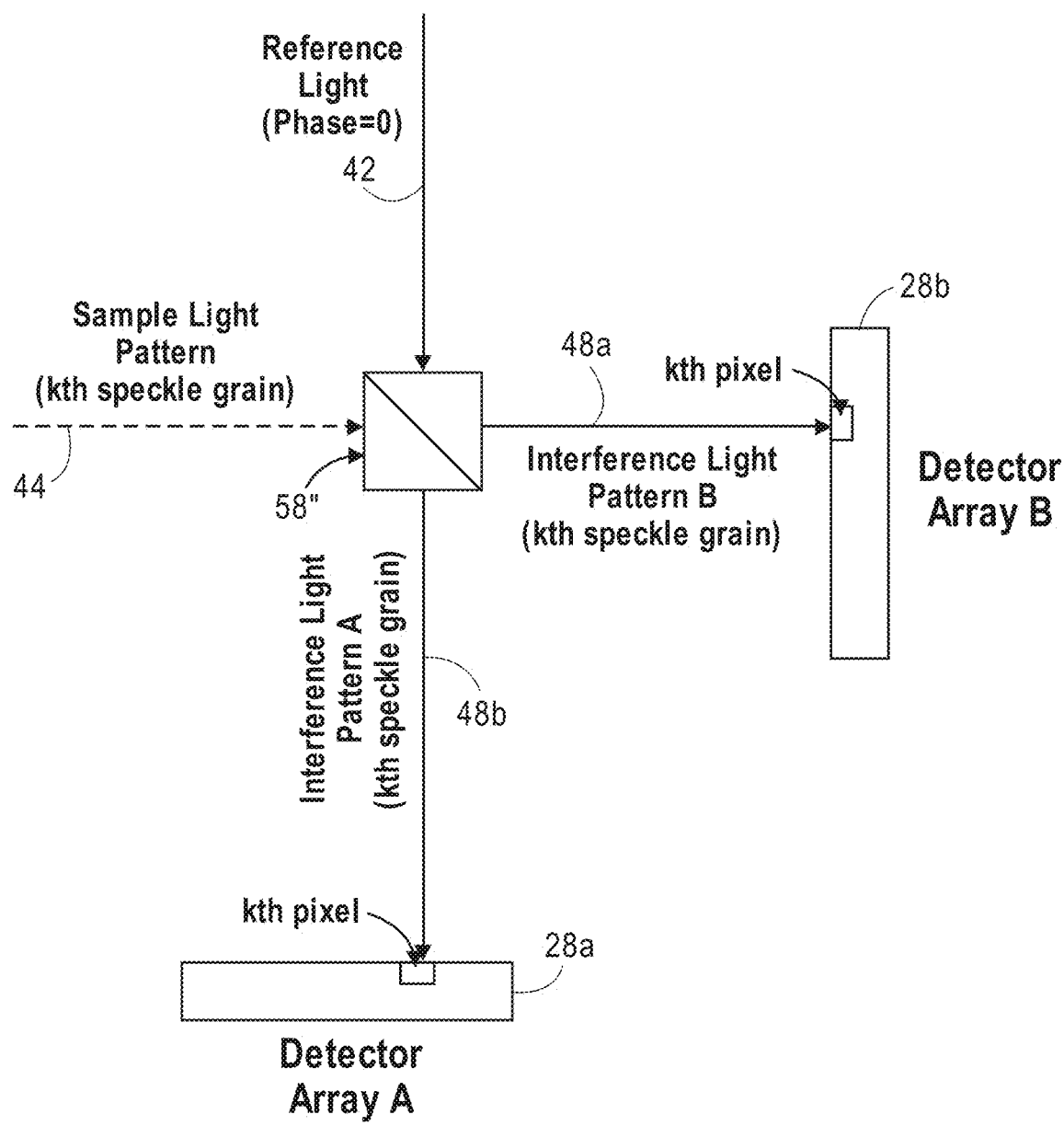
FIG. 22 is a block diagram of the interferometer and detector array of FIG. 21, particularly showing the generation and detection of kth speckle grains of two interference patterns.
Figure 23:
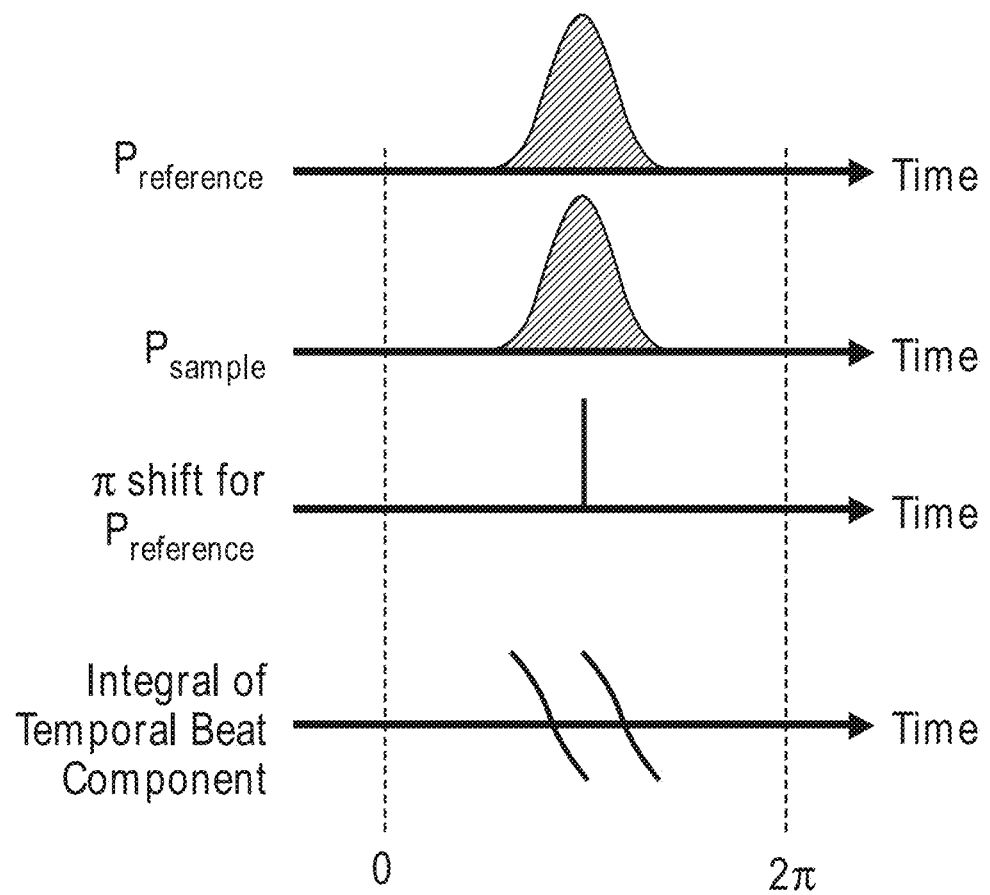
FIG. 23 is a timing diagram illustrating a relationship between a sample light pulse and a reference light pulse that can be in the non-invasive diffusive optical detection system of FIG. 8 to generate a temporal beat component that integrates to zero.

Although the detector arrays 28a, 28b are separate and distinct, the detector arrays 28a, 28b are optically aligned with each other, such that any given pixels on the detector arrays 28a, 28b have a known one-to-one correspondence with each other. That is, as illustrated in FIG. 22, a spatial component of the sample light pattern 44 (i.e., the kth speckle grain of the speckle light field) interferes with the reference light 42 with no phase shift (i.e., 0) to generate a kth speckle grain of the interference light pattern 48a that is detected by kth pixel of the detector array 28a, and the same kth speckle grain of the sample light pattern 44 interferes with the reference light 42 with a phase shift (i.e., $\pi$) to generate a corresponding kth speckle grain of the interference light pattern 48b that is detected by the corresponding kth pixel of the detector array 28b. Since the kth pixel of the detector array 28a has a known correspondence via optical alignment with the kth pixel of the detector array 28b, the pair of intensity values detected by the kth pixels of the cameras 28a, 28b are both representative of the kth speckle grain of the sample light pattern 44, but at different phases. It should be appreciated that although FIG. 22 illustrates one speckle grain "k," an equivalent process for measuring the speckle grain k takes place for all speckle grains in parallel in the manner of measuring an entire speckle light field.

At each corresponding pair of kth pixels, the optical power received by the respective detector arrays 28a, 28b is equal to the summation of the power of the reference light 42 ($P_{reference}A$ and $P_{reference}B$) input into the beam splitter/combiner 58", the sample light pattern 44 ($P_{sample}A$ and $P_{sample}B$) input into the beam splitter/combiner 58", and an interference term between the reference light 42 and sample light pattern 44 ($P_{interfere}A$ and $P_{interfere}B$). By the power conservation, the interference terms $P_{interfere}A$ and $P_{interfere}B$ are 180 degrees out of phase for the cameras 28a, 28b.

Although two distinct detector arrays 28a, 28b have been described, two distinct camera regions on a single camera can be used for detecting the two interference patterns 48a, 48b. Further details discussing different systems for simultaneously detecting an M number of interference light patterns are described in U.S. patent application Ser. No. 15/853,209, entitled "System and Method for Simultaneously Detecting Phase Modulated Optical Signals" (now U.S. Pat. No. 10,016,137), which is expressly incorporated herein by reference.

Just as with the single detector array case described above, it is desirable that the pulsed waveform of the sample light 40 and the frequency offset $f_{shift}$ between the sample light 40 and the reference light 42 be selected, such that the temporal beat component of each of the respective interference light patterns 48a, 48b illustrated in FIG. 21 integrates to a zero value in the absence of a fast-optical signal in the target volume of interest 14, resulting in a relatively narrow intensity population distribution across the pixels 68 of the respective detector array 28, and integrates to a non-zero value in the present of a fast-optical signal in the target volume of interest 14, resulting in a relatively broad intensity population distribution across the pixels 68 of the respective detector array 28. It should also be appreciated that use of the beam splitter/combiner 58" and two detector arrays 28 provides a convenient means of subtracting two interference light patterns 48a, 48b from each other to eliminate the noise contributed by the DC terms of the sample light pattern 44 and reference light 44, thereby minimizing the spread of the resulting intensity population distribution in the absence of a fast-optical signal in the target volume of interest 14.

In particular, assuming a frequency offset between the sample light 40 and the reference light 42 of $f_{shift}$, the intensity of the interference light pattern 48a detected at a kth pixel of the first camera 228a can be expressed as:

$$\text{Value}_{1,k} = \int_{t_0}^{t_1} (P_{sample}(t) + P_{reference}(t) + 2\sqrt{P_{sample}(t) \times P_{reference}(t)} \times (\sin(2\pi(-f_{shift})t + \theta_{unknown, speckle\ k} + 2\pi \times \delta/\lambda))) dt, \quad [17]$$

and likewise the intensity of the interference light pattern 48b detected at a kth pixel of the second camera 228b can be expressed as:

$$\text{Value}_{2,k} = \int_{t_0}^{t_1} (P_{sample}(t) + 2\sqrt{P_{sample}(t) \times P_{reference}(t)} \times (\sin(2\pi(-f_{shift})t + \theta_{unknown, speckle\ k} + 2\pi \times \delta/\lambda))) dt, \quad [18]$$

where $P_{sample}$ represents sample light 40 as a function of time t, $P_{reference}$ represents the reference light 42 as a function of time t, $t_0$ is the beginning of the measurement period, $t_1$ is the end of the measurement period, $\theta_{unknown, speckle\ k}$ is a random phase at the kth speckle grain of the speckle light pattern at the time of measurement by the respective detector arrays 28a, 28b, which originate via multiple scattering of coherent light inside the tissue; and $\delta$ is the average path length shift of the sample light 40 (sample arm) due to fast-optical signals in the target volume of interest 14, assuming the reference light 42 (reference arm) has a fixed path length.

The temporal beat components in equations [17] and [18] can be respectively represented as:

[19]
$$2\sqrt{P_{sample}(t) \times P_{reference}(t)} \times (\sin(2\pi(-f_{shift})t + \theta_{unknown, speckle\ k} + 2\pi \times \delta t/\lambda));$$

and

[20]
$$2\sqrt{P_{sample}(t) \times P_{reference}(t)} \times (\sin(2\pi(-f_{shift})t + \theta_{unknown, speckle\ k} + \pi + 2\pi \times \delta \times t/\lambda)).$$

Assuming the absence of a fast-optical signal, the average path length shift of the sample light 40 in the target volume of interest 14 will be constant, and thus, the average path length shift of the sample light $\delta$ will be equal to zero. In this case, the temporal beat component [19] and [20] will reduce to:

$$[21]\ 2\sqrt{P_{sample}(t) \times P_{reference}(t)} \times (\sin(2\pi(-f_{shift})t + \theta_{unknown, speckle\ k}));$$

and $$[22]\ 2\sqrt{P_{sample}(t) \times P_{reference}(t)} \times (\sin(2\pi(-f_{shift})t + \pi + \theta_{unknown, speckle\ k}));$$

As discussed above, it is desirable that the temporal beat components of the interference light patterns 48a, 48b integrate to zero for all for all possible values of the unknown phase $\theta_{unknown}$, and thus for all pixels k in the detector arrays 28a, 28b, in the absence of a fast-optical signal. As a general rule, a function of the shape of the pulsed waveforms for the sample light 40 and the frequency offset $f_{shift}$ between the sample light 40 and the reference light 42 can be selected in accordance with the following equation, such that each of the temporal beat components [21] and [22] always integrates to zero, as follows:

$$[23]\ \int_{t_0}^{t_2} \sqrt{P_{sample}(t) * P_{reference}(t)} \times \sin(2\pi f_{shift} + \theta_{unknown, speckle\ k}) dt = 0;$$

and $$[24]\ \int_{t_0}^{t_2} \sqrt{P_{sample}(t) * P_{reference}(t)} \times \sin(2\pi f_{shift} + \pi + \theta_{unknown, speckle\ k}) dt = 0.$$

As described above with respect to equation [4], if the sample light 40 has a single rectangular pulse per measurement period, equations [23] and [24] will be satisfied if the duration of the pulse $T_{op}$, and the frequency offset $f_{shift}$ between the sample light 40 and the reference light 42 are selected in accordance with equation [7]. If the pulsed waveform of the sample light 40 includes two identical pulses per measurement period, equations [23] and [24] will be satisfied if the distance between the two pulses are selected in accordance with equation [8]. Furthermore, with reference to FIG. 23, for a single symmetrical pulse (rectangular or otherwise), as long as there is a 180-degree phase shift between the reference light 42 and the sample light pattern 44, equations [23] and [24], such that the temporal beat components will integrate to zero.

Because the terms $P_{sample}$ and $P_{reference}$ are constant across the two detector arrays 28a, 28b, they can be eliminated by taking the difference of the intensity values $\text{Value}_{1,k}$ and $\text{Value}_{2,k}$ and since the temporal beat components [23] and [24] of the interference light patterns 48a, 48b integrate to zero, the net number of photo electrons detected by the detector arrays 28a, 28b will be zero in the absence of a fast-optical signal in the target volume of interest 14. It should be appreciated that the elimination of the DC components $P_{sample}$ and $P_{reference}$ by taking the difference of the intensity values $\text{Value}_{1,k}$ and $\text{Value}_{2,k}$ decreases the noise in the resulting signal, thereby minimizing the spread of the intensity population distribution when the interferometer 22 is balanced.

Assuming the presence of a fast-optical signal, the average path length shift of the sample light 40 in the target volume of interest 14 will vary in a manner reflective of the dynamics of the fast-optical signal and hence functional (e.g., neural) activity in the target volume of interest 14. As a result, the average path length shift of the sample light δ in equations [19] and [20] will no longer be equal to zero. Consequently, the intensity of the temporal beat components [19] and [20] will be a non-zero value, which may be represented by a signal S/2 for the detector array 28a and a signal −S/2 for the detector array 28b due to the 180-degree phase offset built into the temporal beat components [19] and [20] by the interferometer 22.

Thus, the intensity of the interference light pattern 48a detected at a kth pixel of the first detector array 28a is:

$$\text{Value}_{1,k} = P_{sample} + P_{reference} + S/2, \quad [25]$$

and the intensity of the interference light pattern 48b detected at a kth pixel of the first detector array 28b is:

$$\text{Value}_{2,k} = P_{sample} + P_{reference} - S/2. \quad [26]$$

Taking the difference between the intensity values $\text{Value}_{1,k}$ and $\text{Value}_{2,k}$ provides:

$$\text{Value}_{1,k} - \text{Value}_{2,k} = (P_{sample} + P_{reference} + S/2) - (P_{sample} + P_{reference} - S/2) = S \text{ (or } -S \text{ if } S \text{ was negative)}. \quad [27]$$

As discussed above with respect to the single detector array 28, the signal S is largely correlated to the fast-optical signal in the target volume of interest 14. That is, since the intensity of the temporal beat components [19] and [20] were set to zero (or approximately zero) in the absence of a fast-optical signal, the signal S will be strongly correlated to the path length term (2πxδ/λ) of the temporal beat components [19] and [20] by the fast-optical signal. Such signal S will potentially be different for each speckle grain or pixel. As the signal S increases, the spread of the intensity population distribution likewise increases in the same manner described above in the single detector array case, with the exception that the noise will be reduced here by the elimination of the DC components $P_{sample}$ and $P_{reference}$.

Regardless of the number of detector arrays 28 and interference light patterns 48 generated, the diffusive optical detection system 10 is sensitive to stability of the waveform shape of the sample light 40 (including pulse amplitude, duration, and phase) and the frequency offset $f_{shift}$ between the sample light 40 and the reference light 42. To ensure that the interferometer 22 remains "balanced" in the absence of a fast-optical signal, the diffusive optical detection system 10 may optionally comprise highly stable sensors (not shown) for monitoring the waveform shape of the sample light 40 and the frequency offset $f_{shift}$. For example, such sensors can be placed at the output of the light source 50 and in the path of the sample arm or reference arm after the frequency shifter 56 for respectively measuring the waveform shape of the sample light 40 and the frequency offset $f_{shift}$. Based on the data received by the sensors, the controller 24 sends the appropriate control signals to the light source 50 and frequency shifter 56 to maintain the optimal wave shape of the sample light 50 and frequency offset $f_{shift}$ between the sample light 40 and the reference light 42, such that linearity in the intensity population distribution response and the maximum signal-to-noise ratio is maintained. The controller 24 may repeatedly control the light source 50 and frequency shifter 56 in response to the data received by the sensors several times, e.g., tens of times per second.

Alternatively, rather than sensing the inputs to the light splitter/combiner 58 (in this case, in the sample arm or reference arm of the interferometer 22), the output of the light splitter/combiner 58 may be monitored. For example, during a known period where there is an absence of a fast-optical signal in the target volume of interest 14, the controller 24 may monitor the signal S extracted from the interference light pattern 48 (i.e., the integral of the temporal beat component [2]) by the processor 26, and then send the appropriate control signals to the light source 50 and frequency shifter 56 to minimize the signal S ("zeroed out")

using a feedback technique, such as proportional integration differential control, thereby maximizing the signal-to-noise ratio (SNR) given the dynamic range of the detector array(s) 28.

In an optional embodiment, instead of analyzing the breadth of the intensity population distribution of the function of the spatial components of the interference light pattern(s) 48 to identify a fast-optical signal in the target volume of interest 14, the processor 26 may treat the driving terms in this feedback control mechanism as a measure of the fast-optical signal. For example, the processor 26 may examine the amount of "effort" that must be exerted by the controller 24 to minimize the integral of the temporal beat pattern; e.g., the extent to which the controller 24 must modify the present waveform shape of the sample light 40 or the frequency offset $f_{shift}$ between the sample light 40 and the reference light 42, and identify, based on this "effort" the presence of a fast-optical signal in the target volume of interest 14.

Alternatively, the sign of the change back and forth may be alternated by changing N to eliminate the need to zero out the interferometer 22 in the absence of a fast-optical signal in the target volume of interest 14.

In addition to identifying the presence of a fast-optical signal by interferometrically extracting the temporal beat component (the "AC component"), the processor 26, in an optional embodiment, may be configured for extracting the DC component (i.e., $P_{sample}+P_{reference}$) from equation [1]. Because the power of the reference light $P_{reference}$ is known or independently measurable, the DC component $P_{sample}+P_{reference}$ serves as a measurement of the power of the sample light $P_{sample}$. Thus, using a known scaling relationship, the power of the sample light $P_{sample}$ can be determined (either in the absolute sense or relative sense) from the extracted DC component $P_{sample}+P_{reference}$. In a similar manner used by a conventional diffuse optical tomography (DOT) or Functional Near-Infrared Spectroscopy (fNIRS) systems, the sample light $P_{sample}$ extracted from equation [1] may be used to measure slow light absorption in the target volume of interest 14, e.g., due to hemodynamics. Thus, the optional diffusive optical detection system 10 may be used to measure both fast-optical signals and slower hemodynamic signals in the target volume of interest 14.

In another optional embodiment, the interferometer 22 may be incorporated into a pulsed ultrasound modulating optical tomography (UOT) system, such as those described in U.S. patent application Ser. No. 16/266,818, entitled "Ultrasound Modulating Optical Tomography Using Reduced Laser Pulse Duration," which is expressly incorporated herein by reference. In this embodiment, instead of detecting fast-optical signals in the target volume of interest 14, another type of optical perturbation, and in particular, optical perturbations caused by the propagation of ultrasound through the target volume of interest 14 can be detected. Thus, the interferometer 22 of this pulsed UOT system can be "balanced," such that the temporal beat component integrates to zero in the absence of the ultrasound within the target volume of interest 14, resulting in a relatively narrow intensity population distribution. The optical perturbations caused by the ultrasound focused on the target volume of interest 14 will cause the interferometer 22 to become "unbalanced," such that the temporal beat component integrates to a non-zero value, resulting in a relatively broad intensity population distribution. Variability in the intensity population distribution over several measurements using the same ultrasound parameters over a single ultrasound pulse indicates the presence of a physiologically dependent optical parameter within the target volume of interest 14. This technique allows the duration of pulses of the sample light 40 to be set independently of the duration of the ultrasound pulse in a pulsed UOT system that utilizes the interferometer 22.

Referring now to FIG. 24, the physical implementation of the non-invasive diffusive optical detection system 10 will be described. As there shown, the non-invasive diffusive optical detection system 10 includes a wearable unit 90 that is configured for being applied to a user 18, and in this case, worn on the head 16 of the user 18; an auxiliary head-worn or not head-worn unit 92 (e.g., worn on the neck, shoulders, chest, or arm, or integrated within the housing or support structure 97 of the wearable unit 90) coupled to the wearable unit 90 via a wired connection 93 (e.g., electrical wires); and an optional remote processor 94 in communication with the patient-wearable auxiliary unit 92 coupled via a wireless connection 95 (e.g., electrical wires). Alternatively, the non-invasive diffusive optical detection system 10 may use a non-wired connection (e.g., wireless radio frequency (RF) signals) for providing power to or communicating between the respective wearable unit 90 and the auxiliary unit 92, and/or a wired connection between the auxiliary unit 92 and the remote processor 94.

In the illustrated embodiment, the wearable unit 90 includes a support structure 97 that either contains or carries the interferometer 22 and the detector array(s) 28 (shown in FIGS. 9a-9d). The wearable unit 90 may also include an output port 98a from which the sample light 40 generated by the interferometer 22 is emitted (from the light source 50), and an input port 98b into which the sample light pattern 44 is input into the interferometer 22 (received by the detector array(s) 28). It should be appreciated that although the input port 98b is illustrated in close proximity to the input port 98a, the proximity between the input port 98b and the output port 98a may be any suitable distance. The support structure 97 may be shaped, e.g., have a banana, headband, cap, helmet, beanie, or other hat shape, or other shape adjustable and comfortable to the user's head 16, such that the ports 98a and 98b are in close contact with the outer skin of the body part, and in this case, the scalp of the head 16 of the person 18. The Support structure 97 of the wearable unit 90 may be made out of any suitable cloth, soft polymer, plastic, hard shell, and/or any other suitable material as may serve a particular implementation. An index matching fluid maybe used to reduce reflection of the light generated by the light source 50 of the interferometer 22 from the outer skin. An adhesive, strap, or belt (not shown) can be used to secure the support structure 94 to the head 16 of the user 18.

The auxiliary unit 92 includes a housing 99 that contains the computing device 23 with controller 24 and the processor 26 (shown in FIG. 8). In some embodiments, portions of the controller 24 and processor 26 may be integrated within the wearable unit 90. The auxiliary unit 92 may additionally include a power supply (which if head-worn, may take the form of a rechargeable or non-chargeable battery), a control panel with input/output functions, a display, and memory. Alternatively, power may be provided to the auxiliary unit 92 wirelessly (e.g., by induction). The auxiliary unit 92 may further include any drive circuitry used to operate the interferometer 22. The remote processor 94 may store detected data from previous sessions, log as a history data, and include a display screen as described above.

Figure 25:
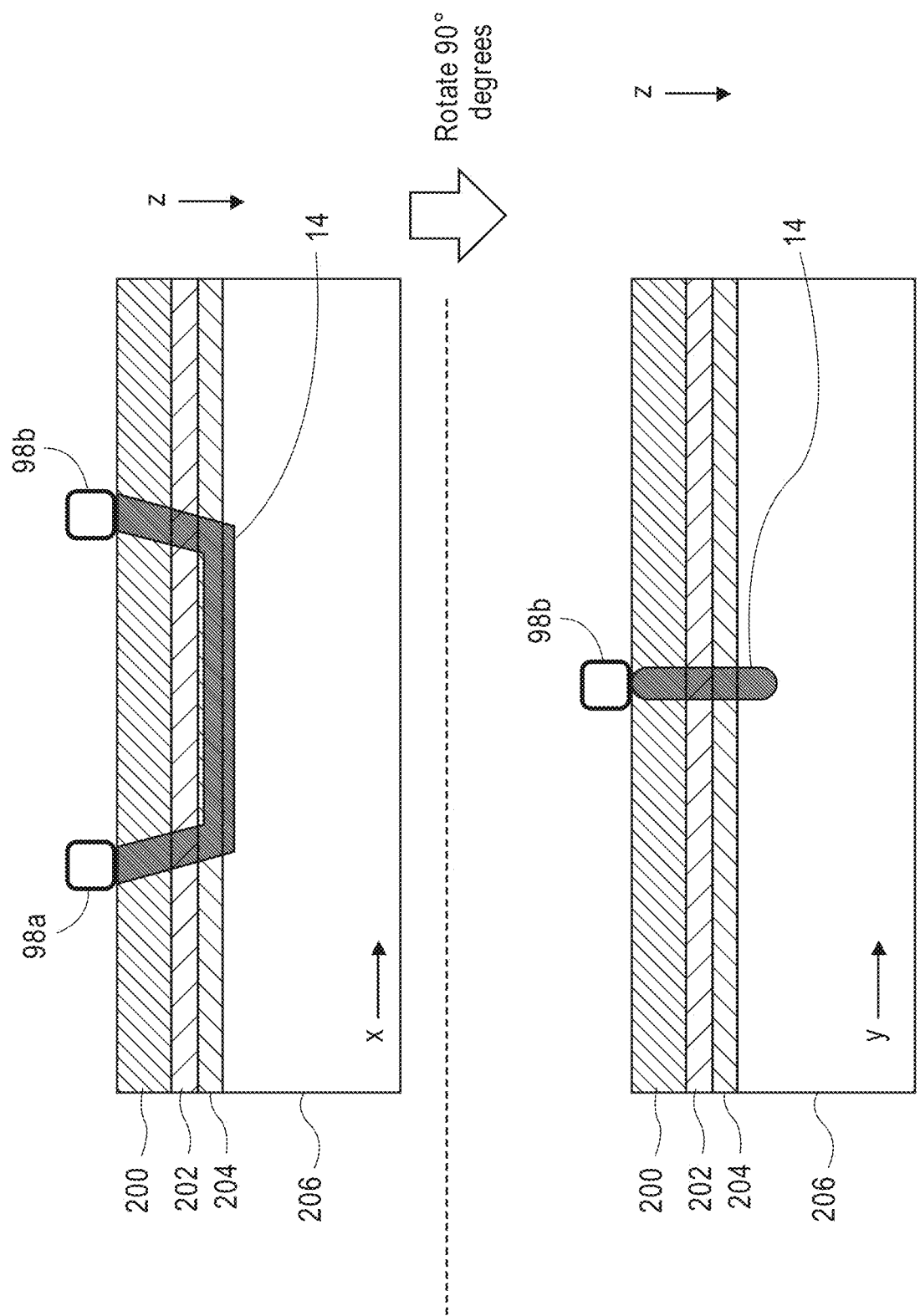
FIG. 25 are profile views of one arrangement of the output port and input port of the wearable unit of FIG. 24, particularly illustrating the creation of a target volume of interest within tissue between the ports.

It should be appreciated that because the non-invasive diffusive optical detection system 10, for purposes of brevity, has been described as comprising a single fixed source-detector pair, in other words, a single output port 98a and a single input port 98b, it can only identify a fast-optical signal in a single volume of interest 14 between the ports 98a, 98b, as illustrated in FIG. 25. The ports 98a, 98b are placed against the scalp 200 to measure regions of interest in the skull 202, cerebral spinal fluid (CS F) 204, and/or cortical brain tissue 206. The various optical paths may first pass through the scalp 200 and skull 202 along a relatively straight path, briefly enter the brain tissue 206, then exit along a relatively straight path. In effect, this creates a volume of interest 14 (defined by the light path between the ports 98a, 98b) that is banana-shaped in that it extends along the Z-direction and across an X-Y plane, as depicted in FIG. 25. The reference arm in the interferometer 22 may be selected or adjusted (as described above with respect to FIG. 9a) based on the distance between the ports 98a, 98b, and the depth of the target volume of interest 14, and may, e.g., be approximately (or greater than) the sum of the distance between the ports 98a, 98b and twice the depth of the target volume of interest 14. As depicted in top half of FIG. 25, the greater distance of the target volume of interest 14 may be across the X-Y plane as compared to its distance along the Z-direction.

In optional embodiments, the diffusive optical detection system 10 may be modified, such that it can sequentially or simultaneously identify fast-optical signals in multiple tissue volumes 14 by tiling multiple source-detector pairs across the scalp 200. In this case, each tissue volume 14 is defined by a given output port 98a (which is associated with the light source 50) at a given location and a given input port 98b (which is associated with the detector array(s) 28) at a given location. Thus, multiple tissue volumes 14 can be measured either by making the output port 98a movable relative to the input port 98b and/or spacing multiple input ports 98b from each other.

Figure 26:
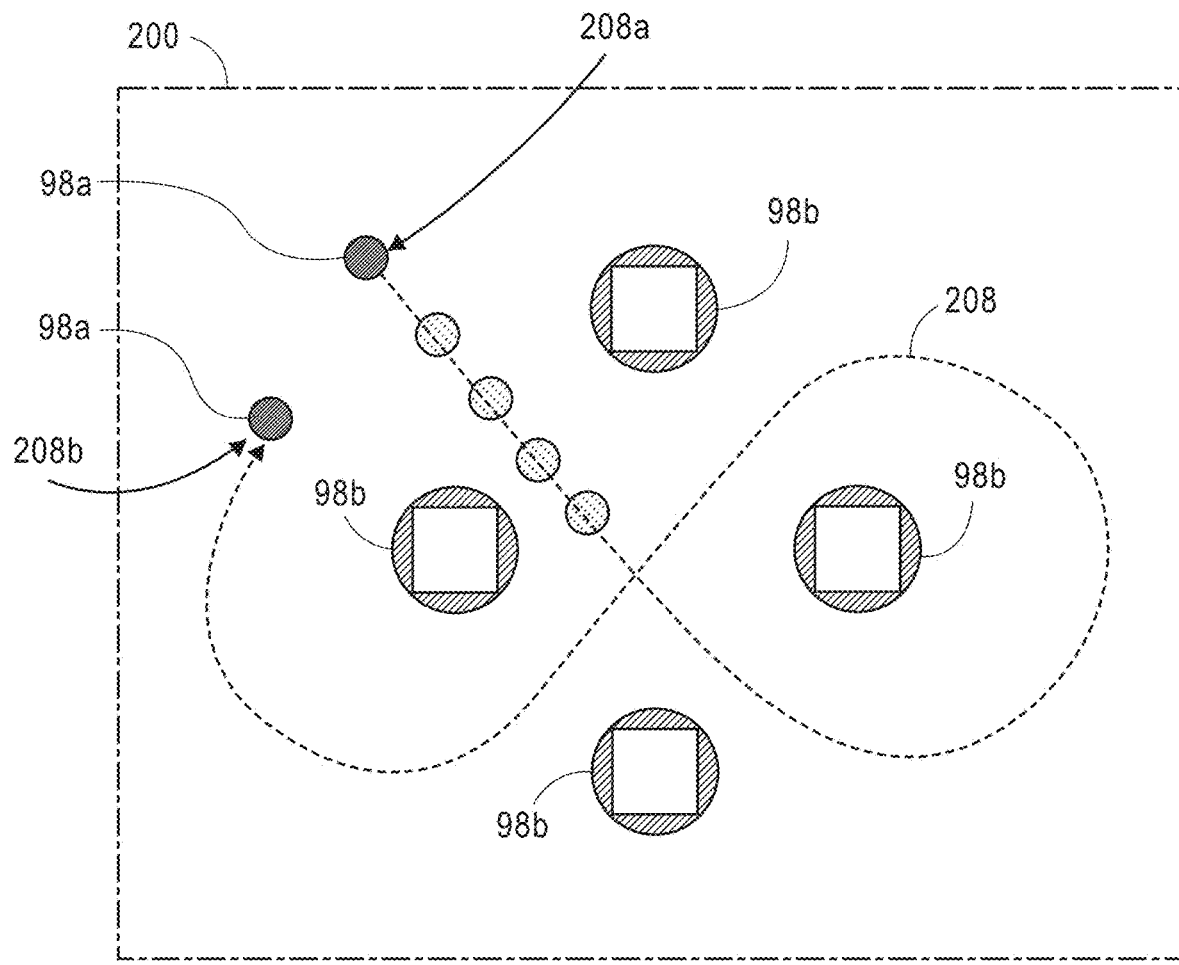
FIG. 26 is a plan view illustrating a modified arrangement of one movable output port and a multitude of fixed input ports that can be used in the wearable unit of FIG. 24, particularly illustrating a path along which the output port is moved around the input ports.

For example, with reference to FIG. 26, a plurality of input ports 98b are located at fixed positions on the scalp 200, and a single movable output port 98a may be moved around at different locations across the scalp 200 along a predetermined path 208 (e.g., from a first location 208a to a second location 208b) around the input ports 98b to distribute light into the target volume of interest 14 from various locations on the surface of scalp 200. The input ports 98b may be arranged in any desirable pattern over the scalp 200. For example, they may be arranged or located in a symmetric or asymmetric array and/or may be arranged in a circular or radial pattern or a rectangular-shaped pattern. The field of view of the input ports 98b may have areas of overlap and/or may have little or no overlap. In some variations, the input ports 98b may be tiled adjacent to each other, such that the individual fields-of-view are adjacent to each other with little or no overlap. The aggregate of the individual fields-of-view may simulate a single camera with a large field-of-view.

Figure 27:
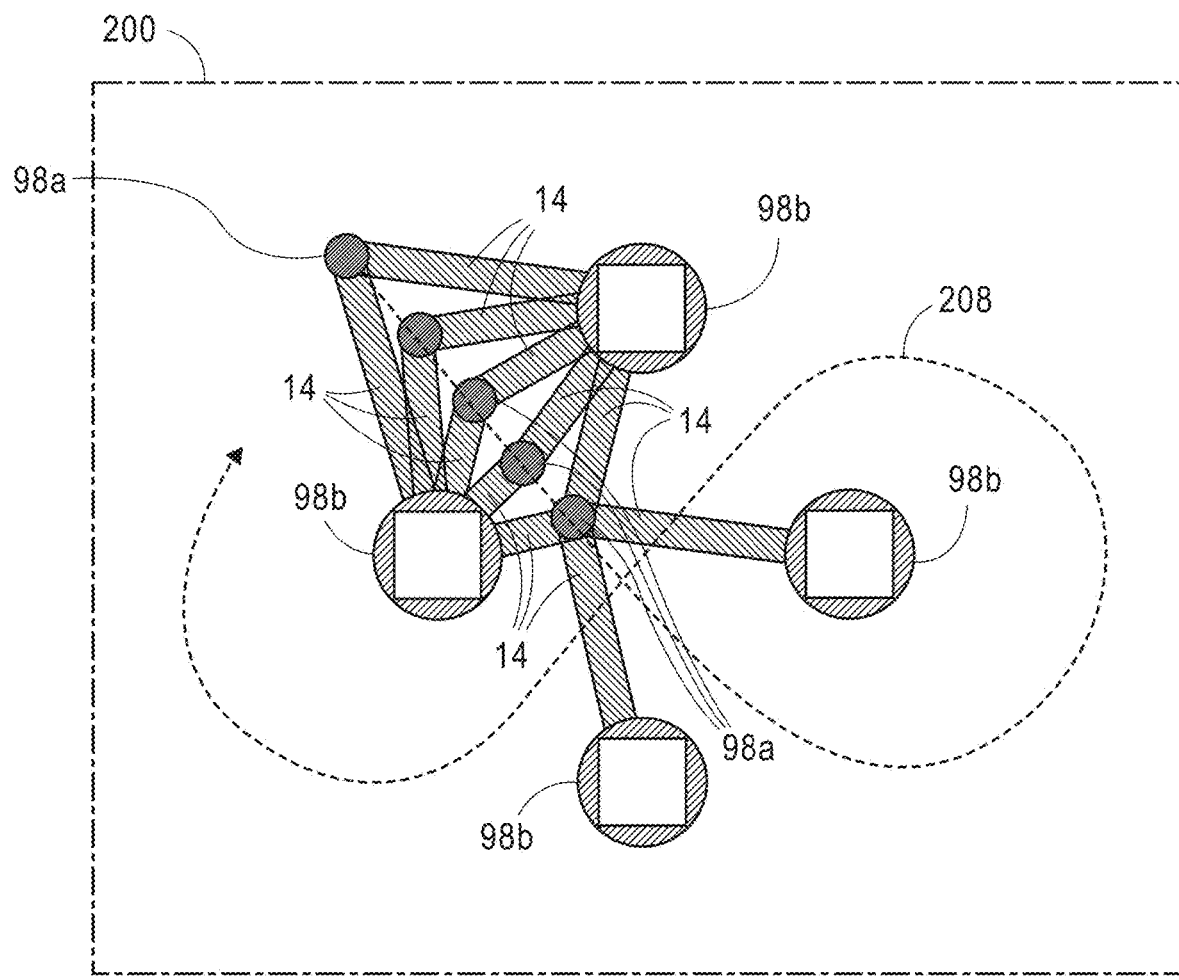
FIG. 27 is a plan view illustrating the modified arrangement of FIG. 26, particularly illustrating the creation of multiple volumes of interest within tissue between the ports.

In any arrangement, the light emitted by the output port 98a may be reflected and/or backscattered to the scalp 200 and enter the plurality of input ports 98b. In effect, this creates a multitude of tissue volumes 14 through the brain tissue 206 (shown in FIG. 25) under the scalp 200 that are detected while the output port 98a moves along the path 208, as illustrated in FIG. 27. The multiple "criss-crossed" tissue volumes 14 may facilitate the generation of a high-resolution functional map of the upper layer of cortex of the brain 206 with spatial resolution given by the XY plane (i.e., along the plane of the scalp 200) confinement of the paths and not limited by their lower Z confinement, in the manner of tomographic volume reconstruction, and in this method, defining the lateral cross-section of a bundle of tissue volumes as X-Y and the axial direction along Z. Moreover, moving the output port 98a with respect to the input ports 98b at one or more pre-determined locations may probe a region of interest from multiple angles and directions. That is, the output port 98a will be create multiple target tissue volumes extending from the pre-determined location to the multiple input ports 98b, allowing optical data from the pre-determined location at the origin of the multiple tissue volumes to be measured along multiple axes. Optical data taken across multiple axis across a region of interest may facilitate the generation of a 3-D map of the region of interest, such as from the tissue volume. Optical data received by the input ports 98b may be used to generate measurements with comparable resolution in the Z-direction (i.e., perpendicular to a scalp 200 as in the X-Y plane (i.e., along the scalp 200), and/or may allow optical probing or interrogation of larger regions in brain tissue 206 (e.g., across multiple tissue volumes over a surface of the scalp).

Figure 28:
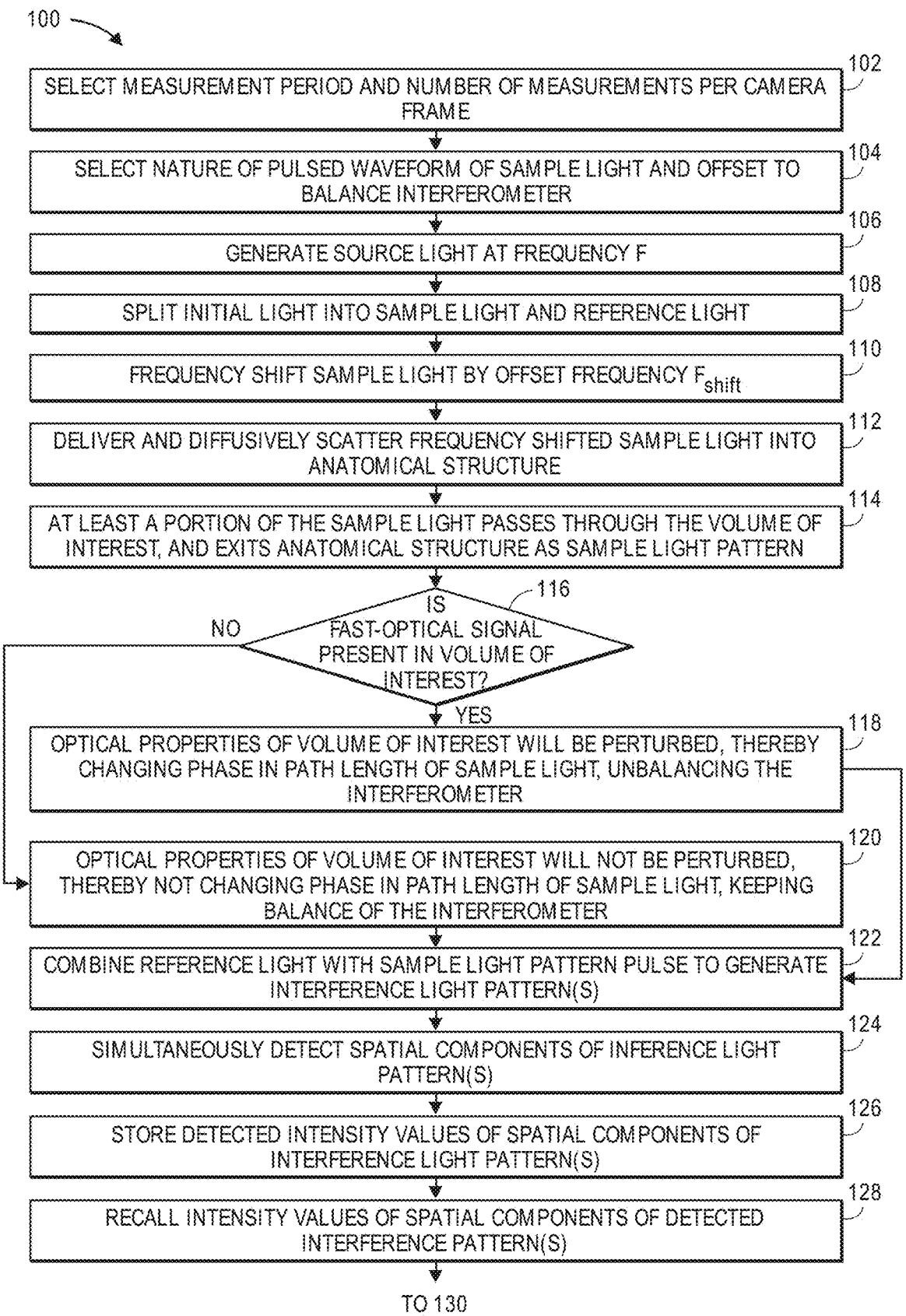
FIG. 28 is a flow diagram of one method used by the non-invasive diffusive optical detection system of FIG. 8 to non-invasively detect a fast-optical signal in brain tissue.
Figure 28:
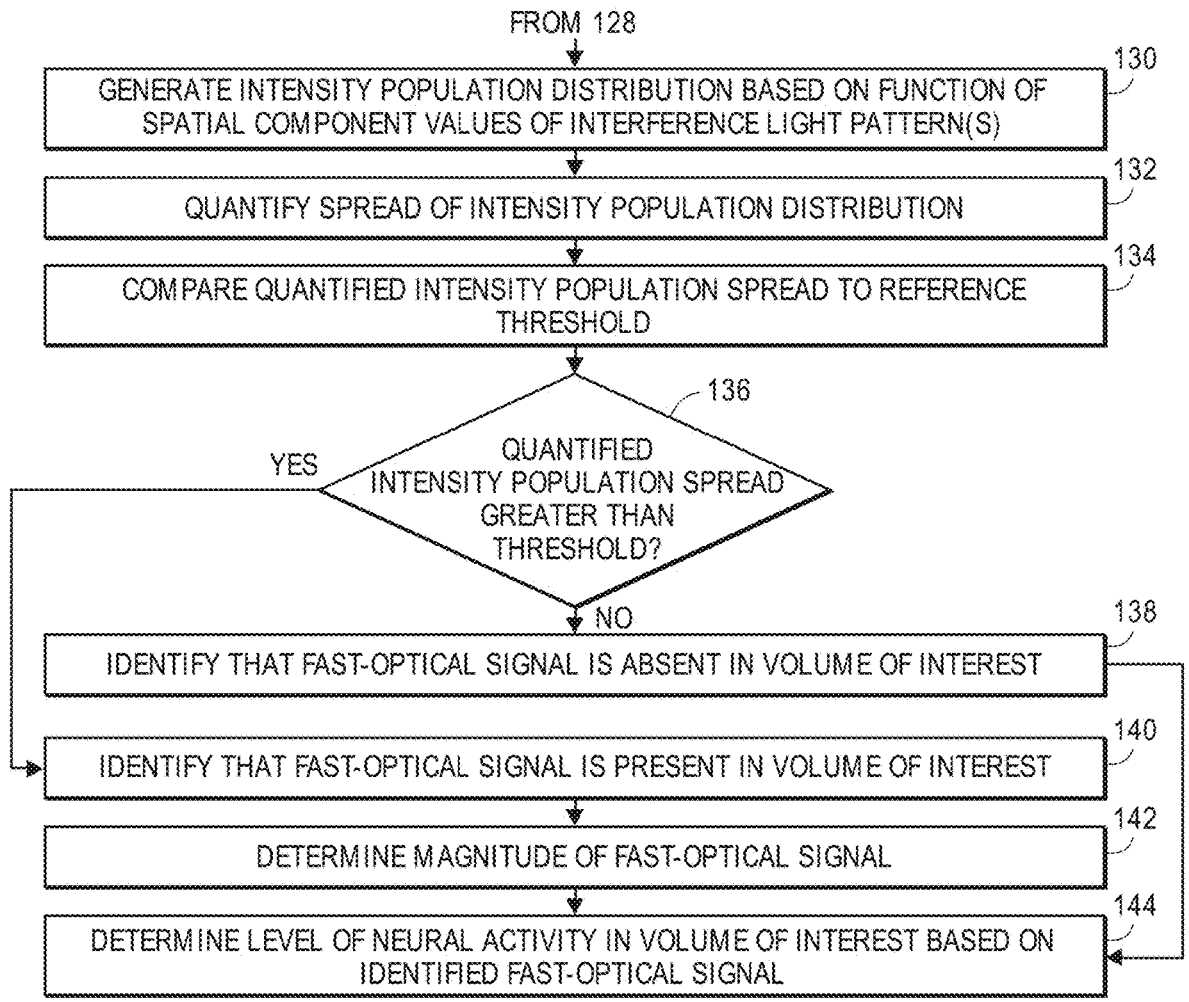

Referring to FIG. 28, having described the structure and function of the non-invasive diffusive optical detection system 10, one particular method 100 performed by the diffusive optical detection system 10 to non-invasively measure and/or detect a single tissue target volume of interest 14 in an anatomical structure (and in this case, the user's head 16) will now be described. Prior to operating the non-invasive diffusive optical detection system 10, the measurement period of the diffusive optical system 10, as well as number of measurement periods per camera frame, are selected with due consideration to the decorrelation time of the target volume of interest 14 and the duration of the physiological event (in this case, a fast-optical signal) to be detected (step 102). For example, the measurement period can be selected to be less than both the decorrelation time and the expected duration of the physiological event in the manner described above with respect to FIGS. 12 and 13, and the number of measurements per camera frame can be selected in the manner described above with respect to FIG. 14. Next, the nature of the pulsed waveform of the sample light 40 (including pulse shape, pulse width, and number of pulses per measurement period), as well the frequency shift $f_{shift}$ between the sample light 40 and the reference light 42, are selected such that the temporal beat component of the interference light pattern 48 integrates to zero in accordance with equation [4] for a single interference light pattern 48 or equations [23] and [24] for two phase modulated interference light patterns 48, thereby "balancing" the interferometer 22 (step 104).

After the design parameters of the diffusive optical detection system 10 are set, the controller 24 operates the interferometer 22 to generate and emit source light 38 having a frequency f, e.g., by sending a control signal to the drive circuit to pulse the light source 50 on and off (step 106). The interferometer 22 (e.g., via the beam splitter 52) splits the source light 38 into sample light 40 and reference light 42 (step 108).

Next, prior to the sample light 40 entering the anatomical structure 16, the controller 24 operates the interferometer 22 to frequency shift the sample light 40 by the frequency offset $f_{shift}$, e.g., by sending a control signal to the frequency shifter 56, resulting in the sample light 40 having a frequency $f-f_{shift}$ (step 110). It should be appreciated that, although this frequency shifting technique implements the frequency shifting technique illustrated in FIG. 9a, other frequency shifting techniques can be utilized, such as those illustrated in FIGS. 9b-9d.

The frequency-shifted sample light 40 is then delivered into and diffusively scattered within the anatomical structure 16 (step 112). As the frequency shifted sample light 40 scatters diffusively through the anatomical structure 16, at least a portion will pass through the target volume of interest 14, and exits the anatomical structure 16 as a sample light pattern 44 (step 114). If the physiological event (in this case, a fast-optical signal) is present in the target volume of interest 14 (step 116), the optical properties of the target volume of interest 14 will be perturbed, thereby changing phase in the path length of the sample light 40, and unbalancing the interferometer 22 (step 118). If, on the other hand, the physiological event is absent in the target volume of interest 14 (step 116), the optical properties of the target volume of interest 14 will not be perturbed, thereby not changing the phase in the path length of the sample light 40, such that the interferometer 22 remains balanced (step 120).

Next, the interferometer 22 then combines (e.g., via the light combiner 58) the reference light 42 with the sample light pattern 44 to generate one or more interference light patterns 48 (step 122). For example, the single interference light pattern 48 illustrated in FIGS. 18 and 19 can be generated using the light combiner 58', two phase modulated interference light patterns 48a, 48b illustrated in FIGS. 21 and 22 can be generated using the light splitter/combiner 58".

Then, under control of the controller 24, all of the detectors 68 of the detector array(s) 28 simultaneously detect respective spatial components of the interference light pattern(s) 48 (i.e., speckle grains in the case where the interference light pattern(s) includes a speckle light pattern) (step 124), and intensity values of the spatial components of the interference light pattern 48 are stored by the corresponding detectors 68) (step 126). In the case where a single interference light pattern 48 is generated, all of the detectors 68 of the single detector array 28 will simultaneously detect respective spatial components of the interference light pattern 48, and in the case where two phase modulated interference light patterns 48a, 48b are generated, all of the detectors 68 of both detector arrays 28a, 28b will simultaneously detect respective spatial components of the respective interference light patterns 48a, 48b.

Feedback control may be optionally employed by the controller 24 to ensure that the interferometer 22 remains balanced in the absence of fast-optical signals by sensing the sample arm or reference arm at the outputs of the light source 50 or frequency shifter 56, or by measuring the integration temporal beat components of the interference light pattern(s) 48 at the output of the interferometer 22 during known quiescent periods where there is an absence of a fast-optical signal in the target volume of interest 14, and using proportional integration differential control to modify the pulsed waveform of the sample light 40 and/or frequency offset $f_{shift}$ between the sample light 40 and reference light 42 to return the integration of the temporal beat component (s) to zero.

After the measurement has been taken, the controller 24 recalls the intensity values of the spatial components of the detected interference light pattern(s) 48 from the detector array(s) 28 and transfers these values to the processor 26 (step 128). The processor 26 generates an intensity population distribution based on a function of the intensity values of the spatial component values of the detected interference light pattern(s) 48 (step 130). Such function may be an identity function if only a single interference light pattern 48 is generated, in which case, the processor 26 will simply determine the intensity population distribution of the spatial component values of the detected interference light pattern (s) 48. Or such function may be a subtraction function if two phase-modulated interference light patterns 48 are generated, in which case, the processor 26 will subtract the intensity values of the interference light patterns 48 from each other in accordance with equation [27] to eliminate the DC noise, and then generates the intensity population distribution of the result.

The processor 26 then determines the spread of the intensity population distribution, and determines whether a fast-optical signal is present in the target volume of interest 14 based on the determined intensity population distribution spread. In particular, the processor 26 quantifies the spread of the intensity population distribution (e.g., by computing a standard deviation of the intensity population distribution) (step 132) and compares the quantified intensity population distribution to a reference threshold (value or level) (step 134). If the spread of the intensity population distribution remains narrow, indicating a balanced condition, i.e., the quantified intensity population distribution is below the reference threshold (step 136), the processor 26 determines that a fast-optical signal is absent in the target volume of interest 14 (step 138). In contrast, if the spread of the intensity population distribution broadens, indicating an unbalanced condition, i.e., the quantified intensity population distribution is above the reference threshold (step 136), the processor 26 determines that a fast-optical signal is present in the target volume of interest (step 140).

The processor 26 may optionally determine the magnitude of the fast-optical signal based on the extent to which the intensity population distribution has broadened, i.e., the broader the intensity population distribution the greater the intensity of the fast-optical signal (step 142). For example, if the processor 26 has identified the presence of a fast-optical signal in the target volume of interest 14, the processor 26 may recall a reference magnitude level or value corresponding to the quantified intensity population distribution spread from a look-up table, or otherwise compute the magnitude level or value from the quantified intensity population distribution spread.

In the case where the target volume of interest 14 is brain tissue, the processor 26 may further determine the level of neural activity within the target volume of interest 14 based on the identified fast-optical signal; that is, the absence of a fast-optical signal in the target volume of interest 14 indicates no neural activity in the target volume of interest 14, whereas the presence of a fast-optical signal in the target volume of interest 14 indicates at least some neural activity in the target volume of interest 14 (step 142). Multiple tissue volumes 14 may be measured by repeating steps 106-144 for different source-detector pairs created, e.g., using the arrangement illustrated in FIGS. 26-27.

It should be appreciated that the physiological event detection techniques described herein can be used in any optical detection system (including other types of diffusive optical systems, as well as pulsed UOT systems, optical coherence tomography (OCT) systems, and off-axis holography systems) that generates temporal beat interference components between sample light and reference light and is capable of selectively detecting a temporal beat interference component, and specifically, whether the temporal beat component integrates to a zero value or a non-zero value. In any of these systems, the manner in which the sample light pattern and reference light is combined into interference light pattern(s) and the detector array(s) used to detect the interference light pattern(s) may change, but the individual optical paths of the sample light and the reference light, as well as the processor used to generate and analyze the intensity population distributions, may remain the same.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A non-invasive optical detection system, comprising:
   an interferometer configured for delivering sample light having a rectangular pulse into a target volume of interest of an anatomical structure, whereby the sample light is scattered by the target volume of interest, resulting in a sample light pattern that exits the anatomical structure, the interferometer further configured for combining reference light with the sample light pattern to generate at least one interference light pattern, such that each of the at least one interference light pattern has a time varying interference component that integrates to a first value over a measurement period in the absence of a physiological event in the target volume of interest, and that integrates to a second value greater than the first value over the measured period in the presence of the physiological event, wherein the interferometer is further configured for shifting the sample light relative to the reference light by a frequency offset, such that the sample light pattern and the reference light are combined using a heterodyning technique, the measurement period is equal to an inverse of the frequency offset between the sample light and the reference light, and the product of the frequency offset between the sample light and the reference light and a duration of the rectangular pulse is equal to one;
   at least one array of detectors respectively configured for detecting intensities of spatial components of the at least one interference light pattern during the measurement period; and
   a processor configured for analyzing a function of the detected spatial component intensities of the at least one interference light pattern, and identifying a presence of the physiological event in the target volume of interest based on the analysis.

2. The non-invasive optical detection system of claim 1, wherein the first value is approximately a zero value.

3. The non-invasive optical detection system of claim 2, wherein the first value is equal to or less than one percent of the integral of the absolute function of the time varying interference component.

4. The non-invasive optical detection system of claim 1, wherein the target volume of interest comprises brain tissue and the physiological event is a fast-optical signal, wherein the system is configured for determining neural activity within the brain tissue based on the fast-optical signal.

5. The non-invasive optical detection system of claim 1, further comprising a controller configured for using feedback control to periodically modify one or more of a waveform shape of the sample light and the frequency offset between the sample light and the reference light to minimize the first value.

6. The non-invasive optical detection system of claim 1, wherein the interferometer comprises a light source configured for generating source light, a beam splitter configured for splitting the source light into the sample light and the reference light.

7. The non-invasive optical detection system of claim 1, wherein the processor is configured for analyzing the function of the detected spatial component intensities of the at least one interference light pattern by analyzing an intensity population distribution of the function of the detected spatial component intensities of the at least one interference light pattern, and determining a spread of the analyzed intensity population distribution, and wherein the presence of the physiological event in the target volume of interest is identified based on the determined intensity population distribution spread.

8. The non-invasive optical detection system of claim 7, wherein the processor is configured for determining the intensity population distribution spread by computing a standard deviation of the intensity population distribution.

9. The non-invasive optical detection system of claim 7, wherein the processor is configured for quantifying the spread of the intensity population distribution, and identifying the presence of the physiological event in the tissue voxel only if the quantified intensity population distribution spread is greater than a reference threshold.

10. The non-invasive optical detection system of claim 9, wherein the processor is configured for determining a magnitude of the physiological event based on the quantified intensity population distribution spread.

11. A non-invasive optical detection method, comprising:
    delivering sample light having a rectangular pulse into a target volume of interest of an anatomical structure, whereby the sample light is scattered by the target volume of interest, resulting in a sample light pattern that exits the anatomical structure;
    shifting the sample light relative to reference light by a frequency offset;
    combining reference light with the sample light pattern using a heterodyning technique to generate at least one interference light pattern, such that each of the at least one interference light pattern has a time varying interference component that integrates to a first value over a measurement period in the absence of a physiological event in the target volume of interest, and that integrates to a second value greater than the first value over the measured period in the presence of the physiological event, wherein the measurement period is equal to an inverse of the frequency offset between the sample light and the reference light, and the product of the frequency offset between the sample light and the reference light and a duration of the rectangular pulse is equal to one;
    detecting intensities of spatial components of each of the at least one interference light pattern during the measurement period;
    analyzing a function of the detected spatial component intensities of the at least one interference light pattern; and
    identifying a presence of the physiological event in the target volume of interest based on the analysis.

12. The non-invasive optical detection method of claim 11, wherein the first value is approximately a zero value.

13. The non-invasive optical detection method of claim 11, wherein the first value is equal to or less than one percent of the integral of the absolute function of the time varying interference component.

14. The non-invasive optical detection method of claim 11, wherein the target volume of interest comprises brain tissue and the physiological event is a fast-optical signal, and wherein the method further comprises determining neural activity within the brain tissue based on the fast-optical signal.

15. The non-invasive optical detection method of claim 11, further comprising using feedback control to periodically modify one or more of a waveform shape of the sample light and the frequency offset between the sample light and the reference light to minimize the first value.

16. The non-invasive optical detection method of claim 11, wherein analyzing the function of the detected spatial component intensities of the at least one interference light pattern comprises analyzing an intensity population distribution of the function of the detected spatial component intensities of the at least one interference light pattern, and determining a spread of the analyzed intensity population distribution, and wherein the presence of a physiological event in the tissue voxel is identified based on the determined intensity population distribution spread.

17. The non-invasive optical detection method of claim 16, wherein the determining the intensity population distribution spread comprises computing a standard deviation of the intensity population distribution.

18. The non-invasive optical detection method of claim 16, further comprising quantifying the spread of the intensity population distribution, wherein the presence of the physiological event in the tissue voxel is identified only if the quantified intensity population distribution spread is greater than a reference threshold.

19. The non-invasive optical detection method of claim 18, further comprising determining a magnitude of the physiological event based on the quantified intensity population distribution spread.

* * * * *